United States Patent
Ozelius et al.

(10) Patent No.: US 6,921,814 B2
(45) Date of Patent: Jul. 26, 2005

(54) TORSIN, TORSIN-RELATED GENES AND METHODS OF DETECTING NEURONAL DISEASE

(75) Inventors: Laurie J. Ozelius, Bronx, NY (US); Xandra O. Breakefield, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 254 days.

(21) Appl. No.: 09/772,105

(22) Filed: Jan. 26, 2001

(65) Prior Publication Data

US 2001/0029015 A1 Oct. 11, 2001

Related U.S. Application Data

(63) Continuation-in-part of application No. 09/461,921, filed on Dec. 15, 1999, now abandoned, which is a continuation-in-part of application No. 09/218,363, filed on Dec. 22, 1998, now Pat. No. 6,387,616, which is a continuation-in-part of application No. 09/099,454, filed on Jun. 18, 1998, now abandoned.
(60) Provisional application No. 60/050,244, filed on Jun. 19, 1997.

(51) Int. Cl.$^7$ ............................................... C07H 21/04

(52) U.S. Cl. .................. 536/24.1; 536/23.1; 536/24.31; 435/6; 435/91.2

(58) Field of Search ............................... 536/23.1, 24.1, 536/24.31; 435/6, 92.1

(56) References Cited

U.S. PATENT DOCUMENTS 5,407,821 A    4/1995  Breakefield et al. ........... 435/6

FOREIGN PATENT DOCUMENTS

| EP | 0 398 709 | 5/1990 |
|---|---|---|
| WO | WO 97/07669 | 3/1997 |
| WO | WO 98/57984 | * 12/1998 |

OTHER PUBLICATIONS

NCBI Entrez database nucleotide sequences, National Center for Biotechnology Information, National Library of Medicine, NIH (Bethesda, MD, USA) Accession Al158207, Version 1, GI:7160605, Mar. 3, 2000.*
Ozelius et al. Nature Genetics. 1997. vol. 17, pp. 40–48.*
Augood, S. et al., "Expression of the Early–Onset Torsion Dystonia Gene (DYT1) in Human Brain," *Ann. Neurol.* 43:669–673 (May 1998).
Augood, S. et al., "Distribution of the mRNAs Encoding TorsinA and TorsinB in the Normal Adult Human Brain," *Ann. Neurol.*, 46:761–769 (1999).

Breakefield, X. et al., "Linkage Analysis in a Family with Dominantly Inherited Torsion Dystonia: Exclusion of the Pro–Opiomelanocortin and Glutamic Acid Decarboxylase Genes and Other Chromosomal Regions Using DNA Polymorphisms," *J. Neurogenet.* 3:159–175 (1986).
Breakefield, X. et al., "Early Onset Torsion Dystonia Caused by Dominant Defect in ATP–Binding Protein," *Society for Neuroscience Abstracts* 23:1962, Abstract 764.1 (1997).
Bressman, S. et al., "Idiopathic Dystonia Among Ashkenazi Jew: Evidence for Autosomal Dominant Inheritance," *Ann. Neurol.* 26:612–620 (1989).
Bressman, S. et al., "A Study of idiopathic torsion dystonia in a non–Jewish family: Evidence for genetic heterogeneity," *Neurology* 44:283–287 (1994).
Bressman, S. et al., "Dystonia in Ashkenazi Jews: Clinical Characterization of a Found Mutation," *Ann. Neurol.* 36:771–777 (1994).
Bressman, S. et al., "Secondary dystonia and the DYTI gene" *Neurology* 48:1571–1577 (1997).
Chatterjee, S. and Wong Jr., K., "Adeno–associated Virus Vectors for Gene Therapy of the Hematopoietic System," *Curr. Top. Microbiol. Immunol.* 218:61–73 (1996).
Dobyns, W. et. al., "Rapid–onset dystonia–parkinsonism," *Neurology* 43:2596–2602 (1993).
Dunbar, C., "Gene Transfer to Hematopoietic Stem Cells: Implications for Gene Therapy of Human Disease," *Annu. Rev. Med.* 47:11–20 (1996).
Gasser, T. et al., "Haplotype Analysis at the DYT1 Locus in Ashkenazi Jewish Patients with Occupational Hand Dystonia," *Movement Disorders* 11:163–166 (1996).
Geller, A. and Breakefield, X., "A Defective HSV–1 Vector Expresses *Escherichia coli* β–Galactosidase in Cultured Peripheral Neurons", *Science*, 241:1667–1669 (1988).
Gasser, T. et al., "The Autosomal Dominant Dystonias," *Brain Pathology* 2:297–308 (1992).
Holmgren, G. et al., "Adult onset idiopathic torsion dystonia is excluded from the DYT 1 region (9q34) in a Swedish family," *J. Neurol. Neurosurg. Psychiatry* 59:178–181 (1995).
Inzelberg, R. et al., "A Genetic Study of Idiopathic Torsion Dystonia in Israel," *Neurology* 46(2) Suppl. A172: (1996).
Klein, C. et al., "Clinical and Genetic Evaluation of a Family with a Mixed Dystonia Phenotype from South Tyrol," *Annals of Neurology* 44(3):394–398 (1998).

(Continued)

Primary Examiner—Gary Benzion
Assistant Examiner—Juliet C. Switzer
(74) Attorney, Agent, or Firm—Hamilton, Brook, Smith & Reynolds, P.C.

(57) ABSTRACT

The present invention relates to methods of detecting mutations and polymorphisms in the torsin gene, torsin-related genes, methods of detecting neuronal diseases mediated by these mutations and polymorphisms and nucleic acids used in these methods.

4 Claims, 25 Drawing Sheets

OTHER PUBLICATIONS

Klein, C. et al., "De novo mutations (GAG deletion) in the DYT1 gene in two non–Jewish patients with early–onset dystonia," *Human Molecular Genetics* 7:1133–1136 (1998).

Klein, C. et al., "A Genetic Study of 72 Patients with Idiopathic Focal Dystonia from Northern Germany," *Neurology* 50(4) Suppl. 4:A116–117 (1998).

Klein, C. et al., "Search for a Founder Mutation in Idiopathic Focal Dystonia from Northern Germany", *Am. J. Hum. Genet.* 63:1777–1782 (1998).

Klein, C. et al., "Genetic Analysis of Three Patients with an 18p–Syndrome and dystonia" *Neurology*, 649–651 (1999).

Kramer, P. et al., "Dystonia Gene in Ashkenazi Jewish Population Is Located on Chromosome 9q32–34," *Ann. Neurol.* 27:114–120 (1990).

Kramer, P. et al., "The DYTI Gene on 9q34 Is Responsible for Most Cases of Early Limb–Onset Idiopathic Torsin Dystonia in Non–Jews," *Am. J. Hum. Genet.* 55:468–475 (1994).

Kwiatkoski, D. et al., "Torsion Dystonia Genes in Two Populations Confined to a Small Region on Chromosome 9q32–34," *Am. J. Hum. Genet.* 49:366–371 (1991).

Ozelius, L., Ph.D. Dissertation (Breakefield, X.O.—Advisor) "Definition of the Region of Human Chromosome 9Q Containing a Dystonia Gene," vol. 55–08B, pp 3124, 156 pages, Harvard University (1994).

Ozelius, L. et al., "Human Gene for Torsion Dystonia Located on Chromosome 9q32–q34," *Neuron* 2:1427–1434 (1989).

Ozelius, L. et al., "Strong Allelic Association between the Torsion Dystonia Gene (DYTI) and Loci on Chromosome 9q34 in Ashkenazi Jews," *Am. J. Hum. Gent.* 50:619–628 (1992).

Ozelius, L. et al., "Fine Mapping of the Human Dystonia Gene (DTY1) on 9q34 and Evaluation of a Candidate cDNA" *American Journal of Human Genetics*, 51:Suppl., (1992).

Ozelius, L. et al., "Fine Localization of the Torsion Dystonia Gene (DYT1) on Human Chromosome 9q34: YAC Map and Linkage Disequilibrium," *Genome Res.* 7:483–494 (1997).

Ozelius, L. et al., "The early–onset torsion dystonia gene (DYT1) encodes an ATP–binding protein," *Nature Genet.* 17:40–48 (1997).

Page, C. et al., "Genetic Analysis of Three Patients with Dystonia and Deletion in Chromosome 18p," *Neurology* 50(4) Suppl. 4:A427 (1998).

Pramstaller, P. et al., "Clinical and Genetic Characterization of a Family from South Tyrol (Northern Italy) with an Unusual Presentation of Dystonia," *Neurology* 50(4) Suppl. 4:A93–A94 (1998).

Risch, N. et al., "Segregation Analysis of Idiopathic Torsion Dystonia in Ashkenazi Jews Suggests Autosomal Dominant Inheritance," *Am. J. Hum. Genet.* 46:533–538 (1990).

Risch, N. et al., "Genetic analysis of idiopathic torsion dystonia in Ashkenazi Jews and their recent descent from a small founder population," *Nature Gent.* 9:152–159 (1995).

Saeki, Y. et al., "Herpes Simplex Virus Type 1 DNA Amplified as Bacterial Artificial Chromosome in *Escherichia coli*: Rescue of Replication–Competent Virus Progeny and Packaging of Amplicon Vectors", *Human Gene Therapy*, 9:2787–2794 (1998).

Schmidt–Wolf, G. et al., "Bone Marrow and Clinical Gene Therapy," *J. Hematotherapy* 4:551–561 (1995).

Shaughnessy, E. et al., "Parvoviral Vectors for the Gene Therapy of Cancer," *Semin. Oncology* 23:159–171 (1996).

Zhang, W.–W. "Antisense oncogene and tumor suppressor gene therapy of cancer," *J. Mol. Med.* 74:191–204 (1996).

Breakefield, X. and Bressman S., "Molecular genetics of movement disorders," In *Movement Disorders*, C.D. Marsden et al., eds. vol. 2: (Boston, Butterworth Scientific), (1987).

Fahn, S. et al., "Idiopathic torsion dystonia in Ashkenazi Jews: Autosomal dominant inheritance pattern of gene located on chromosome 9q32–34," In *New Perspectives on Genetic Markers and Disease Among Jewish People*, E. Batsheva, ed. (NY, Oxford University Press) 202–219, (1992).

Kramer, P. et al., "The molecular genetics of an autosomal dominant form of torsion dystonia," *Adv. Neurol*,. 50:57–66, (1988).

Kramer P. et al., "Exclusion of autosomal dominant dystonia gene from large regions of chromosomes 11, 13q and 21q by multi–point linkage analysis," *Genetic Epidemiol.*, 4:377–387, (1987).

Kramer P. et al., "The Genetics of Dystonia," In *Handbook of Dystonia*, J. Tsui et al., eds., 43–58, (1995).

Kwiatowski, D. et al., "The gelsolin cDNA clone, from 9q32–34, identifies Be11 and Stul RFLPs.," *Nuc. Acids. Res.*, 17:4425, (1989).

Kwiatkowski, D. et al., "Torsion dystonia genes in two populations confined to a small region on chromosome 9q32–34.," *Am. J. Hum. Gen.*, 49:366–371, (1991).

Ozelius, L. et al., "Torsion Dystonia.," In *Advances in Jewish Genetic Diseases*, R. Desnick, ed. Oxford University.

Ozelius, L. et al., "Early–onset, generalized dystonia cause by DYT1 gene on chromosome 9q34. Monographs in Neural Sciences,", *Age–Related Dopamine–Dependent Disorders*, vol. 14:126–132, (1995).

Ozelius, L. et al., "The gene (DYT1) for early–onset torsion dystonia encodes a novel protein related to the Clp protease/ heat shock family.," *Dystonia 3*, S. Fahn, et al., eds. (Philadelphia, Lippincott–Raven) 78:93–105, (1998).

Ozelius, L. et al. "Dinucleotide repeat polymorphism for the hexabrachion gene (HXB) on chromosome 9q32–34.," *Human Mol. Gen.* 1:141, (1992).

Schuback, D. et al. Ban I RFLP at AK1 locus (9q34). *Nucleic Acids Res.*, 19:5798, (1991).

\* cited by examiner cDNA DQ1

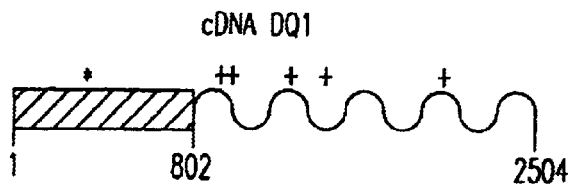

Polymorphisms: C/T @ 343, proline/proline

Transcript size: 2.7kb cDNA DQ2

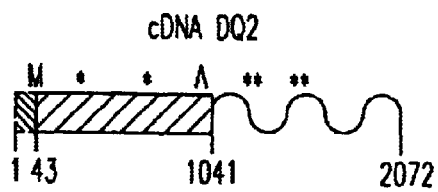

Polymorphisms: C/T @ 288, alanine/alanine
G/C @ 688, aspartic acid/histidine
G/T @ 1232
C/G @ 1255
del/T @ 1464
T/A @ 1495

Mutation: del/GAG @ 946, del/glutamic acid

Transcript size: 2.2kb, 1.4kb cDNA DQ3

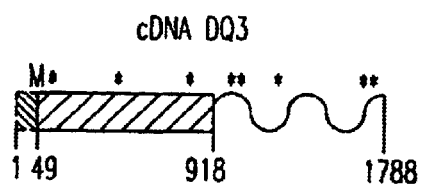

Polymorphisms: A/G @ 156, glutamic acid/glutamic acid
A/G @ 420, lysine/lysine
T/C @ 801, glycine/glycine
AC/CT @ 1005
G/A @ 1063
(T)n @ 1273
T/A @ 1724
A/G @ 1751

Transcript size: 1.8kb cDNA DQ4

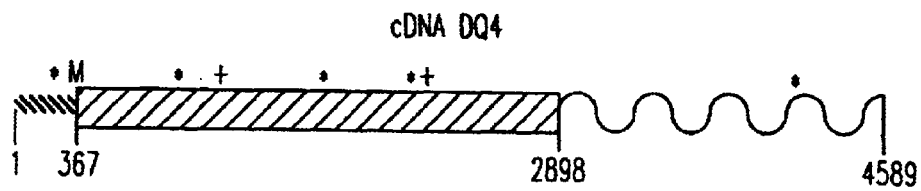

Polymorphisms: G/A @ 225
C/T @ 840, alanine/alanine
G/A @ 1696, valine/isoleucine
C/T @ 2172, histidine/histidine
G/A @ 4225

Transcript size: 4.5kb

FIG.2

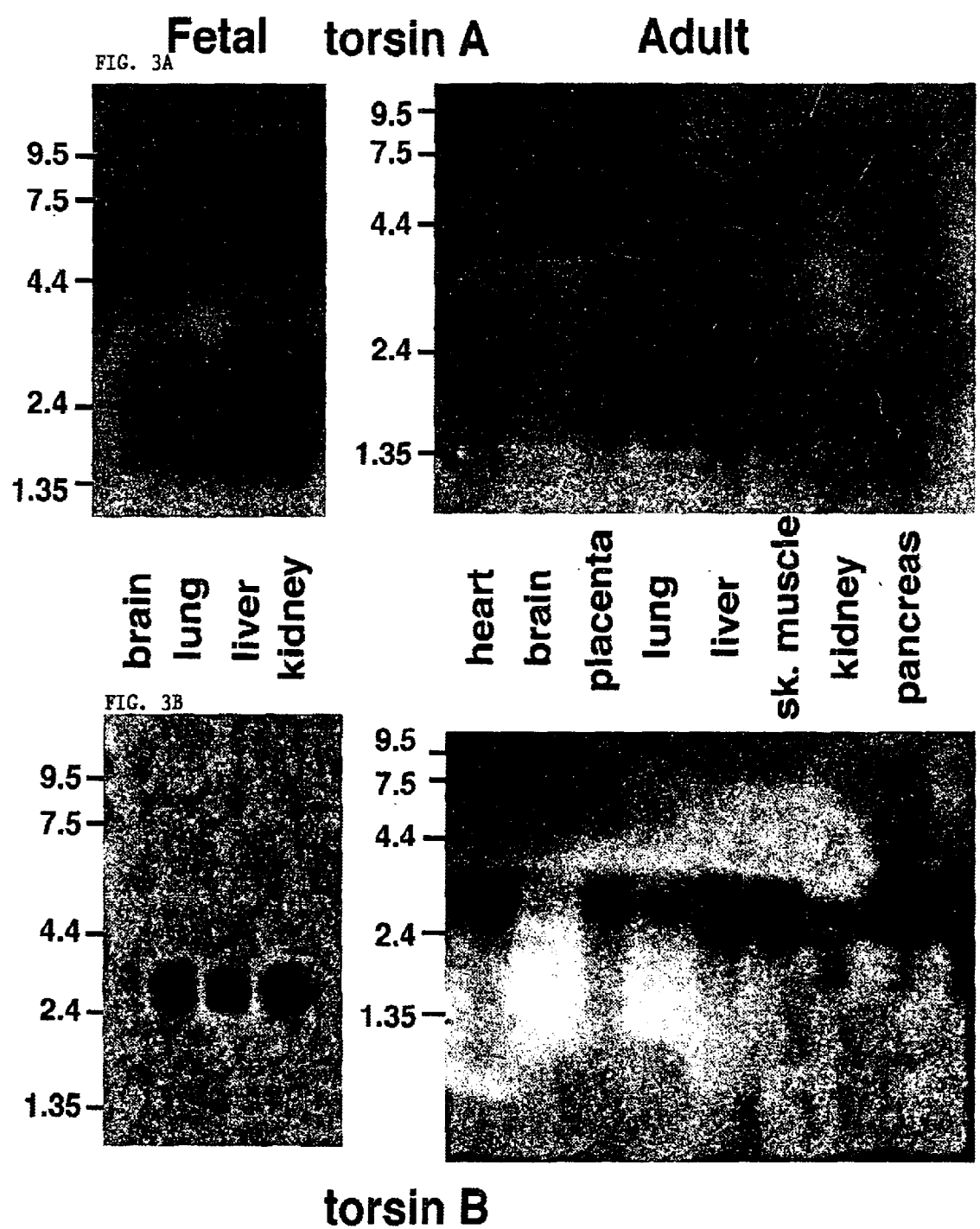

*DYT1*

| Exon | Size (bp) | 3' end of exon | 5' splice site (SEQ ID NO) | Intron (kb)* | 3' splice site (SEQ ID NO) | 5' end of exon (SEQ ID NO) | Exon |
|---|---|---|---|---|---|---|---|
| 1 | 178 | ...CGG GAG G<br>R E A | GTAGGCTGGG... (67) | 1.2 | ...TCTTTCCCAG (71) | CA CTG CAG AAG... (75)<br>L G K | 2 |
| 2 | 266 | ...TTG TAC AAG<br>L Y K | GCAAGGATGG...(68) | 1.5 | ...TTTAATTCAG (72) | GAT CAG TTA...<br>D Q L | 3 |
| 3 | 176 | ...TTT CTC AG<br>F L S | GTAAGGTCAG... (69) | 0.097 | ...TGTTTTGCAG (73) | C AAT GCT GGA... (76)<br>N A G | 4 |
| 4 | 128 | ...AAG AAC AG<br>K N S | GTGAGTAGGG... (70) | 4 | ...TTCTTCCCAG (74) | T GGC TTC TGG... (77)<br>G F W | 5 |
| 5 | 251 | ...GAT GAT TGA<br>D D * | | | | | |

FIG. 9B

*TORB*

| Exon | Size (bp) | 3' end of exon | 5' splice site (SEQ ID NO) | Intron (kb)* | 3' splice site (SEQ ID NO) | 5' end of exon (SEQ ID NO) | Exon |
|---|---|---|---|---|---|---|---|
| 1 | n.d. | ...GCT TCG G<br>A S A | | n.d. | ...GTTCTTGCAG (81) | CT CTC AAG CTG... (85)<br>L K L | 2 |
| 2 | 266 | ...CTG TAC CAG<br>L Y Q | GCAAGAGAAC... (78) | 3 | ...GTTGGTCCAG (82) | GAC CAG TTA...<br>D Q L | 3 |
| 3 | 176 | ...TTT CTC AG<br>F L S | GTCAGCGGGA... (79) | 1.8 | ...GCAAACTCAG (83) | C AAT GCA GGC... (86)<br>N A G | 4 |
| 4 | 128 | ...AAA CAC AG<br>K H S | GTGAGTCCAC... (80) | .31 | ...TGTTCTGCAG (84) | T GGC CTG TGG... (87)<br>G L W | 5 |
| 5 | 242 | ...TTC CAC TGA<br>F H * | | | | | |

*Sizes of introns were approximated by gel resolution of PCR products

FIG. 10

| Type | Number of Individuals | Age of onset yrs | Site of onset[a] (no.) | Sites involved (no.) |
|---|---|---|---|---|
| Early onset: | | | | |
| AJ | 5 | 6, 8, 8, 10, 19 | A(4), ANL(1) | A(7), N(3), T(1), L(2) |
| NJ | 12 | 3, 6(2), 8, 9, 10, 11, 13, 14(2), 16, 18 | A(9), AU(1) | A(20), G(9), |
| | | | G(1), L(1) | R(6), K(4), U(4), L(4), |
| | | | | N(6), P(1), S(1), T(2), |
| | | | | F(2), J(3), U(2) |
| Potential homozygosity: | | | | |
| AJ[b] | 5 | 4, 6, 7, 28, 35 | L(4), M(1) | L(4), M(1), N(2), P(1), |
| | | | | T(1), U(1), H(2) |
| Late onset: | | | | |
| AJ | 1 | 66 | U | U |

[a] Body sites: U=upper face, F=lower face, J=jaw, T=tongue, P=pharynx, L=larynx, S=speech, swallowing, A=arm, K=trunk, G=leg, N=neck, H=hearing loss. (no.=Number of individuals in group with that site affected.)
[b] Three of these individuals had all known AJ ancestors, one was 7/8 AJ, and one was 1/2 AJ.

Genotype

| Sample number | D9S2160[a] | D9S2161 | D9S63 | D9S2162 |
|---|---|---|---|---|
| 18843 | 3,4 | 2,2 | 8,8 | 4,4 |
| 13709 | 4,4 | 2,6 | 14,14 | NT[b] |
| 14122[c] | 3,3 | 4,4 | 0,0 | 5,5 |
| 13945 | 4,4 | 1,5 | 18,18 | NT[b] |
| 14040 | 2,5 | 1,2 | 16,16 | 2,4 |

[a] Markers listed from centromere to telomere: D9S2160 - <40 kb - D9S2161 - 150 kb - D9S63 - 130 kb - D9S2162 (Ozelius et al., 1997a).
* Position of DYT1 gene
[b] Not tested.
[c] This individual had onset at 7 years in the arm with eventual involvement of the arm and neck and a positive family history of movement disorder (father with tremor). He was also apparently homozygous for markers D9S159-D9S2158-D9S2159, which are proximal to DS2160 (total region of 100 kb).

| Intron Primers Used to Amplify DYT1 Exons ||||
|---|---|---|---|
| Exon | Primer Sequence (5'→3') | SEQ. ID NO.: | Product Size (bp)* |
| 1 | GCAAAACAGGGCTTTGTACCG | (SEQ. ID NO.: 30) | |
| | AGTAGAGACGCGGGTAGATG | (SEQ. ID NO.: 31) | |
| | GCGTCTCTACTGCCTCTTCG | (SEQ. ID NO.: 32) | |
| | ATGCCCTGGTCCTAGTTCAG | (SEQ. ID NO.: 33) | |
| 2 | GGTTTCGCAAGGTGCTTGGA | (SEQ. ID NO.: 34) | 408 |
| | GGGATTCCAAACTTCCATCC | (SEQ. ID NO.: 35) | |
| 3 and 4 | TCCATGGGGTTGGTAGGAAC | (SEQ. ID NO.: 36) | 804 |
| | GGTGACAGAGTAAAACTATCTG | (SEQ. ID NO.: 37) | |
| 5 | GACCCCCAGTAGACGTTTGT | (SEQ. ID NO.: 38) | 640 |
| | GTAAAAAATCATGAGCCCTGC | (SEQ. ID NO.: 39) | |

FIG. 12B

| Intron Primers Used to Amplify TORB Exons ||||
|---|---|---|---|
| Exon | Primer Sequence (5'→3') | SEQ. ID NO.: | Product Size (bp)* |
| 1 | n.d.# | | |
| 2 | CCAGAGTTAGTGAGCAGGTC | (SEQ. ID NO.: 40) | 526 |
| | GAAGCGTTAAGGACCTCCAC | (SEQ. ID NO.: 41) | |
| 3 | ATCTATCTCTGCCAATTTCCAC | (SEQ. ID NO.: 42) | 466 |
| | GTCCTGGTAAACAAAGTGCTG | (SEQ. ID NO.: 43) | |
| 4 | TGGGGTTACTCTATGTTGGTC | (SEQ. ID NO.: 44) | 440 |
| | CTAGCACAGTATGCCCTAAG | (SEQ. ID NO.: 45) | |
| 5 | TGAGGAATGTGCTGAGGGTC | (SEQ. ID NO.: 46) | 333 |
| | GCTGTCTCCTACCCCATCTG | (SEQ. ID NO.: 47) | |

*PCR products were generated using oligonucleotides synthesized from intronic sequences, and accordingly the size of each product includes both intron and exon sequence.

Not done. It was not possible to identify primers which could consistently PCR this exon.

| Protein | Organism | Gene | Locus | Accession | UniGene |
|---|---|---|---|---|---|
| hTorsinA | human | DYT1 | Chr.9, D9S159-D9S164 | AF007871 | Hs.19261 |
| mTorsinA | mouse | | | AA230756 | Mm.40438 |
| rTorsinA | rat | | | AA850233 | Rn.20041 |
| sTorsinA | pig | | | AU058534 | |
| | | | | | |
| hTorsinB | human | TORB | Chr.9, D9S159-D9S164 | AF007872 | Hs.5091 |
| mTorsinB | mouse | | | AA596988 | |
| | | | | | |
| drTorsinC | zebrafish | | | AA542632 | |
| | | | | | |
| hTorp1 | human | TORP1 | | AA873275 | Hs.59038 |
| mTorp1 | mouse | | | AA981789 | Mm.33875 |
| rTorp1 | rat | | | H31561 | |
| | | | | | |
| hTorp2 | human | TORP2 | | AA150869 | Hs.26267 |
| mTorp2 | mouse | | | AA791729 | |
| | | | | | |
| dmTorp3 | fruitfly | EG:84H4.1 | DMC84H4 | AL031766 | |
| | | | | | |
| ceTorp4A | nematode | F44G4.1 | CEC18E9 | P54073 | |
| ceTorp4B | nematode | Y37A1B.12 | CEY37A1B | AL023835 | |
| ceTorp4C | nematode | Y37A1B.13 | CEY37A1B | AL023835 | |

FIG. 13

INTRON 1 OF DYT1 GENE

FIG. 14A: Clone 1:
23g14-2-7050.cDNA (Length: 283) SEQ ID NO.: 48

```
1    gtaggctggg gcggggctg gaggctgggg ctggggctgg ggctgggcga
51   tggcactagg gctgaactag gaccagggca tggagaatgg aggatggagg
101  ccggggatg gcaccagggc cgggctagga ctagggctgg agcggggcct
151  gggggctggg gctgggcgat ggcactaggg cgggttgggg ctggggctgg
201  ggctggggga tggagcgggg ccggggctg ggggtggggc tggggatcg
251  actagggctg gnttaggacc aggcggttgg cat
```

Bold = primer 4 (reverse sequence) from FIG. 12A
Underline = 5' splice sequence from Intron 1 FIG. 9A FIG. 14B: Clone 2:
Harvey7-23g14-2.cDNA (Length: 375) SEQ ID NO.: 49

```
1    ggatggtgga tggaggctgg gggatggcag tagggccggg ctaggactgg
51   ggctggagcg gagtttgggg ctggggctca ggagcggggg ctggggctgg
101  ggctgggggct gggggatggc actagggcag gccggggtag gggtcacatc
151  ccaggagggc cggctgggc agagctgagt ccgcgggggc cggaccccgg
201  aagccaagcn gccggcctgc aggatgaggc ctggctcctc ggccatgacc
251  acagacgtgc cagacttaag tacggagacc tgaggagcca ggctgcagtt
301  ggcctacttt ncnctaagct gggggtggac cagtggtaac ctcctccgaa
351  gtgggttctg ctctttctag cctag
```

FIG. 14C: Clone 3:
23g1-Harvey11.cDNA (Length: 439) SEQ ID NO.: 50

```
1    ccactgccac tgccaccagt ttgcaccct aaccctgtn ctgctcctcc
51   caccccaagg cagagccggn gaaaggaaac agtttggtcc ctcctggtcg
101  gctgcggaag agtctcacca tccttctgtc tccgtagcta gaaaggaggc
151  agaacccaca ttcggaggga ggttaccact ggtccacccc cagcttagcg
201  caaagtaggc caacctgcat gcctggnnct cctcaggntc tgcctactta
251  agtctggcag ctctnnntca tggccgaggt agccaggctc atcctgcagg
301  nnccngccnn ttgncttncc ggggtntcgn nncccgtac tcagctcgtc
351  cagccggcct ctggatgtga cctaccgctg ctagtgcatc ccagccagcc
401  agccagccgt ctagccagcc aactgctcag ccagtctag
```

FIG. 14D: Clone 4:
23g1-Harvey6.cDNA (Length: 378) SEQ ID NO.: 51

```
1    ctgggaaaga caaagccaat caggagtggg gaagaaacac ggcaaaatgt
51   agccacattt acagcccata aganagccag caaagccgtc tagcctccaa
101  gcaccttgcg aaacctcaag tactgcggtc tggtaagctc ctggcccaga
151  ggggacggcg gtccagggng ccctcccttt gctggtcctg cctattctaa
201  agccctggcc cgnctccttc ccgaaaagcc ccttggtgcc actgccactg
251  ccaccanttt gcnccctac ccctgtnctg ctcctccac cccaaggcag
301  atgcggnngg ngaaaggaaa cantttggtc cctcctggtc ggctcgngga
351  agactcctca ccatccttcc tgtcttcc
```

Bold = primer 5 from FIG. 12A
Italics = sequence overlap between Clone 4 and Clone 3
Underline = 3' splice site from FIG. 9A FIG. 14E: Clone 4:
23g1-Harvey6.cDNA (Length: 388) SEQ ID NO.: 88

```
1    ctgggaaaga ctgggaaaga caaagccaat caggagtggg gaagaaacac
51   ggcaaaatgt agccacattt acagcccata aganagccag caaagccgtc
101  tagcctccaa gcaccttgcg aaacctcaag tactgcggtc tggtaagctc
151  ctggcccaga ggggacggcg gtccagggng ccctcccttt gctggtcctg
201  cctattctaa agccctggcc cgnctccttc ccgaaaagcc ccttggtgcc
251  actgccactg ccaccanttt gcnccctac cctgtnctg ctcctcccac
301  cccaaggcag atgcggnngg ngaaaggaaa cantttggtc cctcctggtc
351  ggctcgngga agactcctca ccatccttcc tgtcttcc
```

Bold = primer 5 from FIG. 12A
Italics = sequence overlap between Clone 4 and Clone 3
Underline = 3' splice site from FIG. 9A

INTRON 2 DYT1 GENE

FIG. 15A: Clone 1:
29a5-6343.cDNA (Length: 400) SEQ ID NO.: 52

```
1    gaatatttac gagggtggtc tgaacagtga ctatgtccac ctgtttgtgg
51   ccacattgct ctttccacat gcttcaaaca tcaccttgta caaggcaagg
101  atggaagttt ggaatccctt cctggatgtc atcgggtttg ggtctcttt
151  gttgtgggat gagatttggg agttctatgt tgaaatgagt gagcccggaa
201  aacggttcat gtctcagttc cccttggaaa ggtgtagaag ttaagagttt
251  gagatgcgtg gagcagttaa taccatcaaa gctttgtggt gggttctgaa
301  aatcggtcca gtgagtatgt agggtcatgg gattttagag gtggacatga
351  tcaaatccat cttagagatc aacacatctc actcattttt attttcttat
```

Bold = primer 6 from FIG. 12A
Underline = 5' splice site sequence for intron 2 from FIG. 9A FIG. 15B: Clone 1:
29a5-6343.cDNA (Length: 402) SEQ ID NO.: 89

```
1    gaatatttac gagggtggtc tgaacagtga ctatgtccac ctgtttgtgg
51   ccacattgct ctttccacat gcttcaaaca tcaccttgta caaggcaagg
101  atggaagttt ggaatccctt cctggatgtc atcgggtttg ggtctcttt
151  gttgtgggat gagatttggg agttctatgt tgaaatgagt gagcccggaa
201  aacggttcat gtctcagttc cccttggaaa ggtgtagaag ttaagagttt
251  gagatgcgtg gagcagttaa taccatcaaa gctttgtggt gggttctgaa
301  aatcggtcca gtgagtatgt agggtcatgg gattttagag gtggacatga
351  tcaaatccat cttagagatc aacacatctc actcattttt attttcttat
401  tt
```

Bold = primer 6 from FIG. 12A
Underline = 5' splice site sequence for intron 2 from FIG. 9A FIG. 15C: Clone 2:
6550-54a5s.cDNA (Length: 418) SEQ ID NO.: 53

```
1    tttggagtga gacaggactg ggttcaggtc ccagctctgc cacatatagt
51   cttgggcaag tggagtaagc gctctctgtg cctcagttcc ctcatctgta
101  aaatgagaac gatagtgccc actccatggg gttggtagga acaaagaaga
151  ttttgggcat gtaaagttct tagtgccgag tgcacagtgg tctgtaagtg
201  aagctgcggt tcttagtggt agaaggagct gattgatggc cctggctgag
251  aactttgtgt tcgcttttc ccntttaat tcaggatcag ttacagttgt
301  ggattcgagg caacgtgagt gcctgtgcga ggtccatctt catatttgat
351  gaaatggata agatgcatgc aggcctcata gatgccntca anccttcct
401  cgactattat gacctggt
```

Bold = primer 7 from FIG. 12a
Underline = 3' splice sequence for intron 2 from FIG. 9A
Italics = EXON 3 sequence

INTRON 3 DYT1

FIG. 16A: Clone 1:
6202-54a5.cDNA (Length: 198) SEQ ID NO.: 54

```
1    ctcgactatt atgacctggt ggatggggtc tcctaccaga aagccatgtt
51   catatttctc aggtaaggtc agggctagga catgatggat gggccccgag
101  cccaagcctc tgagctccag gagaaaaccc tgtccttacc cactgggatt
151  gttttgcagc aatgctggag cagaaaggat cacagatgtg tttggatt
```

FIG. 16B: Clone 1:
6202-54a5.cDNA (Length: 200) SEQ ID NO.: 90

```
1    ctcgactatt atgacctggt ggatggggtc tcctaccaga aagccatgtt
51   catatttctc aggtaaggtc agggctagga catgatggat gggccccgag
101  cccaagcctc tgagctccag gagaaaaccc tgtccttacc cactgggatt
151  gttttgcagc aatgctggag cagaaaggat cacagatgtg gctttggatt
```

Bold = EXON
Underline = sequence from for 5' splice site sequence and 3' splice site sequence, respectively from FIG. 9A

INTRON 4 DYT1

FIG. 17A: Clone 1:
Intron 4-5 prime.cDNA (Length: 535) SEQ ID NO.: 55

```
  1   GTCTGTGTCG GTTTTCAATA ACAAGAACAG gTGAGTAGGG CCATCCACCG
 51   CCAGTCCCAT CTGGTTCCTA ATCCTGCACC CTAAGTGTTA AAAGCATCAG
101   GGTCACTGTC AGCATCACCT GGGAGCTGGG TAGAAAGAAA TGgAGATTCT
151   CAGTCCCCTT CCGAGTCATG AGGGGAATCT TTGCTGATGA ACTCCAGGTA
201   ACTTTTATGA ACACTAATGT TTGACAAGTG CTGTTTTATT TTTATTTTTC
251   AGATAGTTTT ACTCTGTCAC CTAGGCTGGA GTGCAGTGGC GTAACCTTGC
301   CTCACTGCAA CCTCTGCCTC CCGGGCTCAA GCGATTCTTG TGCCTCAGCC
351   TCCTGAGTAG CTGGGATTAC AGGTGCACAC CATGCCCAAG CNAATATTTT
401   GTATTTTAG TAGAGANGGG GCCCCGTNCA TGTTAACCAG GCTGGTCTTG
451   AACTNTTACC TCAGGTGAGT CCNCCACCTC GGCCTCCCAA AGTGCTGGGA
501   TTACAGGCGT GAGCCACTGT GTCTCAGCTT ATTTTT
```

Italics = EXON sequence
Underline = 5' splice sequence from FIG. 9A
Bold = primer 8 from FIG. 12A FIG. 17B: Clone 2:
Intron 4-3 prime.cDNA (Length: 1302) SEQ ID NO.: 56

```
   1   GCCACTCCAA GCTACCATCT GAGATTGTTT CCTGCCCTAG AGTGGTAAAG
  51   GCGTGAGGTC CGTCTGCCCT CAGCTGTGTC CCCAGGCCCA GGGCGTGCCT
 101   GGCAACANNA GCAGGCCTCT GAGAACCAGC CTCCCACGTG AGTTCATGAT
 151   AGNAAGACAG CCCCTCGTTC CCATTCAGTG GTTGGTTCTG TTCTTTYCCT
 201   GGCMATAAGC TCCACTCTGY MRTCAGCCAM ACATTTATTG AGTACCAGTT
 251   GTTGGCAAAG CACTGTTGGG CATGAAAAGC ATTAACCCAG TGAATGAGGA
 301   GGAGCTTGGG TTGGGACGGA GCCMCARAAW TACATGGCAG ACCAGAAGGA
 351   AATCAGCTCA AGTAGAAARA CACGCATGGG CTCGTGGGCG ACGCAGTGTG
 401   TGCTGTGTCA TCTGGGGCTG GGAGGAAGTG TCCTGGATCA GGAGTTCCAG
 451   GAGCCCAGGA GGAGTGGACG GGTCAGTGCA GAGCCAGCCC GCAATCAGGG
 501   GAAGAAAACA CGGCCAAGGC CAGGCCTTCA CGGGGAGCCC AGCGTGGGCT
 551   GCACATCTGC ACTCTCCAGG CTAGTTTTGG TGCCCACATG CTCTGCAGGG
 601   TCTGGGCACT GTGGCAGCGG CAGCAGGCTT CCCTGTTGCT AGTCCAGCTG
 651   CTGAAACTCC AGGGAGAGTC AAAAAGTTCC CAAATACAGA GGCGTGGCTG
 701   GTAGTCCTTC CCGGGAATTC TTCTTGCTTC CCGCTTTCTG TGGAACTCTG
 751   CCTTCCCCAC TCTGCCTCTC TGCTTGTTCC TGGGCCCCAG GACCTCTTTC
 801   CCATCTTCGA TCTCTTAAGT CATACCTTGG GAGGCCTCCC CCAGCCCGCC
 851   GTGTAAAGAG GGCTGTCACA GCTTCTGCTG TCACAGAAGC ATTACAATGT
 901   GCAGGTGCCT GTTAACATCT GCCTTCCCCA CTGATCTGGA GCTCCACAAG
 951   GGAGAGGGCA CACCCAGTAG GTATGTGTGG GATGGATAGG AGGGTGGATG
1001   ACACCCAGTA GATGTGTATG GGATGGATAG GAGGGTGGAT GACACCCAGT
1051   AGGTGTGTAT GGGATGGATG GGAGGGTGGG TGACCCCTAG TAGATGTGGG
1101   GGGGGTGGGT GGGTGACCCC CAGTAGGTGT GTGTGGCATG GATAGGTGAC
1151   CCCCAGTAGA CGTTTGTGGG ACGGATGGGA GGGTAGGTAA GTGACCCCCA
1201   GGAGGCGTCT ATAGGGCAGG TGGGTGGATG TGGATGAACA GCACCTTGTT
1251   TCTTCTTCCC AGGTGGCTTC TGGCACAGCA GCTTAATTGA CCGGAACCTC
1301   AT
```

Bold = primer 9 in FIG. 12A
Underline is 3' splice site sequence from FIG. 9A
Italics is EXON 5 sequence INTRON 1 5' from TORB FIG 18A: Clone 1:
h59-29a5.se (Length: 240) SEQ ID NO.: 57

```
  1   ggagcggccg ctcaacgctt cgggtacggc gcgcgcgcga gctgtgggtc
 51   ggcgctgcgg ggggcgcggg ggcgcggggg cgcggaggga cggcctcgtg
101   ggcgcctggc acggaccggg cccgtggcat ctagacggcg gtggtcccag
151   ctggggtggg cggggagcgg atggggcggc cccggaaccg ttcgcnggaa
201   cgcagaagcn gtgccttgaa acactctcag atcgtgnggc
```

INTRON 1 3' from TORB

FIG. 18B: Clone 2:
5667s-29a5.Se (Length: 310) SEQ ID NO.: 58

```
  1   gggaccaaag gacgtccgtc gttcccaccg accctaatcg ttcgcgngtc
 51   ngttcgctac ccagtagaga gacttactta cnngtnnatc gaaggaatag
101   tctggggctt cgcaattcct ggaggtgtat tagaactttc accgtagcaa
151   actgacggag ccgggatccc acaccgcctg tgggnncgac acgggaccta
201   ttgacacgaa gaacgaaacn gtcgattctt tcacgacgca acgactacgt
251   aaaaattcca gacaagaga gaaacaagac cccgacaaga acgtcGAGAG
301   TTCGACCTAA
```

Upper Case Letters = EXON (bottom strand)
Underline = sequence from Table 1
Bold = 2<sup>nd</sup> primer from FIG. 12B INTRON 2 5' from TORB FIG. 19A: Clone 1:
6101-29a5.Se (Length: 401) SEQ ID NO.: 59

```
1    CAGGAACAAC AAAAATCCCA AGAAACCACT GACCCTTTCC TTACACGGCT
51   GGGCTGGCAC AGGCAAGAAT TTTGTCAGTN AAATTGTGGC TGAAAATCTT
101  CACCCAAAAG GTCTGAAGAG TAACTTTGTC CACCTGTTTG TATCGACTCT
151  GCACTTCCCT CATGAGCAGA AGATAAAACT GTACCAGgca agagaacccg
201  ctattatctc gtctgcaggc cagtcggact ggtccgggtg acctgctcac
251  taactctggc ctctgcttct ctttcctttg tgttgctgta gccccggct
301  ccactgagtt aaggcacact tagtccaggt agttacaaag ctctcctaca
351  acatttctta cttggttcca aaacagtcca gtggggtagg ggatgttatt
401  t
```

Upper Case Letters = EXON
Underline = 5'splice site sequence from FIG. 9B
Bold = 1st primer from FIG. 12B

INTRON 2 3' TORB

FIG. 19B: Clone 2:
29A5-39-11.se (Length: 238) SEQ ID NO.: 60

```
1    ttctgtaact ggtcCTGGAC CAACCATGAA AGAAGAAACA GGATGCGAAG
51   CTCAAAGGGC TGCACCAAGA GGCGCGCAGG CTCCATCTGC TCCTCATGCA
101  CTGAAGGACG AGGTCAGAGC TCTTAGAATG CACCCTCAC CCCCACTCGC
151  TAGGTAGCAG CTTTTCTAAA ACCTTATCTC TAAAAAGTGG AAATTGGCAG
201  AGATAGATGC TAAAATGCAG AGAAGTTTTT CCTAACTC
```

Lower Case Letters = EXON
Underline = sequence from Table 1
Bold = primer 3 from FIG. 12B

INTRON 3 5' TORB

FIG. 20A: Clone 1:
39-14-29a5.Se (Length: 391) SEQ ID NO.: 61

```
1    GGGATCATTG ACGCAATCAA GCCGTTTCTA GACTACTACG AGCAGGTTGA
51   CGGAGTGTCT TACCGCAAAG CCATCTTCAT CTTTCTCAGg tcagcgggag
101  gcggttttt ggggcacaca agcccttcat tctctcaatg ataaaatgag
151  gtcctgagga ccatcagcac tttgtttacc aggacgaaag tgcctgcttg
201  gcacaaggca cttacctact gctttacttt tcctttgcca gtcatcagca
251  tggcacacag tgtgggttgt ggaaatgaac taaagaaata atcactggga
301  caggcgcggt ggctcacacc tgtcaatccn agcactttgg gnaggcatgg
351  cgggcggatc acaggagatc gagacatctg ctaacatgnt g
```

Upper Case Letters = EXON
Underline = 5' splice site sequence from FIG. 9B
Bold = primer 4 from FIG. 12B

INTRON 3 3' TORB

FIG. 20B: Clone 2:
5665s-54a5.Se (Length: 373) SEQ ID NO.: 62

```
1    gtaagacaca gagtcttttt tntttttag accgagtntc attnttgttg
51   ccnangctgg agtgcaatgg catgatctcg gctcgctgca acctccacct
101  cccggrttca aacgattctc ccacctcagc ctcccatgta gctgggatta
151  cagncatgca ccaccattag cctggctaat ttttgtgttt ttagtagaga
201  tggggttact ctatgttggt caggctggcc ttgaactccc gacctcaggt
251  gatctacctg cctcggcctc ccaaagtgct gggattacag ccatgagcna
301  ccacnscnan cagacncaga agtcttaata tgtgatttta atctttattt
351  ctctggcaaa ctcagCAATG CAG
```

Upper Case Letters = EXON
Underline = 3' splice site sequence from FIG. 9B
Bold = primer 5 from FIG. 12B

INTRON 4 TORB

FIG. 21: Clone 1:
intron4torb.se (Length: 310) SEQ ID NO.: 63

```
  1   gtgagtccac  cagggtaaag  gagcccctta  actgtccagc  agtgagccgt
 51   ctgctctttc  attgagtgtt  tgcacaaagc  cacaggatcc  cactggattt
101   cctcactttg  ctaaagtcag  gaattttctt  agggcatact  gtgctagaaa
151   ccagtgagtg  agtgtccagc  tgagtcctcg  atgggcttgt  tgcacactga
201   caagagacnc  tctcaagggg  tacggacatg  aggaatgtgc  tgagggtcgg
251   gactggagct  tggccaggtg  gcggtggtgg  caggaaaccc  agctgtgtct
301   tgttctgcag
```

Underline = 5' splice site sequence from FIG. 9B
Bold = primer 6 from FIG. 12B
Underline italics = 3' splice site sequence from FIG. 9B
Bold italics = primer 7 from FIG. 12B

SEQUENCE LISTING

```
<160> NUMBER OF SEQ ID NOS: 90

<210> SEQ ID NO 1
<211> LENGTH: 2597
<212> TYPE: DNA
<213> ORGANISM: Homo sapien
<220> FEATURE:
<221> NAME/KEY: CDS
<222> LOCATION: (568)...(1563)
<221> NAME/KEY: misc_feature
<222> LOCATION: (1)...(2597)
<223> OTHER INFORMATION: n = A, T, C or G

<400> SEQUENCE: 1
ctgaaaatag ctncttatta ttattattat tattattatt atttgcggga gggagcacag      60
tcttgctctg tctcccaggc tggagntgca gtggtgagat ctcggctcac tgcaatctcc     120
gcctcctggg ttcaagngca gttgctcatg tgtcagcctc cccagtagct agggctacag     180
gtgcctacca ccacaccggc taattttata tttttagtag agacgtggtt tcaccatgtt     240
ggtcaggctg gtctcgaact cctgacctca ggtgatccgc ccncctcagc ctncccaaag     300
ggctgggatt acaggcagga gccaccatnc ctggnaaaaa taacgtccat aaacaaaaac     360
acgtggccaa cagggcggag cagaaccgag tttccggaag caaaacaggg ctttgtaccg     420
aacaaagatg gcggccgccg gcgtcgggag gagggctgcc ctgaagaaag atggcctccg     480
cgagaggagg aanccggaag cgtgggtctg gcggctgcac cggttcgcgg tcggcgcgag     540
aacaagcagg gtggcgcggg tccgggc atg aag ctg ggc cgg gcc gtg ctg ggc    594
                                Met Lys Leu Gly Arg Ala Val Leu Gly
                                  1               5 ctg ctg ctg ctg gcg ccg tcc gtg gtg cag gcg gtg gag ccc atc agc      642
Leu Leu Leu Leu Ala Pro Ser Val Val Gln Ala Val Glu Pro Ile Ser
 10              15                  20                  25 ctg gga ctg gcc ctg gcc ggc gtc ctc acc ggc tac atc tac ccg cgt      690
Leu Gly Leu Ala Leu Ala Gly Val Leu Thr Gly Tyr Ile Tyr Pro Arg
             30                  35                  40 ctc tac tgc ctc ttc gcc gag tgc tgc ggg cag aag cgg agc ctt agc      738
Leu Tyr Cys Leu Phe Ala Glu Cys Cys Gly Gln Lys Arg Ser Leu Ser
         45                  50                  55 cgg gag gca ctg cag aag gat ctg gac gac aac ctc ttt gga cag cat      786
Arg Glu Ala Leu Gln Lys Asp Leu Asp Asp Asn Leu Phe Gly Gln His
     60                  65                  70 ctt gca aag aaa atc atc tta aat gcc gtg ttt ggt ttc ata aac aac      834
Leu Ala Lys Lys Ile Ile Leu Asn Ala Val Phe Gly Phe Ile Asn Asn
 75                  80                  85 cca aag ccc aag aaa cct ctc acg ctc tcc ctg cac ggg tgg aca ggc      882
Pro Lys Pro Lys Lys Pro Leu Thr Leu Ser Leu His Gly Trp Thr Gly
 90                  95                 100                 105 acc ggc aaa aat ttc gtc agc aag atc atc gca gag aat att tac gag      930
Thr Gly Lys Asn Phe Val Ser Lys Ile Ile Ala Glu Asn Ile Tyr Glu
                 110                 115                 120 ggt ggt ctg aac agt gac tat gtc cac ctg ttt gtg gcc aca ttg cac      978
Gly Gly Leu Asn Ser Asp Tyr Val His Leu Phe Val Ala Thr Leu His
             125                 130                 135 ttt cca cat gct tca aac atc acc ttg tac aag gat cag tta cag ttg     1026
Phe Pro His Ala Ser Asn Ile Thr Leu Tyr Lys Asp Gln Leu Gln Leu
         140                 145                 150 tgg att cga ggc aac gtg agt gcc tgt gcg agg tcc atc ttc ata ttt     1074
Trp Ile Arg Gly Asn Val Ser Ala Cys Ala Arg Ser Ile Phe Ile Phe
     155                 160                 165
```

|  |  |
|---|---|
| gat gaa atg gat aag atg cat gca ggc ctc ata gat gcc atc aag cct<br>Asp Glu Met Asp Lys Met His Ala Gly Leu Ile Asp Ala Ile Lys Pro<br>170                175               180               185 | 1122 |
| ttc ctc gac tat tat gac ctg gtg gat ggg gtc tcc tac cag aaa gcc<br>Phe Leu Asp Tyr Tyr Asp Leu Val Asp Gly Val Ser Tyr Gln Lys Ala<br>               190               195               200 | 1170 |
| atg ttc ata ttt ctc agc aat gct gga gca gaa agg atc aca gat gtg<br>Met Phe Ile Phe Leu Ser Asn Ala Gly Ala Glu Arg Ile Thr Asp Val<br>205                210               215 | 1218 |
| gct ttg gat ttc tgg agg agt gga aag cag agg gaa gac atc aag ctc<br>Ala Leu Asp Phe Trp Arg Ser Gly Lys Gln Arg Glu Asp Ile Lys Leu<br>220                225               230 | 1266 |
| aaa gac att gaa cac gcg ttg tct gtg tcg gtt ttc aat aac aag aac<br>Lys Asp Ile Glu His Ala Leu Ser Val Ser Val Phe Asn Asn Lys Asn<br>235                240               245 | 1314 |
|  agt ggc ttc tgg cac agc agc tta att gac cgg aac ctc att gat tat<br>Ser Gly Phe Trp His Ser Ser Leu Ile Asp Arg Asn Leu Ile Asp Tyr<br>250                255               260               265 | 1362 |
| ttt gtt ccc ttc ctc ccc ctg gaa tac aaa cac cta aaa atg tgt atc<br>Phe Val Pro Phe Leu Pro Leu Glu Tyr Lys His Leu Lys Met Cys Ile<br>               270               275               280 | 1410 |
| cga gtg gaa atg cag tcc cga ggc tat gaa att gat gaa gac att gta<br>Arg Val Glu Met Gln Ser Arg Gly Tyr Glu Ile Asp Glu Asp Ile Val<br>               285               290               295 | 1458 |
| agc aga gtg gct gag gag atg aca ttt ttc ccc aaa gag gag aga gtt<br>Ser Arg Val Ala Glu Glu Met Thr Phe Phe Pro Lys Glu Glu Arg Val<br>               300               305               310 | 1506 |
| ttc tca gat aaa ggc tgc aaa acg gtg ttc acc aag tta gat tat tac<br>Phe Ser Asp Lys Gly Cys Lys Thr Val Phe Thr Lys Leu Asp Tyr Tyr<br>315                320               325 | 1554 |
| tac gat gat tgacagtcat gattggcagc cggagtcact gcctggagtt<br>Tyr Asp Asp<br>330 | 1603 |
| ggaaagaaa caacactcag tccttccaca cttccacccc cagctccttt ccctggaaga | 1663 |
| ggaatccagt gaatgttcct gtttgatgtg acaggaattc tccctggcat tgtttccacc | 1723 |
| ccctggtgcc tgcaggccac ccagggacca cgggcgagga cgtgaagcct cccgaacacg | 1783 |
| cacagaagga aggagccagc tcccagccca ctcatcgcag ggctcatgat tttttacaaa | 1843 |
| ttatgtttta attccaagtg tttctgtttc aaggaaggat gaataagttt tattgaaaat | 1903 |
| gtggtaactt tatttaaaat gattttaac attatgagag actgctcaga ttctaagttg | 1963 |
| ttggccttgt gtgtgtgttt tttttaagt tctcatcatt attacataga ctgtgaagta | 2023 |
| tctttactgg aaatgagccc aagcacacat gcatggcatt tgttcctgaa caggagggca | 2083 |
| tccctgggga tgtggctgga gcatgagcca gctctgtccc aggatggtcc cagcggatgc | 2143 |
| tgccaggggc agtgaagtgt ttaggtgaag gacaagtagg taagaggacg ccttcaggca | 2203 |
| ccacagataa gcctgaaaca gcctctccaa gggttttcac cttagcaaca atgggagctg | 2263 |
| tgggagtgat tttggccaca ctgtcaacat ttgttagaac cagtcttttg aaagaaaagt | 2323 |
| atttccaact tgtcacttgc cagtcactcc gttttgcaaa aggtggccct tcactgtcca | 2383 |
| ttccaaatag cccacacgtg ctctctgctg gattctaaat tatgtgaatt ttgccatatt | 2443 |
| aaatcttcct catttatact attatttgtt acgttcaatc agaatcccg aaacctccta | 2503 |
| taaagcttag ctgccccttc tgaggatgct gagaacggtg tctttcttta taaatgcaaa | 2563 |
| tggctaccgt tttacaataa aattttgcat gtgc | 2597 |

<210> SEQ ID NO 2
<211> LENGTH: 332
<212> TYPE: PRT
<213> ORGANISM: Homo sapien

<400> SEQUENCE: 2

```
Met Lys Leu Gly Arg Ala Val Gly Leu Leu Leu Ala Pro Ser
 1               5                  10                  15

Val Val Gln Ala Val Glu Pro Ile Ser Leu Gly Leu Ala Leu Ala Gly
                20                  25                  30

Val Leu Thr Gly Tyr Ile Tyr Pro Arg Leu Tyr Cys Leu Phe Ala Glu
            35                  40                  45

Cys Cys Gly Gln Lys Arg Ser Leu Ser Arg Glu Ala Leu Gln Lys Asp
 50                  55                  60

Leu Asp Asp Asn Leu Phe Gly Gln His Leu Ala Lys Lys Ile Ile Leu
 65                  70                  75                  80

Asn Ala Val Phe Gly Phe Ile Asn Asn Pro Lys Pro Lys Lys Pro Leu
                85                  90                  95

Thr Leu Ser Leu His Gly Trp Thr Gly Thr Gly Lys Asn Phe Val Ser
            100                 105                 110

Lys Ile Ile Ala Glu Asn Ile Tyr Glu Gly Gly Leu Asn Ser Asp Tyr
        115                 120                 125

Val His Leu Phe Val Ala Thr Leu His Phe Pro His Ala Ser Asn Ile
130                 135                 140

Thr Leu Tyr Lys Asp Gln Leu Gln Leu Trp Ile Arg Gly Asn Val Ser
145                 150                 155                 160

Ala Cys Ala Arg Ser Ile Phe Ile Phe Asp Glu Met Asp Lys Met His
                165                 170                 175

Ala Gly Leu Ile Asp Ala Ile Lys Pro Phe Leu Asp Tyr Tyr Asp Leu
            180                 185                 190

Val Asp Gly Val Ser Tyr Gln Lys Ala Met Phe Ile Phe Leu Ser Asn
        195                 200                 205

Ala Gly Ala Glu Arg Ile Thr Asp Val Ala Leu Asp Phe Trp Arg Ser
210                 215                 220

Gly Lys Gln Arg Glu Asp Ile Lys Leu Lys Asp Ile Glu His Ala Leu
225                 230                 235                 240

Ser Val Ser Val Phe Asn Asn Lys Asn Ser Gly Phe Trp His Ser Ser
                245                 250                 255

Leu Ile Asp Arg Asn Leu Ile Asp Tyr Phe Val Pro Phe Leu Pro Leu
            260                 265                 270

Glu Tyr Lys His Leu Lys Met Cys Ile Arg Val Glu Met Gln Ser Arg
        275                 280                 285

Gly Tyr Glu Ile Asp Glu Asp Ile Val Ser Arg Val Ala Glu Glu Met
290                 295                 300

Thr Phe Phe Pro Lys Glu Glu Arg Val Phe Ser Asp Lys Gly Cys Lys
305                 310                 315                 320

Thr Val Phe Thr Lys Leu Asp Tyr Tyr Asp Asp
                325                 330
```

<210> SEQ ID NO 3
<211> LENGTH: 3568
<212> TYPE: DNA
<213> ORGANISM: Homo sapien
<220> FEATURE:
<221> NAME/KEY: CDS
<222> LOCATION: (994)...(1863)

<221> NAME/KEY: misc_feature
<222> LOCATION: (1)...(3568)
<223> OTHER INFORMATION: n = A, T, C or G

<400> SEQUENCE: 3

```
tgatccgcct gcctcggcct cccaaagtgc tgggattaca ggcgtgagcg ccgcgcccgg      60
ccagcctgag acagtttcgc tcttgtcgcc caggctggag tgcagtggca cgatctcggc     120
taactgcaac ctccgcctcc tgggttcaag agattctcct gcctcaacct ccgagtagct     180
gggattacag gcgyscgccr csmcrsccag cnttttttttt tttttttgag acagtttcgc    240
tcttgtcgcc aggctggagt gcagtgnnng anctcggcta actgcaactc cgcctcctgg     300
gttcaagaga ttctnctgcc tcaactcccg agtagctggg attataggng nccgcnacca     360
caccatctaa tttttttgtat ttttagtaga cacggggttt cgcacgttga gcaggctggt    420
ctcgaactcc tgacatcagg tgatccgccc gattcagctt cccaaagtgc tgggattaca    480
ggcgtgagca cggcgcccgg ccaaaaaaaa aatatttttt tttttttttt agatattttt    540
tcactcttgt tgcccaggct ggagtgaaat ggcgtgatct cggctcggcc tcccaaagtc    600
ctgggattac aggcgtgaca ccgngcccgg sccgaaaaaa twttttttaaa agaaaaaggg    660 aaacaaamag tctcctacac cttcgrccac tcccaagaac gatggsacss cctcctctyc    720 gncccctmacc aaccatggcc gncccnaagg gagtgggggcg ggtctgcggg gcggaagtga   780
cgsacgagag gaagtccgtc ctgcgcttgg ccgcggggcg cctggctcag tggcttctgc    840
gggcttcgag gagcgggatg ttgcgggctg ggtggctccg ggcgcggcgg cgctggcgct    900
gctgctggcg gcccgagtgg tggcggagtt cgagcccatc accgtgggcc tagccatcgg    960
```
gcaggtcggc catcaccggc tacctgtcct aca atg aca tct act gcc cgt tcg     1014  
                                                                                                        Met Thr Ser Thr Ala Arg Ser  
                                                                                                         1               5

```
ccg agt gct gcc ggc gag gag cgg ccg ctc aac gct tcg gct ctc aag     1062
Pro Ser Ala Ala Gly Glu Glu Arg Pro Leu Asn Ala Ser Ala Leu Lys
         10                  15                  20 ctg gat ttg gag gag aag ctg ttt gga cag cat cta gcc acg gaa gtg     1110
Leu Asp Leu Glu Glu Lys Leu Phe Gly Gln His Leu Ala Thr Glu Val
     25                  30                  35 att ttc aag gcg ctg act ggc ttc agg aac aac aaa aat ccc aag aaa     1158
Ile Phe Lys Ala Leu Thr Gly Phe Arg Asn Asn Lys Asn Pro Lys Lys
 40                  45                  50                  55 cca ctg acc ctt tcc tta cac ggc tgg gct ggc aca ggc aag aat ttt     1206
Pro Leu Thr Leu Ser Leu His Gly Trp Ala Gly Thr Gly Lys Asn Phe
                 60                  65                  70 gtc agt caa att gtg gct gaa aat ctt cac cca aaa ggt ctg aag agt     1254
Val Ser Gln Ile Val Ala Glu Asn Leu His Pro Lys Gly Leu Lys Ser
             75                  80                  85 aac ttt gtc cac ctg ttt gta tcg act ctg cac ttc cct cat gag cag     1302
Asn Phe Val His Leu Phe Val Ser Thr Leu His Phe Pro His Glu Gln
         90                  95                 100 aag ata aaa ctg tac cag gac cag tta cag aag tgg atc cgc ggt aat     1350
Lys Ile Lys Leu Tyr Gln Asp Gln Leu Gln Lys Trp Ile Arg Gly Asn
    105                 110                 115 gtg agt gca tgt gcg aac tct gtt ttc ata ttt gac gag atg gat aaa     1398
Val Ser Ala Cys Ala Asn Ser Val Phe Ile Phe Asp Glu Met Asp Lys
120                 125                 130                 135 ttg cac ccc ggg atc att gac gca atc aag ccg ttt cta gac tac tac     1446
Leu His Pro Gly Ile Ile Asp Ala Ile Lys Pro Phe Leu Asp Tyr Tyr
                140                 145                 150 gag cag gtt gac gga gtg tct tac cgc aaa gcc atc ttc atc ttt ctc     1494
Glu Gln Val Asp Gly Val Ser Tyr Arg Lys Ala Ile Phe Ile Phe Leu
```

| | | | | | | | | | | | | | |
|---|---|---|---|---|---|---|---|---|---|---|---|---|---|
| Glu | Gln | Val | Asp | Gly | Val | Ser | Tyr | Arg | Lys | Ala | Ile | Phe | Ile | Phe | Leu |
| | | | 155 | | | | 160 | | | | 165 | | |

| agc | aat | gca | ggc | ggg | gac | ctt | ata | act | aag | acg | gct | ctt | gac | ttt | tgg | 1542 |
|---|---|---|---|---|---|---|---|---|---|---|---|---|---|---|---|---|
| Ser | Asn | Ala | Gly | Gly | Asp | Leu | Ile | Thr | Lys | Thr | Ala | Leu | Asp | Phe | Trp | |
| | | 170 | | | | | 175 | | | | | 180 | | | | |

| cgg | gcc | gga | aga | aag | agg | gaa | gac | att | cag | ctg | aag | gac | ctg | gaa | cct | 1590 |
|---|---|---|---|---|---|---|---|---|---|---|---|---|---|---|---|---|
| Arg | Ala | Gly | Arg | Lys | Arg | Glu | Asp | Ile | Gln | Leu | Lys | Asp | Leu | Glu | Pro | |
| | 185 | | | | | 190 | | | | | 195 | | | | | |

| gta | ctg | tct | gtc | gga | gtc | ttc | aat | aat | aaa | cac | agt | ggc | ctg | tgg | cac | 1638 |
|---|---|---|---|---|---|---|---|---|---|---|---|---|---|---|---|---|
| Val | Leu | Ser | Val | Gly | Val | Phe | Asn | Asn | Lys | His | Ser | Gly | Leu | Trp | His | |
| 200 | | | | | 205 | | | | | 210 | | | | | 215 | |

| agt | gga | ctg | atc | gac | aaa | aac | ctc | att | gat | tac | ttt | atc | ccc | ttc | ctg | 1686 |
|---|---|---|---|---|---|---|---|---|---|---|---|---|---|---|---|---|
| Ser | Gly | Leu | Ile | Asp | Lys | Asn | Leu | Ile | Asp | Tyr | Phe | Ile | Pro | Phe | Leu | |
| | | | 220 | | | | | 225 | | | | | 230 | | | |

| cct | ttg | gag | tac | aga | cat | gtg | aaa | atg | tgt | gtg | agg | gcc | gag | atg | agg | 1734 |
|---|---|---|---|---|---|---|---|---|---|---|---|---|---|---|---|---|
| Pro | Leu | Glu | Tyr | Arg | His | Val | Lys | Met | Cys | Val | Arg | Ala | Glu | Met | Arg | |
| | | | 235 | | | | | 240 | | | | | 245 | | | |

| gcc | cgt | ggt | tct | gcc | ata | gat | gaa | gac | att | gtc | aca | aga | gtg | gca | gag | 1782 |
|---|---|---|---|---|---|---|---|---|---|---|---|---|---|---|---|---|
| Ala | Arg | Gly | Ser | Ala | Ile | Asp | Glu | Asp | Ile | Val | Thr | Arg | Val | Ala | Glu | |
| | 250 | | | | | 255 | | | | | 260 | | | | | |

| gaa | atg | acg | ttt | ttc | ccc | aga | gac | gag | aaa | atc | tac | tca | gac | aag | ggc | 1830 |
|---|---|---|---|---|---|---|---|---|---|---|---|---|---|---|---|---|
| Glu | Met | Thr | Phe | Phe | Pro | Arg | Asp | Glu | Lys | Ile | Tyr | Ser | Asp | Lys | Gly | |
| 265 | | | | | 270 | | | | | 275 | | | | | | |

| tgc | aag | act | gtg | cag | tcg | cgg | ctg | gat | ttc | cac | tgagctccta tccagatggg | 1883 |
|---|---|---|---|---|---|---|---|---|---|---|---|---|
| Cys | Lys | Thr | Val | Gln | Ser | Arg | Leu | Asp | Phe | His | | |
| 280 | | | | 285 | | | | | 290 | | | |

| | |
|---|---|
| gtaggagaca gctgggaggc tccgcacgcc agaggccttg cctttcagaa gaaccctgaa | 1943 |
| gaccgctttg ggttttgcc tgtttgcacc ttagactttt gggtatagaa tctttttttt | 2003 |
| gagaagaggt ctcactccgt catccaagct ggagtgcagt ggtgcaatcc tcaactcact | 2063 |
| gcaacctccg ctcccggttt gagtgattct catgcctcag cctcccgagt agctgggatt | 2123 |
| acaggcatga gccactgtgc ccagctggga tatagaatct aagagttgat tgtggaaaac | 2183 |
| acgtgaatct attgcgcgca tttgtcattt agcaagatgg cagcagtcca gctgttcttt | 2243 |
| gcagctggag atgaactttt aaaaatcccc ttcacactta atgtactgac cgagacagaa | 2303 |
| gtacctgaaa acagctgtgc atggcaggcc cggcaatagc ttctgaccca cagcacccgc | 2363 |
| gcctcagaag ctacggtcac aactaaagga gtccagggac ttgctgcagg ctggggggca | 2423 |
| ctgggtggtt ctcaccagca ggctgcgggg cactgtgttc tcattggcca aaaacatcct | 2483 |
| tttgctctgt ctcgttcttt acacagagtt cactgacttg aagtatactc agttaaaatc | 2543 |
| ggggctggag gtgcagacgg tgtctgaccg gaggatgtgg ccgtgcccgc cgagcactct | 2603 |
| tgatctgagc tgacctgtgt gtgtgtgtgg ggggggtgg ggccttcacc taagacctct | 2663 |
| gcagcagacc tggacagaca ggcccctccc gcctgtccat cgctctagct gctaatacag | 2723 |
| ccctggctgt ggaatccttc accgtctcag ctggtatcag ccccagcctg ccttggtgcc | 2783 |
| atatctcagc ttggatctct gctagagtcc ccccaaccat atatcataga gttgaatcac | 2843 |
| aatgagaccg ttggctttga atttgagtcg ttggttccca tggtgagatg cttgttaaga | 2903 |
| ctttatactt gggtcaatct ctcactttat tttgtagaac catttgaaat cctaggatgt | 2963 |
| gcttgttctg gaaggatgac atgggcccag actgaacaag tcagcttgat gatcttaaat | 3023 |
| gatggaagta taggacgttg cttatttaa aacaagggaa ggacacaaaa tggaatgact | 3083 |
| gccttagtcc tttctcagat actccttaaa acaattttt attgtttaaa tttgtggtaa | 3143 |
| tacatggtca caaccgtgga tcaaacaagg tcagtctaaa gtgcaggtc ctaggtgtga | 3203 |

```
cctgatacca ccacccttg tggcagcacc gggctggact gccctgatcc ctgggacgtg    3263
agacttagct tccagccagt gtgaatcatt gtatctgtct cataatcaca gcacagctgc    3323
agacacaaca acgtgcagca ttttttacat aaaaatatgg tagaattaat ttatgacatg    3383
gaaatgcctt acgtggtatc acacttagtc ttgaaaaaaa caccaaggtg acgtttaaaa    3443
tttttagtac atatcctcaa attggagcta agttatactt cttttataac cttttgggca    3503
tctggtcgag agaagacaag attttctcta tttacagtga ggcaataaat atgtttgcca    3563
cctttt                                                                3568
```

<210> SEQ ID NO 4
<211> LENGTH: 290
<212> TYPE: PRT
<213> ORGANISM: Homo sapien

<400> SEQUENCE: 4

```
Met Thr Ser Thr Ala Arg Ser Pro Ser Ala Gly Glu Glu Arg Pro
  1               5                  10                  15

Leu Asn Ala Ser Ala Leu Lys Leu Asp Leu Glu Glu Lys Leu Phe Gly
             20                  25                  30

Gln His Leu Ala Thr Glu Val Ile Phe Lys Ala Leu Thr Gly Phe Arg
         35                  40                  45

Asn Asn Lys Asn Pro Lys Lys Pro Leu Thr Leu Ser Leu His Gly Trp
 50                  55                  60

Ala Gly Thr Gly Lys Asn Phe Val Ser Gln Ile Val Ala Glu Asn Leu
 65                  70                  75                  80

His Pro Lys Gly Leu Lys Ser Asn Phe Val His Leu Phe Val Ser Thr
             85                  90                  95

Leu His Phe Pro His Glu Gln Lys Ile Lys Leu Tyr Gln Asp Gln Leu
            100                 105                 110

Gln Lys Trp Ile Arg Gly Asn Val Ser Ala Cys Ala Asn Ser Val Phe
            115                 120                 125

Ile Phe Asp Glu Met Asp Lys Leu His Pro Gly Ile Ile Asp Ala Ile
130                 135                 140

Lys Pro Phe Leu Asp Tyr Tyr Glu Gln Val Asp Gly Val Ser Tyr Arg
145                 150                 155                 160

Lys Ala Ile Phe Ile Phe Leu Ser Asn Ala Gly Gly Asp Leu Ile Thr
                165                 170                 175

Lys Thr Ala Leu Asp Phe Trp Arg Ala Gly Arg Lys Arg Glu Asp Ile
            180                 185                 190

Gln Leu Lys Asp Leu Glu Pro Val Leu Ser Val Gly Val Phe Asn Asn
            195                 200                 205

Lys His Ser Gly Leu Trp His Ser Gly Leu Ile Asp Lys Asn Leu Ile
        210                 215                 220

Asp Tyr Phe Ile Pro Phe Leu Pro Leu Glu Tyr Arg His Val Lys Met
225                 230                 235                 240

Cys Val Arg Ala Glu Met Arg Ala Arg Gly Ser Ala Ile Asp Glu Asp
                245                 250                 255

Ile Val Thr Arg Val Ala Glu Glu Met Thr Phe Phe Pro Arg Asp Glu
                260                 265                 270

Lys Ile Tyr Ser Asp Lys Gly Cys Lys Thr Val Gln Ser Arg Leu Asp
            275                 280                 285

Phe His
    290
```

```
<210> SEQ ID NO 5
<211> LENGTH: 2072
<212> TYPE: DNA
<213> ORGANISM: Homo sapien
<220> FEATURE:
<221> NAME/KEY: CDS
<222> LOCATION: (43)...(1038)

<400> SEQUENCE: 5
cgcggtcggc gcgagaacaa gcaggtggc gcgggtccgg gc atg aag ctg ggc                54
                                              Met Lys Leu Gly
                                                1 cgg gcc gtg ctg ggc ctg ctg ctg ctg gcg ccg tcc gtg gtg cag gcg            102
Arg Ala Val Leu Gly Leu Leu Leu Leu Ala Pro Ser Val Val Gln Ala
  5              10                  15                  20 gtg gag ccc atc agc ctg gga ctg gcc ctg gcc ggc gtc ctc acc ggc            150
Val Glu Pro Ile Ser Leu Gly Leu Ala Leu Ala Gly Val Leu Thr Gly
                25                  30                  35 tac atc tac ccg cgt ctc tac tgc ctc ttc gcc gag tgc tgc ggg cag            198
Tyr Ile Tyr Pro Arg Leu Tyr Cys Leu Phe Ala Glu Cys Cys Gly Gln
            40                  45                  50 aag cgg agc ctt agc cgg gag gca ctg cag aag gat ctg gac gac aac            246
Lys Arg Ser Leu Ser Arg Glu Ala Leu Gln Lys Asp Leu Asp Asp Asn
        55                  60                  65 ctc ttt gga cag cat ctt gca aag aaa atc atc tta aat gcc gtg ttt            294
Leu Phe Gly Gln His Leu Ala Lys Lys Ile Ile Leu Asn Ala Val Phe
    70                  75                  80 ggt ttc ata aac aac cca aag ccc aag aaa cct ctc acg ctc tcc ctg            342
Gly Phe Ile Asn Asn Pro Lys Pro Lys Lys Pro Leu Thr Leu Ser Leu
 85                  90                  95                 100 cac ggg tgg aca ggc acc ggc aaa aat ttc gtc agc aag atc atc gca            390
His Gly Trp Thr Gly Thr Gly Lys Asn Phe Val Ser Lys Ile Ile Ala
                105                 110                 115 gag aat att tac gag ggt ggt ctg aac agt gac tat gtc cac ctg ttt            438
Glu Asn Ile Tyr Glu Gly Gly Leu Asn Ser Asp Tyr Val His Leu Phe
            120                 125                 130 gtg gcc aca ttg cac ttt cca cat gct tca aac atc acc ttg tac aag            486
Val Ala Thr Leu His Phe Pro His Ala Ser Asn Ile Thr Leu Tyr Lys
        135                 140                 145 gat cag tta cag ttg tgg att cga ggc aac gtg agt gcc tgt gcg agg            534
Asp Gln Leu Gln Leu Trp Ile Arg Gly Asn Val Ser Ala Cys Ala Arg
    150                 155                 160 tcc atc ttc ata ttt gat gaa atg gat aag atg cat gca ggc ctc ata            582
Ser Ile Phe Ile Phe Asp Glu Met Asp Lys Met His Ala Gly Leu Ile
165                 170                 175                 180 gat gcc atc aag cct ttc ctc gac tat tat gac ctg gtg gat ggg gtc            630
Asp Ala Ile Lys Pro Phe Leu Asp Tyr Tyr Asp Leu Val Asp Gly Val
                185                 190                 195 tcc tac cag aaa gcc atg ttc ata ttt ctc agc aat gct gga gca gaa            678
Ser Tyr Gln Lys Ala Met Phe Ile Phe Leu Ser Asn Ala Gly Ala Glu
            200                 205                 210 agg atc aca gat gtg gct ttg gat ttc tgg agg agt gga aag cag agg            726
Arg Ile Thr Asp Val Ala Leu Asp Phe Trp Arg Ser Gly Lys Gln Arg
        215                 220                 225 gaa gac atc aag ctc aaa gac att gaa cac gcg ttg tct gtg tcg gtt            774
Glu Asp Ile Lys Leu Lys Asp Ile Glu His Ala Leu Ser Val Ser Val
    230                 235                 240 ttc aat aac aag aac agt ggc ttc tgg cac agc agc tta att gac cgg            822
Phe Asn Asn Lys Asn Ser Gly Phe Trp His Ser Ser Leu Ile Asp Arg
245                 250                 255                 260
```

```
aac ctc att gat tat ttt gtt ccc ttc ctc ccc ctg gaa tac aaa cac      870
Asn Leu Ile Asp Tyr Phe Val Pro Phe Leu Pro Leu Glu Tyr Lys His
                265                 270                 275 cta aaa atg tgt atc cga gtg gaa atg cag tcc cga ggc tat gaa att      918
Leu Lys Met Cys Ile Arg Val Glu Met Gln Ser Arg Gly Tyr Glu Ile
            280                 285                 290 gat gaa gac att gta agc aga gtg gct gag gag atg aca ttt ttc ccc      966
Asp Glu Asp Ile Val Ser Arg Val Ala Glu Glu Met Thr Phe Phe Pro
                295                 300                 305 aaa gag gag aga gtt ttc tca gat aaa ggc tgc aaa acg gtg ttc acc     1014
Lys Glu Glu Arg Val Phe Ser Asp Lys Gly Cys Lys Thr Val Phe Thr
            310                 315                 320 aag tta gat tat tac tac gat gat tgacagtcat gattggcagc ggagtcact     1068
Lys Leu Asp Tyr Tyr Tyr Asp Asp
325                 330 gcctggagtt ggaaaagaaa caacactcag tccttccaca cttccacccc cagctccttt   1128
ccctggaaga ggaatccagt gaatgttcct gtttgatgtg acaggaattc tccctggcat   1188
tgtttccacc ccctggtgcc tgcaggccac ccagggacca cgggcgagga cgtgaagcct   1248
cccgaacacg cacagaagga aggagccagc tcccagccca ctcatcgcag ggctcatgat   1308
tttttacaaa ttatgtttta attccaagtg tttctgtttc aaggaaggat gaataagttt   1368
tattgaaaat gtggtaactt tatttaaaat gatttttaac attatgagag actgctcaga   1428
ttctaagttg ttggccttgt gtgtgtgttt tttttttaagt tctcatcatt attacataga   1488
ctgtgaagta tctttactgg aaatgagccc aagcacacat gcatggcatt tgttcctgaa   1548
caggagggca tccctgggga tgtggctgga gcatgagcca gctctgtccc aggatggtcc   1608
cagcggatgc tgccagggggc agtgaagtgt taggtgaag acaagtagg taagaggacg    1668 ccttcaggca ccacagataa gcctgaaaca gcctctccaa gggttttcac cttagcaaca   1728
atgggagctg tgggagtgat tttgccaca ctgtcaacat tgttagaac cagtcttttg     1788 aaagaaaagt atttccaact tgtcacttgc cagtcactcc gttttgcaaa aggtggccct   1848
tcactgtcca ttccaaatag cccacacgtg ctctctgctg gattctaaat tatgtgaatt   1908
ttgccatatt aaatcttcct catttatact attatttgtt acgttcaatc agaatccccg   1968
aaacctccta taaagcttag ctgccccttc tgaggatgct gagaacggtg tctttctttta  2028 taaatgcaaa tggctaccgt tttacaataa aattttgcat gtgc                    2072
```

<210> SEQ ID NO 6
<211> LENGTH: 332
<212> TYPE: PRT
<213> ORGANISM: Homo sapien

<400> SEQUENCE: 6

```
Met Lys Leu Gly Arg Ala Val Leu Gly Leu Leu Leu Leu Ala Pro Ser
 1               5                  10                  15

Val Val Gln Ala Val Glu Pro Ile Ser Leu Gly Leu Ala Leu Ala Gly
            20                  25                  30

Val Leu Thr Gly Tyr Ile Tyr Pro Arg Leu Tyr Cys Leu Phe Ala Glu
        35                  40                  45

Cys Cys Gly Gln Lys Arg Ser Leu Ser Arg Glu Ala Leu Gln Lys Asp
    50                  55                  60

Leu Asp Asp Asn Leu Phe Gly Gln His Leu Ala Lys Lys Ile Ile Leu
65                  70                  75                  80

Asn Ala Val Phe Gly Phe Ile Asn Asn Pro Lys Pro Lys Lys Pro Leu
                85                  90                  95
```

```
Thr Leu Ser Leu His Gly Trp Thr Gly Thr Gly Lys Asn Phe Val Ser
            100                 105                 110
Lys Ile Ile Ala Glu Asn Ile Tyr Glu Gly Leu Asn Ser Asp Tyr
            115                 120                 125
Val His Leu Phe Val Ala Thr Leu His Phe Pro His Ala Ser Asn Ile
    130                 135                 140
Thr Leu Tyr Lys Asp Gln Leu Gln Leu Trp Ile Arg Gly Asn Val Ser
145                 150                 155                 160
Ala Cys Ala Arg Ser Ile Phe Ile Phe Asp Glu Met Asp Lys Met His
                165                 170                 175
Ala Gly Leu Ile Asp Ala Ile Lys Pro Phe Leu Asp Tyr Tyr Asp Leu
            180                 185                 190
Val Asp Gly Val Ser Tyr Gln Lys Ala Met Phe Ile Phe Leu Ser Asn
            195                 200                 205
Ala Gly Ala Glu Arg Ile Thr Asp Val Ala Leu Asp Phe Trp Arg Ser
    210                 215                 220
Gly Lys Gln Arg Glu Asp Ile Lys Leu Lys Asp Ile Glu His Ala Leu
225                 230                 235                 240
Ser Val Ser Val Phe Asn Asn Lys Asn Ser Gly Phe Trp His Ser Ser
                245                 250                 255
Leu Ile Asp Arg Asn Leu Ile Asp Tyr Phe Val Pro Phe Leu Pro Leu
            260                 265                 270
Glu Tyr Lys His Leu Lys Met Cys Ile Arg Val Glu Met Gln Ser Arg
            275                 280                 285
Gly Tyr Glu Ile Asp Glu Asp Ile Val Ser Arg Val Ala Glu Glu Met
    290                 295                 300
Thr Phe Phe Pro Lys Glu Glu Arg Val Phe Ser Asp Lys Gly Cys Lys
305                 310                 315                 320
Thr Val Phe Thr Lys Leu Asp Tyr Tyr Tyr Asp Asp
                325                 330
```

<210> SEQ ID NO 7
<211> LENGTH: 2504
<212> TYPE: DNA
<213> ORGANISM: Homo sapien
<220> FEATURE:
<221> NAME/KEY: CDS
<222> LOCATION: (2)...(799)

<400> SEQUENCE: 7

```
g gat ttg gag gag aag ctg ttt gga cag cat cta gcc acg gaa gtg att      49
  Asp Leu Glu Glu Lys Leu Phe Gly Gln His Leu Ala Thr Glu Val Ile
  1               5                   10                  15 ttc aag gcg ctg act ggc ttc agg aac aac aaa aat ccc aag aaa cca      97
Phe Lys Ala Leu Thr Gly Phe Arg Asn Asn Lys Asn Pro Lys Lys Pro
                20                  25                  30 ctg acc ctt tcc tta cac ggc tgg gct ggc aca ggc aag aat ttt gtc     145
Leu Thr Leu Ser Leu His Gly Trp Ala Gly Thr Gly Lys Asn Phe Val
            35                  40                  45 agt caa att gtg gct gaa aat ctt cac cca aaa ggt ctg aag agt aac     193
Ser Gln Ile Val Ala Glu Asn Leu His Pro Lys Gly Leu Lys Ser Asn
    50                  55                  60 ttt gtc cac ctg ttt gta tcg act ctg cac ttc cct cat gag cag aag     241
Phe Val His Leu Phe Val Ser Thr Leu His Phe Pro His Glu Gln Lys
65                  70                  75                  80 ata aaa ctg tac cag gac cag tta cag aag tgg atc cgc ggt aat gtg     289
Ile Lys Leu Tyr Gln Asp Gln Leu Gln Lys Trp Ile Arg Gly Asn Val
```

-continued

|  | 85 | 90 | 95 |  |
|---|---|---|---|---|
| agt gca tgt gcg aac tct gtt ttc ata ttt gac gag atg gat aaa ttg<br>Ser Ala Cys Ala Asn Ser Val Phe Ile Phe Asp Glu Met Asp Lys Leu<br>100 105 110 | | | | 337 |
| cac ccc ggg atc att gac gca atc aag ccg ttt cta gac tac tac gag<br>His Pro Gly Ile Ile Asp Ala Ile Lys Pro Phe Leu Asp Tyr Tyr Glu<br>115 120 125 | | | | 385 |
| cag gtt gac gga gtg tct tac cgc aaa gcc atc ttc atc ttt ctc agc<br>Gln Val Asp Gly Val Ser Tyr Arg Lys Ala Ile Phe Ile Phe Leu Ser<br>130 135 140 | | | | 433 |
| aat gca ggc ggg gac ctt ata act aag acg gct ctt gac ttt tgg cgg<br>Asn Ala Gly Gly Asp Leu Ile Thr Lys Thr Ala Leu Asp Phe Trp Arg<br>145 150 155 160 | | | | 481 |
| gcc gga aga aag agg gaa gac att cag ctg aag gac ctg gaa cct gta<br>Ala Gly Arg Lys Arg Glu Asp Ile Gln Leu Lys Asp Leu Glu Pro Val<br>165 170 175 | | | | 529 |
| ctg tct gtc gga gtc ttc aat aat aaa cac agt ggc ctg tgg cac agt<br>Leu Ser Val Gly Val Phe Asn Asn Lys His Ser Gly Leu Trp His Ser<br>180 185 190 | | | | 577 |
| gga ctg atc gac aaa aac ctc att gat tac ttt atc ccc ttc ctg cct<br>Gly Leu Ile Asp Lys Asn Leu Ile Asp Tyr Phe Ile Pro Phe Leu Pro<br>195 200 205 | | | | 625 |
| ttg gag tac aga cat gtg aaa atg tgt gtg agg gcc gag atg agg gcc<br>Leu Glu Tyr Arg His Val Lys Met Cys Val Arg Ala Glu Met Arg Ala<br>210 215 220 | | | | 673 |
| cgt ggt tct gcc ata gat gaa gac att gtc aca aga gtg gca gag gaa<br>Arg Gly Ser Ala Ile Asp Glu Asp Ile Val Thr Arg Val Ala Glu Glu<br>225 230 235 240 | | | | 721 |
| atg acg ttt ttc ccc aga gac gag aaa atc tac tca gac aag ggc tgc<br>Met Thr Phe Phe Pro Arg Asp Glu Lys Ile Tyr Ser Asp Lys Gly Cys<br>245 250 255 | | | | 769 |
| aag act gtg cag tcg cgg ctg gat ttc cac tgagctccta tccagatggg<br>Lys Thr Val Gln Ser Arg Leu Asp Phe His<br>260 265 | | | | 819 |
| gtaggagaca gctgggaggc tccgcacgcc agaggccttg cctttcagaa gaaccctgaa | | | | 879 |
| gaccgctttg gggttttgcc tgtttgcacc ttagacttttt gggtatagaa tctttttttt | | | | 939 |
| gagaagaggt ctcactccgt catccaagct ggagtgcagt ggtgcaatcc tcaactcact | | | | 999 |
| gcaacctccg ctcccggttt gagtgattct catgcctcag cctcccgagt agctgggatt | | | | 1059 |
| acaggcatga gccactgtgc ccagctggga tatagaatct aagagttgat tgtggaaaac | | | | 1119 |
| acgtgaatct attgcgcgca tttgtcattt agcaagatgg cagcagtcca gctgttcttt | | | | 1179 |
| gcagctggag atgaactttt aaaaatcccc ttcacactta atgtactgac cgagacagaa | | | | 1239 |
| gtacctgaaa acagctgtgc atggcaggcc cggcaatagc ttctgaccca cagcacccgc | | | | 1299 |
| gcctcagaag ctacggtcac aactaaagga gtccagggac ttgctgcagg ctgggggggca | | | | 1359 |
| ctgggtggtt ctcaccagca ggctgcgggg cactgtgttc tcattggcca aaaacatcct | | | | 1419 |
| tttgctctgt ctcgttcttt acacagagtt cactgacttg aagtatactc agttaaaatc | | | | 1479 |
| ggggctggag gtgcagacgg tgtctgaccg gaggatgtgg ccgtgcccgc cgagcactct | | | | 1539 |
| tgatctgagc tgacctgtgt gtgtgtgtgg ggggggtgg ggccttcacc taagacctct | | | | 1599 |
| gcagcagacc tggacagaca gggcccctccc gcctgtccat cgctctagct gctaatacag | | | | 1659 |
| ccctggctgt ggaatccttc accgtctcag ctggtatcag cccagcctg ccttggtgcc | | | | 1719 |
| atatctcagc ttgatctct gctagagtcc cccaaccat atatcataga gttgaatcac | | | | 1779 |
| aatgagaccg ttggctttga atttgagtcg ttggttccca tggtgagatg cttgttaaga | | | | 1839 |

```
ctttatactt gggtcaatct ctcactttat tttgtagaac catttgaaat cctaggatgt    1899
gcttgttctg gaaggatgac atgggcccag actgaacaag tcagcttgat gatcttaaat    1959
gatggaagta taggacgttg cttattttaa acaagggaa ggacacaaaa tggaatgact     2019
gccttagtcc tttctcagat actccttaaa acaattttt attgtttaaa tttgtggtaa     2079
tacatggtca caaccgtgga tcaaacaagg tcagtctaaa gtggcaggtc ctaggtgtga    2139
cctgatacca ccacccttg tggcagcacc gggctggact gccctgatcc ctgggacgtg     2199
agacttagct tccagccagt gtgaatcatt gtatctgtct cataatcaca gcacagctgc    2259
agacacaaca acgtgcagca ttttttacat aaaaatatgg tagaattaat ttatgacatg    2319
gaaatgcctt acgtggtatc acacttagtc ttgaaaaaaa caccaaggtg acgtttaaaa    2379
tttttagtac atatcctcaa attggagcta agttatactt cttttataac cttttgggca    2439
tctggtcgag agaagacaag attttctcta tttacagtga ggcaataaat atgtttgcca    2499
cctttt                                                               2504
```

<210> SEQ ID NO 8
<211> LENGTH: 266
<212> TYPE: PRT
<213> ORGANISM: Homo sapien

<400> SEQUENCE: 8

```
Asp Leu Glu Glu Lys Leu Phe Gly Gln His Leu Ala Thr Glu Val Ile
 1               5                  10                  15

Phe Lys Ala Leu Thr Gly Phe Arg Asn Asn Lys Asn Pro Lys Lys Pro
            20                  25                  30

Leu Thr Leu Ser Leu His Gly Trp Ala Gly Thr Gly Lys Asn Phe Val
        35                  40                  45

Ser Gln Ile Val Ala Glu Asn Leu His Pro Lys Gly Leu Lys Ser Asn
    50                  55                  60

Phe Val His Leu Phe Val Ser Thr Leu His Phe Pro His Glu Gln Lys
65                  70                  75                  80

Ile Lys Leu Tyr Gln Asp Gln Leu Gln Lys Trp Ile Arg Gly Asn Val
                85                  90                  95

Ser Ala Cys Ala Asn Ser Val Phe Ile Phe Asp Glu Met Asp Lys Leu
            100                 105                 110

His Pro Gly Ile Ile Asp Ala Ile Lys Pro Phe Leu Asp Tyr Tyr Glu
        115                 120                 125

Gln Val Asp Gly Val Ser Tyr Arg Lys Ala Ile Phe Ile Phe Leu Ser
    130                 135                 140

Asn Ala Gly Gly Asp Leu Ile Thr Lys Thr Ala Leu Asp Phe Trp Arg
145                 150                 155                 160

Ala Gly Arg Lys Arg Glu Asp Ile Gln Leu Lys Asp Leu Glu Pro Val
                165                 170                 175

Leu Ser Val Gly Val Phe Asn Asn Lys His Ser Gly Leu Trp His Ser
            180                 185                 190

Gly Leu Ile Asp Lys Asn Leu Ile Asp Tyr Phe Ile Pro Phe Leu Pro
        195                 200                 205

Leu Glu Tyr Arg His Val Lys Met Cys Val Arg Ala Glu Met Arg Ala
    210                 215                 220

Arg Gly Ser Ala Ile Asp Glu Asp Ile Val Thr Arg Val Ala Glu Glu
225                 230                 235                 240

Met Thr Phe Phe Pro Arg Asp Glu Lys Ile Tyr Ser Asp Lys Gly Cys
```

245                 250                 255
Lys Thr Val Gln Ser Arg Leu Asp Phe His
            260                 265

<210> SEQ ID NO 9
<211> LENGTH: 332
<212> TYPE: PRT
<213> ORGANISM: Homo sapien

<400> SEQUENCE: 9

Met Lys Leu Gly Arg Ala Val Leu Gly Leu Leu Leu Leu Ala Pro Ser
 1               5                  10                  15

Val Val Gln Ala Val Glu Pro Ile Ser Leu Gly Leu Ala Leu Ala Gly
            20                  25                  30

Val Leu Thr Gly Tyr Ile Tyr Pro Arg Leu Tyr Cys Leu Phe Ala Glu
        35                  40                  45

Cys Cys Gly Gln Lys Arg Ser Leu Ser Arg Glu Ala Leu Gln Lys Asp
    50                  55                  60

Leu Asp Asp Asn Leu Phe Gly Gln His Leu Ala Lys Lys Ile Ile Leu
65                  70                  75                  80

Asn Ala Val Phe Gly Phe Ile Asn Asn Pro Lys Pro Lys Lys Pro Leu
                85                  90                  95

Thr Leu Ser Leu His Gly Trp Thr Gly Thr Gly Lys Asn Phe Val Ser
            100                 105                 110

Lys Ile Ile Ala Glu Asn Ile Tyr Glu Gly Gly Leu Asn Ser Asp Tyr
        115                 120                 125

Val His Leu Phe Val Ala Thr Leu His Phe Pro His Ala Ser Asn Ile
    130                 135                 140

Thr Leu Tyr Lys Asp Gln Leu Gln Leu Trp Ile Arg Gly Asn Val Ser
145                 150                 155                 160

Ala Cys Ala Arg Ser Ile Phe Ile Phe Asp Glu Met Asp Lys Met His
                165                 170                 175

Ala Gly Leu Ile Asp Ala Ile Lys Pro Phe Leu Asp Tyr Tyr Asp Leu
            180                 185                 190

Val Asp Gly Val Ser Tyr Gln Lys Ala Met Phe Ile Phe Leu Ser Asn
        195                 200                 205

Ala Gly Ala Glu Arg Ile Thr Asp Val Ala Leu Asp Phe Trp Arg Ser
    210                 215                 220

Gly Lys Gln Arg Glu Asp Ile Lys Leu Lys Asp Ile Glu His Ala Leu
225                 230                 235                 240

Ser Val Ser Val Phe Asn Asn Lys Asn Ser Gly Phe Trp His Ser Ser
                245                 250                 255

Leu Ile Asp Arg Asn Leu Ile Asp Tyr Phe Val Pro Phe Leu Pro Leu
            260                 265                 270

Glu Tyr Lys His Leu Lys Met Cys Ile Arg Val Glu Met Gln Ser Arg
        275                 280                 285

Gly Tyr Glu Ile Asp Glu Asp Ile Val Ser Arg Val Ala Glu Glu Met
    290                 295                 300

Thr Phe Phe Pro Lys Glu Glu Pro Val Phe Ser Asp Lys Gly Cys Lys
305                 310                 315                 320

Thr Val Phe Thr Lys Leu Asp Tyr Tyr Asp Asp
                325                 330

<210> SEQ ID NO 10
<211> LENGTH: 267

```
<212> TYPE: PRT
<213> ORGANISM: Homo sapien
<220> FEATURE:
<221> NAME/KEY: VARIANT
<222> LOCATION: (1)...(267)
<223> OTHER INFORMATION: Xaa = any amino acid

<400> SEQUENCE: 10
```

Leu Asp Leu Glu Glu Lys Leu Phe Gly Gln His Leu Ala Thr Glu Val
 1               5                  10                  15

Ile Phe Lys Ala Leu Thr Gly Phe Arg Asn Asn Lys Asn Pro Lys Lys
             20                  25                  30

Pro Leu Thr Leu Ser Leu His Gly Trp Ala Gly Thr Gly Lys Asn Phe
         35                  40                  45

Val Ser Gln Ile Val Ala Glu Asn Leu His Pro Lys Gly Leu Lys Ser
 50                  55                  60

Asn Phe Val His Leu Phe Val Ser Thr Leu His Phe Pro His Glu Gln
65                  70                  75                  80

Lys Ile Lys Leu Tyr Gln Asp Gln Leu Gln Lys Trp Ile Arg Gly Asn
                85                  90                  95

Val Ser Ala Cys Ala Asn Ser Val Phe Ile Phe Asp Glu Met Asp Lys
            100                 105                 110

Leu His Pro Gly Ile Ile Asp Ala Ile Lys Pro Phe Leu Asp Tyr Tyr
        115                 120                 125

Glu Gln Val Asp Gly Val Ser Tyr Xaa Lys Ala Ile Phe Ile Phe Leu
130                 135                 140

Ser Asn Ala Gly Gly Asp Leu Ile Thr Lys Thr Ala Leu Asp Phe Trp
145                 150                 155                 160

Arg Ala Gly Arg Lys Arg Glu Asp Ile Gln Leu Lys Asp Leu Glu Pro
                165                 170                 175

Val Leu Ser Val Gly Val Phe Asn Asn Lys His Ser Gly Leu Trp His
            180                 185                 190

Ser Gly Leu Ile Asp Lys Asn Leu Ile Asp Tyr Phe Ile Pro Phe Leu
        195                 200                 205

Pro Leu Glu Tyr Arg His Val Lys Met Cys Val Arg Ala Glu Met Arg
    210                 215                 220

Ala Arg Gly Ser Ala Ile Asp Glu Asp Ile Val Thr Arg Val Ala Glu
225                 230                 235                 240

Glu Met Thr Phe Phe Pro Arg Asp Glu Lys Ile Tyr Ser Asp Lys Gln
                245                 250                 255

Cys Lys Thr Val Gln Ser Arg Leu Asp Phe His
            260                 265

```
<210> SEQ ID NO 11
<211> LENGTH: 334
<212> TYPE: PRT
<213> ORGANISM: C. elegans

<400> SEQUENCE: 11
```

Met Trp Met Lys Leu Asp Tyr Val Leu Leu Leu Phe His Leu Cys
 1               5                  10                  15

Phe Val Asn Thr Glu Leu Ile Ser Val Ile Thr Gly Lys Ile Lys Asp
             20                  25                  30

Ser Gly Thr Thr Ile Ala Ile Ser Ala Gly Ala Phe Trp Gly Leu Lys
         35                  40                  45

Asp Arg Leu Lys Cys Tyr Leu Tyr Glu Cys Cys His Glu Pro Asp Val
 50                  55                  60

```
Asn Phe Asn Tyr His Thr Leu Asp Ala Asp Ile Ala Asn Leu Leu Phe
 65                  70                  75                  80

Gly Gln His Leu Val Lys Asp Val Val Asn Ser Ile Lys Ser His
                 85                  90                  95

Trp Tyr Asn Glu Asn Pro Arg Lys Pro Leu Val Leu Ser Phe His Gly
            100                 105                 110

Tyr Thr Gly Ser Gly Lys Asn Tyr Val Ala Glu Ile Ile Ala Asn Asn
        115                 120                 125

Thr Phe Arg Leu Gly Leu Arg Ser Thr Phe Val Gln His Ile Val Ala
    130                 135                 140

Thr Asn Asp Phe Pro Asp Lys Asn Lys Leu Glu Glu Tyr Gln Val Glu
145                 150                 155                 160

Leu Arg Asn Arg Ile Leu Thr Thr Val Gln Lys Cys Gln Arg Ser Ile
                165                 170                 175

Phe Ile Phe Asp Glu Ala Asp Lys Leu Pro Glu Gln Leu Leu Gly Ala
            180                 185                 190

Ile Lys Pro Phe Leu Asp Tyr Tyr Ser Thr Ile Ser Gly Val Asp Phe
        195                 200                 205

Arg Arg Ser Ile Phe Ile Leu Leu Ser Asn Lys Gly Gly Glu Ile
    210                 215                 220

Ala Arg Ile Thr Lys Glu Gln Tyr Glu Ser Gly Tyr Pro Arg Glu Gln
225                 230                 235                 240

Leu Arg Leu Glu Ala Phe Glu Arg Glu Leu Met Asn Phe Ser Tyr Asn
                245                 250                 255

Glu Lys Gly Gly Leu Gln Met Ser Glu Leu Ile Ser Asn His Leu Ile
            260                 265                 270

Asp His Phe Val Pro Phe Leu Pro Leu Gln Arg Glu His Val Arg Ser
        275                 280                 285

Cys Val Gly Ala Tyr Leu Arg Lys Arg Gly Arg Gly Asp Leu Val Ser
    290                 295                 300

Asn Val Asp Phe Val Glu Arg Val Leu Asn Ser Leu Gln Tyr Phe Pro
305                 310                 315                 320

Glu Ser Ser Lys Ala Phe Ser Ser Gly Cys Lys Arg Val
                325                 330

<210> SEQ ID NO 12
<211> LENGTH: 268
<212> TYPE: PRT
<213> ORGANISM: Homo sapien

<400> SEQUENCE: 12

Leu Glu Cys Asp Leu Ala Gln His Leu Ala Gly Gln His Leu Ala Lys
 1               5                  10                  15

Ala Leu Val Val Lys Ser Leu Lys Ala Phe Val Gln Asp Pro Ala Pro
                20                  25                  30

Ser Lys Pro Leu Val Leu Ser Leu His Gly Trp Thr Gly Thr Gly Lys
            35                  40                  45

Ser Tyr Val Ser Ser Leu Leu Ala Gln His Leu Phe Arg Asp Gly Leu
        50                  55                  60

Arg Ser Pro His Val His His Phe Ser Pro Ile Ile His Phe Pro His
 65                  70                  75                  80

Pro Ser Arg Thr Glu Gln Tyr Lys Lys Glu Leu Lys Ser Trp Val Gln
                85                  90                  95

Gly Asn Thr Ala Cys Glu Arg Ser Leu Phe Leu Phe Asp Glu Met Asp
```

```
                    100                 105                 110
Lys Leu Pro Pro Gly Leu Met Glu Val Leu Gln Pro Phe Leu Gly Pro
            115                 120                 125

Ser Trp Val Val Tyr Gly Thr Asn Tyr Arg Lys Ala Ile Phe Ile Phe
    130                 135                 140

Ile Ser Asn Ala Gly Gly Glu Cys Ile Asn Gln Val Ala Leu Glu Ala
145                 150                 155                 160

Trp Arg Thr Asn Arg Asp Arg Glu Glu Ile Ser Leu Gln Glu Val Glu
                165                 170                 175

Pro Val Ile Ser Arg Ala Val Met Asp Asn Pro Gln His Gly Phe Trp
            180                 185                 190

Arg Ser Gly Ile Met Glu Glu His Leu Leu Asp Ala Val Val Pro Phe
            195                 200                 205

Leu Pro Leu Gln Arg His His Val Arg His Cys Val Leu Asn Glu Leu
            210                 215                 220

Ala Gln Leu Gly Leu Glu Pro Ala Arg Arg Trp Phe Arg Arg Cys Trp
225                 230                 235                 240

Thr Asp Thr Tyr Phe Pro Glu Val Glu Gln Leu Phe Ser Ser Asn Gly
                245                 250                 255

Cys Lys Thr Val Ala Ser Arg Leu Thr Phe Phe Leu
            260                 265
```

<210> SEQ ID NO 13
<211> LENGTH: 177
<212> TYPE: PRT
<213> ORGANISM: Murine
<220> FEATURE:
<221> NAME/KEY: VARIANT
<222> LOCATION: (1)...(177)
<223> OTHER INFORMATION: Xaa = Any Amino Acid

<400> SEQUENCE: 13

```
Ala Ala Ala Leu His Gln Thr Leu Phe Ile Phe Asp Glu Ala Glu Lys
1               5                   10                  15

Leu His Pro Gly Leu Leu Glu Val Leu Gly Pro His Leu Glu Arg Arg
            20                  25                  30

Ala Pro Glu Xaa Xaa Gly Leu Ser Leu Xaa Trp Thr Ile Phe Leu Phe
            35                  40                  45

Leu Ser Asn Leu Arg Gly Asp Ile Ile Asn Glu Val Val Leu Lys Leu
    50                  55                  60

Leu Lys Ala Gly Trp Ser Arg Glu Glu Ile Thr Met Glu His Leu Glu
65                  70                  75                  80

Pro His Leu Gln Ala Glu Ile Val Asp Asp His Arg Gln Trp Leu Trp
                85                  90                  95

His Ser Arg Leu Val Lys Glu Asn Leu Ile Asp Tyr Phe Ile Pro Phe
            100                 105                 110

Leu Pro Leu Glu Tyr Arg His Val Arg Leu Cys Ala Arg Asp Ala Phe
            115                 120                 125

Leu Ser Gln Glu Leu Leu Tyr Lys Glu Thr Leu Asp Glu Ile Ala
    130                 135                 140

Gln Met Met Val Tyr Val Pro Lys Glu Gln Leu Phe Ser Ser Gln
145                 150                 155                 160

Gly Cys Lys Ser Ile Xaa Gln Arg Ile Lys Leu Leu Pro Val Met Xaa
                165                 170                 175

Gly
```

```
<210> SEQ ID NO 14
<211> LENGTH: 214
<212> TYPE: PRT
<213> ORGANISM: Murine

<400> SEQUENCE: 14

Glu Glu His Pro Leu Val Phe Leu Phe Leu Gly Ser Ser Gly Ile Gly
 1               5                  10                  15

Lys Thr Glu Leu Ala Lys Gln Thr Ala Lys Tyr Met His Lys Asp Ala
                20                  25                  30

Lys Lys Gly Phe Ile Arg Leu Asp Met Ser Glu Phe Gln Glu Arg His
            35                  40                  45

Glu Val Ala Lys Phe Ile Gly Ser Pro Arg Gly Tyr Ile Gly His Glu
        50                  55                  60

Glu Gly Gly Gln Leu Thr Lys Lys Leu Lys Gln Cys Pro Asn Ala Val
65                  70                  75                  80

Val Leu Phe Asp Glu Val Asp Lys Ala His Pro Asp Val Leu Thr Ile
                85                  90                  95

Met Leu Gln Leu Phe Asp Glu Gly Arg Leu Thr Asp Gly Lys Gly Lys
            100                 105                 110

Thr Ile Asp Cys Lys Asp Ala Ile Phe Ile Met Thr Ser Asn Val Ala
        115                 120                 125

Ser Asp Glu Ile Ala Gln His Ala Leu Gln Leu Arg Gln Glu Ala Leu
130                 135                 140

Glu Met Ser Arg Asn Arg Ile Ala Glu Asn Leu Gly Asp Val Gln Met
145                 150                 155                 160

Ser Asp Lys Ile Thr Ile Ser Lys Asn Phe Lys Glu Asn Val Ile Arg
                165                 170                 175

Pro Ile Leu Lys Ala His Phe Arg Arg Asp Glu Phe Leu Gly Arg Ile
            180                 185                 190

Asn Glu Ile Val Tyr Phe Leu Pro Phe Cys His Ser Glu Leu Ile Gln
        195                 200                 205

Leu Val Asn Lys Glu Leu
    210

<210> SEQ ID NO 15
<211> LENGTH: 185
<212> TYPE: PRT
<213> ORGANISM: Unknown
<220> FEATURE:
<223> OTHER INFORMATION: Soybean

<400> SEQUENCE: 15

Pro Gln Gln Pro Thr Gly Ser Phe Leu Phe Leu Gly Pro Thr Gly Val
 1               5                  10                  15

Gly Lys Thr Glu Leu Ala Lys Ala Leu Ala Glu Gln Leu Phe Asp Asn
                20                  25                  30

Glu Asn Gln Leu Val Arg Ile Asp Met Ser Glu Tyr Met Glu Gln His
            35                  40                  45

Ser Val Ser Arg Leu Ile Gly Ala Pro Pro Gly Tyr Val Gly His Glu
        50                  55                  60

Glu Gly Gly Gln Leu Thr Glu Ala Val Arg Arg Arg Pro Tyr Ser Val
65                  70                  75                  80

Val Leu Phe Asp Glu Val Glu Lys Ala His Thr Ser Val Phe Asn Ile
                85                  90                  95

Leu Leu Gln Val Leu Asp Asp Gly Arg Leu Thr Asp Gly Gln Gly Arg
```

```
                    100                 105                 110
Thr Val Asp Phe Arg Asn Thr Val Ile Ile Met Thr Ser Asn Leu Gly
        115                 120                 125

Ala Glu His Leu Leu Ser Gly Ser Gln Lys Cys Thr Met Gln Val Ala
130                 135                 140

Arg Asp Arg Val Met Glu Gln Glu Arg Arg Gln Phe Arg Pro Glu Leu
145                 150                 155                 160

Leu Asn Arg Leu Asp Glu Ile Val Val Phe Asp Pro Leu Ser His Asp
                165                 170                 175

Gln Leu Arg Lys Val Ala Arg Leu Met
        180                 185

<210> SEQ ID NO 16
<211> LENGTH: 194
<212> TYPE: PRT
<213> ORGANISM: Homo sapien

<400> SEQUENCE: 16

Pro Lys Lys Pro Leu Thr Leu Ser Leu His Gly Trp Thr Gly Thr Gly
1               5                   10                  15

Lys Asn Phe Val Ser Lys Ile Ile Ala Glu Asn Ile Tyr Glu Gly Gly
            20                  25                  30

Leu Asn Ser Asp Tyr Val His Leu Phe Val Ala Thr Leu His Phe Pro
        35                  40                  45

His Ala Ser Asn Ile Thr Leu Tyr Lys Asp Gln Leu Gln Leu Trp Ile
    50                  55                  60

Arg Gly Asn Val Ser Ala Cys Ala Arg Ser Ile Phe Ile Phe Asp Glu
65                  70                  75                  80

Met Asp Lys Met His Ala Gly Leu Ile Asp Ala Ile Lys Pro Phe Leu
                85                  90                  95

Asp Tyr Tyr Asp Leu Val Asp Gly Val Ser Tyr Gln Lys Ala Met Phe
            100                 105                 110

Ile Phe Leu Ser Asn Ala Gly Ala Glu Arg Ile Thr Asp Val Ala Leu
        115                 120                 125

Asp Phe Trp Arg Ser Gly Lys Gln Arg Glu Asp Ile Lys Leu Lys Asp
    130                 135                 140

Ile Glu His Ala Leu Ser Val Ser Val Phe Asn Asn Lys Asn Ser Gly
145                 150                 155                 160

Phe Trp His Ser Ser Leu Ile Asp Arg Asn Leu Ile Asp Tyr Phe Val
                165                 170                 175

Pro Phe Leu Pro Leu Glu Tyr Lys His Leu Lys Met Cys Ile Arg Val
            180                 185                 190

Glu Met

<210> SEQ ID NO 17
<211> LENGTH: 194
<212> TYPE: PRT
<213> ORGANISM: Homo sapien
<220> FEATURE:
<221> NAME/KEY: VARIANT
<222> LOCATION: (1)...(194)
<223> OTHER INFORMATION: Xaa = Any Amino Acid

<400> SEQUENCE: 17

Pro Lys Lys Pro Leu Thr Leu Ser Leu His Gly Trp Ala Gly Thr Gly
1               5                   10                  15

Lys Asn Phe Val Ser Gln Ile Val Ala Glu Asn Leu His Pro Lys Gly
```

```
                20                  25                  30
Leu Lys Ser Asn Phe Val His Leu Phe Val Ser Thr Leu His Phe Pro
        35                  40                  45
His Glu Gln Lys Ile Lys Leu Tyr Gln Asp Gln Leu Gln Lys Trp Ile
    50                  55                  60
Arg Gly Asn Val Ser Ala Cys Ala Asn Ser Val Phe Ile Phe Asp Glu
65                  70                  75                  80
Met Asp Lys Leu His Pro Gly Ile Ile Asp Ala Ile Lys Pro Phe Leu
                85                  90                  95
Asp Tyr Tyr Glu Gln Val Asp Gly Val Ser Tyr Xaa Lys Ala Ile Phe
                100                 105                 110
Ile Phe Leu Ser Asn Ala Gly Gly Asp Leu Ile Thr Lys Thr Ala Leu
                115                 120                 125
Asp Phe Trp Arg Ala Gly Arg Lys Arg Glu Asp Ile Gln Leu Lys Asp
                130                 135                 140
Leu Glu Pro Val Leu Ser Val Gly Val Phe Asn Asn Lys His Ser Gly
145                 150                 155                 160
Leu Trp His Ser Gly Leu Ile Asp Lys Asn Leu Ile Asp Tyr Phe Ile
                165                 170                 175
Pro Phe Leu Pro Leu Glu Tyr Arg His Val Lys Met Cys Val Arg Ala
                180                 185                 190
Glu Met

<210> SEQ ID NO 18
<211> LENGTH: 192
<212> TYPE: PRT
<213> ORGANISM: C. elegans

<400> SEQUENCE: 18

Pro Arg Lys Pro Leu Val Leu Ser Phe His Gly Tyr Thr Gly Ser Gly
1               5                   10                  15
Lys Asn Tyr Val Ala Glu Ile Ile Ala Asn Asn Thr Phe Arg Leu Gly
                20                  25                  30
Leu Arg Ser Thr Phe Val Gln His Ile Val Ala Thr Asn Asp Phe Pro
        35                  40                  45
Asp Lys Asn Lys Leu Glu Glu Tyr Gln Val Glu Leu Arg Asn Arg Ile
    50                  55                  60
Leu Thr Thr Val Gln Lys Cys Arg Ser Ile Phe Ile Phe Asp Glu Ala
65                  70                  75                  80
Asp Lys Leu Pro Glu Gln Leu Leu Gly Ala Ile Lys Pro Phe Leu Asp
                85                  90                  95
Tyr Tyr Ser Thr Ile Ser Gly Val Asp Phe Arg Arg Ser Ile Phe Ile
                100                 105                 110
Leu Leu Ser Asn Lys Gly Gly Gly Glu Ile Ala Arg Ile Thr Lys Glu
                115                 120                 125
Gln Tyr Glu Ser Gly Tyr Pro Arg Glu Gln Leu Arg Leu Glu Ala Phe
                130                 135                 140
Glu Arg Glu Leu Met Asn Phe Ser Tyr Asn Glu Lys Gly Gly Leu Gln
145                 150                 155                 160
Met Ser Glu Leu Ile Ser Asn His Leu Ile Asp His Phe Val Pro Phe
                165                 170                 175
Leu Pro Leu Gln Arg Glu His Val Arg Ser Cys Val Gly Ala Tyr Leu
                180                 185                 190
```

```
<210> SEQ ID NO 19
<211> LENGTH: 194
<212> TYPE: PRT
<213> ORGANISM: Homo sapien

<400> SEQUENCE: 19

Pro Ser Lys Pro Leu Val Leu Ser Leu His Gly Trp Thr Gly Thr Gly
1               5                   10                  15

Lys Ser Tyr Val Ser Ser Leu Leu Ala Gln His Leu Phe Arg Asp Gly
            20                  25                  30

Leu Arg Ser Pro His Val His His Phe Ser Pro Ile Ile His Phe Pro
        35                  40                  45

His Pro Ser Arg Thr Glu Gln Tyr Lys Lys Glu Leu Lys Ser Trp Val
    50                  55                  60

Gln Gly Asn Leu Thr Ala Cys Glu Arg Ser Leu Phe Leu Phe Asp Glu
65                  70                  75                  80

Met Asp Lys Leu Pro Pro Gly Leu Met Glu Val Leu Gln Pro Phe Leu
                85                  90                  95

Gly Pro Ser Trp Val Val Tyr Gly Thr Asn Tyr Arg Lys Ala Ile Phe
            100                 105                 110

Ile Phe Ile Ser Asn Ala Gly Gly Glu Gln Ile Asn Gln Val Ala Leu
        115                 120                 125

Glu Ala Trp Arg Thr Asn Arg Asp Arg Glu Glu Ile Ser Leu Gln Glu
    130                 135                 140

Val Glu Pro Val Ile Ser Arg Ala Val Met Asp Asn Pro Gln His Gly
145                 150                 155                 160

Phe Trp Arg Ser Gly Ile Met Glu Glu His Leu Leu Asp Ala Val Val
                165                 170                 175

Pro Phe Leu Pro Leu Gln Arg His His Val Arg His Cys Val Leu Asn
            180                 185                 190

Glu Leu

<210> SEQ ID NO 20
<211> LENGTH: 128
<212> TYPE: PRT
<213> ORGANISM: Murine
<220> FEATURE:
<221> NAME/KEY: VARIANT
<222> LOCATION: (1)...(128)
<223> OTHER INFORMATION: Xaa = Any Amino Acid

<400> SEQUENCE: 20

Ala Ala Ala Leu His Gln Thr Leu Phe Ile Phe Asp Glu Ala Glu Lys
1               5                   10                  15

Leu His Pro Gly Leu Leu Glu Val Leu Gly Pro His Leu Glu Arg Arg
            20                  25                  30

Ala Pro Glu Xaa Xaa Gly Leu Ser Leu Xaa Trp Thr Ile Phe Leu Phe
        35                  40                  45

Leu Ser Asn Leu Arg Gly Asp Ile Ile Asn Glu Val Val Leu Lys Leu
    50                  55                  60

Leu Lys Ala Gly Trp Ser Arg Glu Glu Ile Thr Met Glu His Leu Glu
65                  70                  75                  80

Pro His Leu Gln Ala Glu Ile Val Asp His Arg Gln Trp Leu Trp
                85                  90                  95

His Ser Arg Leu Val Lys Glu Asn Leu Ile Asp Tyr Phe Ile Pro Phe
            100                 105                 110

Leu Pro Leu Glu Tyr Arg His Val Arg Leu Cys Ala Arg Asp Ala Phe
```

<210> SEQ ID NO 21
<211> LENGTH: 253
<212> TYPE: DNA
<213> ORGANISM: Homo sapien

<400> SEQUENCE: 21

```
cctggaatac aaacacctaa aaatgtgtat ccgagtggaa atgcagtccc gaggctatga      60
aattgatgaa gacattgtaa gcagagtggc tgaggagatg acatttttcc ccaaagagga     120
gagagttttc tcagataaag gctgcaaaac ggtgttcacc aagttagatt attactacga     180
tgattgacag tcatgattgg cagccggagt cactgcctgg agttggaaag aaacaacact     240
cagtccttcc acc                                                        253
```

<210> SEQ ID NO 22
<211> LENGTH: 253
<212> TYPE: DNA
<213> ORGANISM: Homo sapien

<400> SEQUENCE: 22

```
ggaccttatg tttgtggatt tttacacata ggctcacctt tacgtcaggg tccgatactt      60
taactacttc tgtaacattc gtctcaccga ctcctctact gtaaaagggg gtttctcctc     120
tctcaaaaga gtctatttcc gacgttttgc caccaagtgg ttcaatctaa taatgatgct     180
actaactgtc agtactaacc gtcggcctca gtgacggacc tcaacctttc tttgttgtga     240
gtcaggaagg tgg                                                        253
```

<210> SEQ ID NO 23
<211> LENGTH: 7
<212> TYPE: PRT
<213> ORGANISM: Homo sapien

<400> SEQUENCE: 23

```
Phe Phe Thr Met Glu Ala Val
  1               5
```

<210> SEQ ID NO 24
<211> LENGTH: 21
<212> TYPE: DNA
<213> ORGANISM: Homo sapien

<400> SEQUENCE: 24

```
gtggctgaga tgacattttt c                                                21
```

<210> SEQ ID NO 25
<211> LENGTH: 24
<212> TYPE: DNA
<213> ORGANISM: Homo sapien

<400> SEQUENCE: 25

```
gtggctgagg agatgacatt tttc                                             24
```

<210> SEQ ID NO 26
<211> LENGTH: 8
<212> TYPE: PRT
<213> ORGANISM: Homo sapien

<400> SEQUENCE: 26

```
Phe Phe Thr Met Glu Glu Ala Val
  1               5
```

<210> SEQ ID NO 27
<211> LENGTH: 205
<212> TYPE: DNA
<213> ORGANISM: Synthetic

<400> SEQUENCE: 27

| | |
|---|---:|
| cctggaatac aaacacctaa aaatgtgtat ccgagtggaa atgcagtccc gaggctatga | 60 |
| aattgatgaa gacattgtaa gcagagtggc tgaggagatg acattttcc ccaaagagga | 120 |
| gagagttttc tcagataaag gctgcaaaac ggtgttcacc aagttagatt attactacga | 180 |
| tgattgacag tcatgattgg cagcc | 205 |

<210> SEQ ID NO 28
<211> LENGTH: 19
<212> TYPE: DNA
<213> ORGANISM: Synthetic

<400> SEQUENCE: 28

| | |
|---|---:|
| cctggaatac aaacaccta | 19 |

<210> SEQ ID NO 29
<211> LENGTH: 20
<212> TYPE: DNA
<213> ORGANISM: Synthetic

<400> SEQUENCE: 29

| | |
|---|---:|
| ggctgccaat catgactgtc | 20 |

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30

| | |
|---|---:|
| gcaaaacagg gctttgtacc g | 21 |

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31

| | |
|---|---:|
| agtagagacg cgggtagatg | 20 |

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32

| | |
|---|---:|
| gcgtctctac tgcctcttcg | 20 |

<210> SEQ ID NO 33
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 33
atgccctggt cctagttcag                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ggtttcgcaa ggtgcttgga                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gggattccaa acttccatcc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
tccatggggt tggtaggaac                                              20

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
ggtgacagag taaaactatc tg                                           22

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38 gaccccagt agacgtttgt                                               20

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gtaaaaaatc atgagccctg c                                            21

```
<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
ccagagttag tgagcaggtc                                                   20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gaagcgttaa ggacctccac                                                   20

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
atctatctct gccaatttcc ac                                                22

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
gtcctggtaa acaaagtgct g                                                 21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
tggggttact ctatgttggt c                                                 21

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ctagcacagt atgccctaag                                                   20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide
```

-continued

```
<400> SEQUENCE: 46
tgaggaatgt gctgagggtc                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gctgtctcct accccatctg                                                    20

<210> SEQ ID NO 48
<211> LENGTH: 283
<212> TYPE: DNA
<213> ORGANISM: Unknown
<220> FEATURE:
<223> OTHER INFORMATION: cDNA clone of DYT1 intron 1
<221> NAME/KEY: misc_feature
<222> LOCATION: (1)...(283)
<223> OTHER INFORMATION: n = A, T, C or G

<400> SEQUENCE: 48
gtaggctggg gcgggggctg gaggctgggg ctgggctgg ggctgggcga tggcactagg          60
gctgaactag gaccagggca tgagaatgg aggatggagg ccggggatg gcaccagggc         120 cgggctagga ctagggctgg agcggggcct ggggctggg gctgggcgat ggcactaggg        180
cgggttgggg ctgggctgg ggctggggga tggagcgggg ccggggctg ggggtggggc         240 tgggggatcg actagggctg gnttaggacc aggcggttgg cat                          283

<210> SEQ ID NO 49
<211> LENGTH: 375
<212> TYPE: DNA
<213> ORGANISM: Unknown
<220> FEATURE:
<223> OTHER INFORMATION: cDNA clone of DYT1 intron 1
<221> NAME/KEY: misc_feature
<222> LOCATION: (1)...(375)
<223> OTHER INFORMATION: n = A, T, C or G

<400> SEQUENCE: 49
ggatggtgga tggaggctgg gggatggcag tagggccggg ctaggactgg ggctggagcg         60
gagtttgggg ctggggctca ggagcggggg ctgggctgg ggctgggct ggggatggc          120 actagggcag gccggggtag gggtcacatc ccaggagggc cgggctgggc agagctgagt       180 ccgcggggc cggaccccgg aagccaagcn gccggcctgc aggatgaggc ctggctcctc        240
ggccatgacc acagacgtgc cagacttaag tacggagacc tgaggagcca ggctgcagtt      300
ggcctacttt ncnctaagct gggggtggac cagtggtaac ctcctccgaa gtgggttctg      360
ctctttctag cctag                                                         375

<210> SEQ ID NO 50
<211> LENGTH: 439
<212> TYPE: DNA
<213> ORGANISM: Unknown
<220> FEATURE:
<223> OTHER INFORMATION: cDNA clone of DYT1 intron 1
<221> NAME/KEY: misc_feature
<222> LOCATION: (1)...(439)
<223> OTHER INFORMATION: n = A, T, C or G

<400> SEQUENCE: 50
```

-continued

```
ccactgccac tgccaccagt ttgcacccct aaccccctgtn ctgctcctcc cacccccaagg     60 cagagccggn gaaaggaaac agtttggtcc ctcctggtcg gctgcggaag agtctcacca    120
tccttctgtc tccgtagcta gaaaggaggc agaacccaca ttcggaggga ggttaccact    180 ggtccaccc cagcttagcg caaagtaggc caacctgcat gcctggnnct cctcaggntc     240
tgcctactta agtctggcag ctctnnntca tggccgaggt agccaggctc atcctgcagg    300
nnccngccnn ttgncttncc ggggtntcgn nnccccgtac tcagctcgtc cagccggcct    360
ctggatgtga cctaccgctg ctagtgcatc ccagccagcc agccagccgt ctagccagcc    420
aactgctcag ccagtctag                                                  439

<210> SEQ ID NO 51
<211> LENGTH: 368
<212> TYPE: DNA
<213> ORGANISM: Unknown
<220> FEATURE:
<223> OTHER INFORMATION: cDNA clone of DYT1 intron 1
<221> NAME/KEY: misc_feature
<222> LOCATION: (1)...(368)
<223> OTHER INFORMATION: n = A, T, C or G

<400> SEQUENCE: 51
caaagccaat caggagtggg gaagaaacac ggcaaaatgt agccacattt acagcccata     60
aganagccag caaagccgtc tagcctccaa gcaccttgcg aaacctcaag tactgcggtc    120
tggtaagctc ctggcccaga ggggacggcg gtccagggng ccctccctttt gctggtcctg   180 cctattctaa agccctggcc cgnctccttc ccgaaaagcc ccttggtgcc actgccactg    240
ccaccanttt gcncccctac ccctgtnctg ctcctcccac cccaaggcag atgcggnngg    300
ngaaaggaaa cantttggtc cctcctggtc ggctcgngga agactcctca ccatccttcc    360
tgtcttcc                                                             368

<210> SEQ ID NO 52
<211> LENGTH: 400
<212> TYPE: DNA
<213> ORGANISM: Unknown
<220> FEATURE:
<223> OTHER INFORMATION: cDNA clone of DYT1 intron 2

<400> SEQUENCE: 52
gaatatttac gagggtggtc tgaacagtga ctatgtccac ctgtttgtgg ccacattgct      60 cttttccacat gcttcaaaca tcaccttgta caaggcaagg atggaagttt ggaatccctt   120
cctggatgtc atcgggtttg ggtctctttt gttgtgggat gagatttggg agttctatgt    180
tgaaatgagt gagcccggaa aacggttcat gtctcagttc cccttggaaa ggtgtagaag    240
ttaagagttt gagatgcgtg gagcagttaa taccatcaaa gctttgtggt gggttctgaa    300
aatcggtcca gtgagtatgt agggtcatgg gattttagag gtggacatga tcaaatccat    360
cttagagatc aacacatctc actcattttt atttttcttat                          400

<210> SEQ ID NO 53
<211> LENGTH: 418
<212> TYPE: DNA
<213> ORGANISM: Unknown
<220> FEATURE:
<223> OTHER INFORMATION: cDNA clone of DYT1 intron 2
<221> NAME/KEY: misc_feature
<222> LOCATION: (1)...(418)
<223> OTHER INFORMATION: n = A, T, C or G

<400> SEQUENCE: 53
```

-continued

```
tttggagtga gacaggactg ggttcaggtc ccagctctgc cacatatagt cttgggcaag      60
tggagtaagc gctctctgtg cctcagttcc ctcatctgta aaatgagaac gatagtgccc     120
actccatggg gttggtagga acaaagaaga ttttgggcat gtaaagttct tagtgccgag     180
tgcacagtgg tctgtaagtg aagctgcggt tcttagtggt agaaggagct gattgatggc     240
cctggctgag aactttgtgt tcgctttttc ccnttttaat tcaggatcag ttacagttgt     300
ggattcgagg caacgtgagt gcctgtgcga ggtccatctt catatttgat gaaatggata     360
agatgcatgc aggcctcata gatgccntca anccttttcct cgactattat gacctggt     418
```

<210> SEQ ID NO 54
<211> LENGTH: 198
<212> TYPE: DNA
<213> ORGANISM: Unknown
<220> FEATURE:
<223> OTHER INFORMATION: cDNA clone of DYT1 intron 3

<400> SEQUENCE: 54

```
ctcgactatt atgacctggt ggatggggtc tcctaccaga aagccatgtt catatttctc      60
aggtaaggtc agggctagga catgatggat gggccccgag cccaagcctc tgagctccag     120
gagaaaaccc tgtccttacc cactgggatt gttttgcagc aatgctggag cagaaaggat     180
cacagatgtg tttggatt                                                   198
```

<210> SEQ ID NO 55
<211> LENGTH: 536
<212> TYPE: DNA
<213> ORGANISM: Unknown
<220> FEATURE:
<223> OTHER INFORMATION: cDNA clone of DYT1 intron 4
<221> NAME/KEY: misc_feature
<222> LOCATION: (1)...(536)
<223> OTHER INFORMATION: n = A, T, C or G

<400> SEQUENCE: 55

```
gtctgtgtcg gttttcaata acaagaacag gtgagtaggg ccatccaccg ccagtcccat      60
ctggttccta atcctgcacc ctaagtgtta aaagcatcag ggtcactgtc agcatcacct     120
gggagctggg tagaaagaaa tggagattct cagtcccctt ccgagtcatg agggaatct     180 ttgctgatga actccaggta acttttatga acactaatgt ttgacaagtg ctgttttatt     240 tttattttc agatagtttt actctgtcac ctaggctgga gtgcagtggc gtaaccttgc     300
ctcactgcaa cctctgcctc ccgggctcaa gcgattcttg tgcctcagcc tcctgagtag     360
ctgggattac aggtgcacac catgcccaag cnaatatttt gtattttag tagaganggg     420 gccccgtnca tgttaaccag gctggtcttg aactnttacc tcaggtgagt ccnccacctc     480
ggcctcccaa agtgctggga ttacaggcgt gagccactgt gtctcagctt atttt         536
```

<210> SEQ ID NO 56
<211> LENGTH: 1302
<212> TYPE: DNA
<213> ORGANISM: Unknown
<220> FEATURE:
<223> OTHER INFORMATION: cDNA clone of DYT1 intron 4
<221> NAME/KEY: misc_feature
<222> LOCATION: (1)...(1302)
<223> OTHER INFORMATION: n = A, T, C or G; m = A, or C; r = G, or A;
      w = A, or T; y = C, or T

<400> SEQUENCE: 56

```
gccactccaa gctaccatct gagattgttt cctgccctag agtggtaaag gcgtgaggtc      60
```

```
cgtctgccct cagctgtgtc cccaggccca gggcgtgcct ggcaacanna gcaggcctct    120
gagaaccagc ctcccacgtg agttcatgat agnaagacag cccctcgttc ccattcagtg    180
gttggttctg ttctttycct ggcmataagc tccactctgy mrtcagccam acatttattg    240
agtaccagtt gttggcaaag cactgttggg catgaaaagc attaacccag tgaatgagga    300
ggagcttggg ttgggacgga gccmcaraaw tacatggcag accagaagga aatcagctca    360
agtagaaara cacgcatggg ctcgtgggcg acgcagtgtg tgctgtgtca tctggggctg    420
ggaggaagtg tcctggatca ggagttccag gagcccagga ggagtggacg ggtcagtgca    480
gagccagccc gcaatcaggg gaagaaaaca cggccaaggc caggccttca cggggagccc    540
agcgtgggct gcacatctgc actctccagg ctagttttgg tgcccacatg ctctgcaggg    600
tctgggcact gtggcagcgg cagcaggctt ccctgttgct agtccagctg ctgaaactcc    660
agggagagtc aaaagttcc caaatacaga ggcgtggctg gtagtccttc ccgggaattc    720
ttcttgcttc ccgctttctg tggaactctg ccttccccac tctgcctctc tgcttgttcc    780
tgggccccag gacctctttc ccatcttcga tctcttaagt catacttggg gaggcctccc    840
ccagcccgcc gtgtaaagag ggctgtcaca gcttctgctg tcacagaagc attacaatgt    900
gcaggtgcct gttaacatct gccttcccca ctgatctgga gctccacaag ggagagggca    960
cacccagtag gtatgtgtgg gatggatagg agggtggatg acacccagta gatgtgtatg    1020
ggatggatag gagggtggat gacacccagt aggtgtgtat gggatggatg ggagggtggg    1080
tgacccctag tagatgtggg gggggtgggt gggtgacccc cagtaggtgt gtgtggcatg    1140
gataggtgac ccccagtaga cgtttgtggg acggatggga gggtaggtaa gtgaccccca    1200
ggaggcgtct atagggcagg tgggtggatg tggatgaaca gcaccttgtt tcttcttccc    1260
aggtggcttc tggcacagca gcttaattga ccggaacctc at    1302
```

<210> SEQ ID NO 57
<211> LENGTH: 240
<212> TYPE: DNA
<213> ORGANISM: Unknown
<220> FEATURE:
<223> OTHER INFORMATION: TORB intron 1-5'
<221> NAME/KEY: misc_feature
<222> LOCATION: (1)...(240)
<223> OTHER INFORMATION: n = A, T, C or G

<400> SEQUENCE: 57

```
ggagcggccg ctcaacgctt cgggtacggc gcgcgcgcga gctgtgggtc ggcgctgcgg    60 gggggcgcggg ggcgcggggg cgcggaggga cggcctcgtg ggcgcctggc acggaccggg    120
cccgtggcat ctagacggcg gtggtcccag ctggggtggg cggggagcgg atgggggcggc    180 cccggaaccg ttcgcnggaa cgcagaagcn gtgccttgaa acactctcag atcgtgnggc    240
```

<210> SEQ ID NO 58
<211> LENGTH: 310
<212> TYPE: DNA
<213> ORGANISM: Unknown
<220> FEATURE:
<223> OTHER INFORMATION: TORB intron 1-3'
<221> NAME/KEY: misc_feature
<222> LOCATION: (1)...(310)
<223> OTHER INFORMATION: n = A, T, C or G

<400> SEQUENCE: 58

```
gggaccaaag gacgtccgtc gttcccaccg accctaatcg ttcgcgngtc ngttcgctac    60
```

```
ccagtagaga gacttactta cnngtnnatc gaaggaatag tctggggctt cgcaattcct      120
ggaggtgtat tagaactttc accgtagcaa actgacggag ccgggatccc acaccgcctg      180
tgggnncgac acgggaccta ttgacacgaa gaacgaaacn gtcgattctt tcacgacgca      240
acgactacgt aaaaattcca gacaaagaga gaaacaagac cccgacaaga acgtcgagag      300
ttcgacctaa                                                             310
```

<210> SEQ ID NO 59
<211> LENGTH: 401
<212> TYPE: DNA
<213> ORGANISM: Unknown
<220> FEATURE:
<223> OTHER INFORMATION: TORB intron 2-5'
<221> NAME/KEY: misc_feature
<222> LOCATION: (1)...(401)
<223> OTHER INFORMATION: n = A, T, C or G

<400> SEQUENCE: 59

```
caggaacaac aaaaatccca agaaaccact gaccctttcc ttacacggct gggctggcac       60
aggcaagaat tttgtcagtn aaattgtggc tgaaaatctt cacccaaaag gtctgaagag      120
taactttgtc cacctgtttg tatcgactct gcacttccct catgagcaga agataaaact      180
gtaccaggca agagaacccg ctattatctc gtctgcaggc cagtcggact ggtccgggtg      240
acctgctcac taactctggc ctctgcttct ctttcctttg tgttgctgta gccccggct      300 ccactgagtt aaggcacact tagtccaggt agttacaaag ctctcctaca acatttctta      360
cttggttcca aaacagtcca gtggggtagg ggatgttatt t                          401
```

<210> SEQ ID NO 60
<211> LENGTH: 238
<212> TYPE: DNA
<213> ORGANISM: Unknown
<220> FEATURE:
<223> OTHER INFORMATION: TORB intron 2-3'

<400> SEQUENCE: 60

```
ttctgtaact ggtcctggac caaccatgaa agaagaaaca ggatgcgaag ctcaaagggc       60
tgcaccaaga ggcgcgcagg ctccatctgc tcctcatgca ctgaaggacg aggtcagagc      120
tcttagaatg gcaccctcac ccccactcgc taggtagcag cttttctaaa accttatctc      180
taaaaagtgg aaattggcag agatagatgc taaaatgcag agaagttttt cctaactc        238
```

<210> SEQ ID NO 61
<211> LENGTH: 391
<212> TYPE: DNA
<213> ORGANISM: Unknown
<220> FEATURE:
<223> OTHER INFORMATION: TORB intron 3-5'
<221> NAME/KEY: misc_feature
<222> LOCATION: (1)...(391)
<223> OTHER INFORMATION: n = A, T, C or G

<400> SEQUENCE: 61

```
gggatcattg acgcaatcaa gccgtttcta gactactacg agcaggttga cggagtgtct       60
taccgcaaag ccatcttcat ctttctcagg tcagcgggag gcggtttttt ggggcacaca      120
agcccttcat tctctcaatg ataaaatgag gtcctgagga ccatcagcac tttgtttacc      180
aggacgaaag tgcctgcttg gcacaaggca cttacctact gctttacttt tcctttgcca      240
gtcatcagca tggcacacag tgtgggttgt ggaaatgaac taaagaaata atcactggga      300
caggcgcggt ggctcacacc tgtcaatccn agcactttgg gnaggcatgg cgggcggatc      360
```

```
acaggagatc gagacatctg ctaacatgnt g                                       391
```

<210> SEQ ID NO 62
<211> LENGTH: 373
<212> TYPE: DNA
<213> ORGANISM: Unknown
<220> FEATURE:
<223> OTHER INFORMATION: TORB intron 3-3'
<221> NAME/KEY: misc_feature
<222> LOCATION: (1)...(373)
<223> OTHER INFORMATION: n = A, T, C or G

<400> SEQUENCE: 62

```
gtaagacaca gagtcttttt tnttttttag accgagtntc attnttgttg ccnangctgg         60
agtgcaatgg catgatctcg gctcgctgca acctccacct cccggrttca aacgattctc        120
ccacctcagc ctcccatgta gctgggatta cagncatgca ccaccattag cctggctaat       180
ttttgtgttt ttagtagaga tggggttact ctatgttggt caggctggcc ttgaactccc        240
gacctcaggt gatctacctg cctcggcctc ccaaagtgct gggattacag ccatgagcna        300
ccacnscnan cagacncaga agtcttaata tgtgatttta atctttattt ctctggcaaa        360
ctcagcaatg cag                                                            373
```

<210> SEQ ID NO 63
<211> LENGTH: 310
<212> TYPE: DNA
<213> ORGANISM: Unknown
<220> FEATURE:
<223> OTHER INFORMATION: TORB intron 4'
<221> NAME/KEY: misc_feature
<222> LOCATION: (1)...(310)
<223> OTHER INFORMATION: n = A, T, C or G

<400> SEQUENCE: 63

```
gtgagtccac cagggtaaag gagcccctta actgtccagc agtgagccgt ctgctctttc         60
attgagtgtt tgcacaaagc cacaggatcc cactggattt cctcactttg ctaaagtcag        120
gaattttctt agggcatact gtgctagaaa ccagtgagtg agtgtccagc tgagtcctcg        180
atgggcttgt tgcacactga caagagacnc tctcaagggg tacggacatg aggaatgtgc        240
tgagggtcgg gactggagct tggccaggtg gcggtggtgg caggaaaccc agctgtgtct        300
tgttctgcag                                                                310
```

<210> SEQ ID NO 64
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 64

```
gaattcctta ag                                                             12
```

<210> SEQ ID NO 65
<211> LENGTH: 8
<212> TYPE: PRT
<213> ORGANISM: Artificial Sequence
<220> FEATURE:
<223> OTHER INFORMATION: Synthetic Peptide
<223> OTHER INFORMATION: Xaa at position 2, 5 is a variable residue
      Xaa at position 8 is a threonine or a serine
      residue
<221> NAME/KEY: VARIANT
<222> LOCATION: (1)...(8)

```
<223> OTHER INFORMATION: Xaa = Any Amino Acid

<400> SEQUENCE: 65

Gly Xaa Thr Gly Xaa Gly Lys Xaa
 1               5

<210> SEQ ID NO 66
<211> LENGTH: 12
<212> TYPE: PRT
<213> ORGANISM: Artificial Sequence
<220> FEATURE:
<223> OTHER INFORMATION: Synthetic Peptide
<223> OTHER INFORMATION: Xaa at position 2, 3, 4, 8 is a hydrophobic
      residue Xaa at position 11 is a variable residue
<221> NAME/KEY: VARIANT
<222> LOCATION: (1)...(12)
<223> OTHER INFORMATION: Xaa = Any Amino Acid

<400> SEQUENCE: 66

Ser Xaa Xaa Xaa Phe Asp Glu Xaa Glu Lys Xaa His
 1               5                  10

<210> SEQ ID NO 67
<211> LENGTH: 10
<212> TYPE: DNA
<213> ORGANISM: Unknown
<220> FEATURE:
<223> OTHER INFORMATION: Exon/intron of DYT1

<400> SEQUENCE: 67
gtaggctggg                                                              10

<210> SEQ ID NO 68
<211> LENGTH: 10
<212> TYPE: DNA
<213> ORGANISM: Unknown
<220> FEATURE:
<223> OTHER INFORMATION: Exon/intron of DYT1

<400> SEQUENCE: 68
gcaaggatgg                                                              10

<210> SEQ ID NO 69
<211> LENGTH: 10
<212> TYPE: DNA
<213> ORGANISM: Unknown
<220> FEATURE:
<223> OTHER INFORMATION: Exon/intron of DYT1

<400> SEQUENCE: 69
gtaaggtcag                                                              10

<210> SEQ ID NO 70
<211> LENGTH: 10
<212> TYPE: DNA
<213> ORGANISM: Unknown
<220> FEATURE:
<223> OTHER INFORMATION: Exon/intron of DYT1

<400> SEQUENCE: 70
gtgagtaggg                                                              10

<210> SEQ ID NO 71
<211> LENGTH: 10
<212> TYPE: DNA
<213> ORGANISM: Unknown
<220> FEATURE:
```

<223> OTHER INFORMATION: Exon/intron of DYT1

<400> SEQUENCE: 71
tctttcccag                                                                          10

<210> SEQ ID NO 72
<211> LENGTH: 10
<212> TYPE: DNA
<213> ORGANISM: Unknown
<220> FEATURE:
<223> OTHER INFORMATION: Exon/intron of DYT1

<400> SEQUENCE: 72
tttaattcag                                                                          10

<210> SEQ ID NO 73
<211> LENGTH: 10
<212> TYPE: DNA
<213> ORGANISM: Unknown
<220> FEATURE:
<223> OTHER INFORMATION: Exon/intron of DYT1

<400> SEQUENCE: 73
tgttttgcag                                                                          10

<210> SEQ ID NO 74
<211> LENGTH: 10
<212> TYPE: DNA
<213> ORGANISM: Unknown
<220> FEATURE:
<223> OTHER INFORMATION: Exon/intron of DYT1

<400> SEQUENCE: 74
ttcttcccag                                                                          10

<210> SEQ ID NO 75
<211> LENGTH: 11
<212> TYPE: DNA
<213> ORGANISM: Unknown
<220> FEATURE:
<223> OTHER INFORMATION: Exon/intron of DYT1

<400> SEQUENCE: 75
cactgcagaa g                                                                        11

<210> SEQ ID NO 76
<211> LENGTH: 10
<212> TYPE: DNA
<213> ORGANISM: Unknown
<220> FEATURE:
<223> OTHER INFORMATION: Exon/intron of DYT1

<400> SEQUENCE: 76
caatgctgga                                                                          10

<210> SEQ ID NO 77
<211> LENGTH: 10
<212> TYPE: DNA
<213> ORGANISM: Unknown
<220> FEATURE:
<223> OTHER INFORMATION: Exon/intron of TORB

<400> SEQUENCE: 77
tggcttctgg                                                                          10

```
<210> SEQ ID NO 78
<211> LENGTH: 10
<212> TYPE: DNA
<213> ORGANISM: Unknown
<220> FEATURE:
<223> OTHER INFORMATION: Exon/intron of TORB

<400> SEQUENCE: 78
gcaagagaac                                                                 10

<210> SEQ ID NO 79
<211> LENGTH: 10
<212> TYPE: DNA
<213> ORGANISM: Unknown
<220> FEATURE:
<223> OTHER INFORMATION: Exon/intron of TORB

<400> SEQUENCE: 79
gtcagcggga                                                                 10

<210> SEQ ID NO 80
<211> LENGTH: 10
<212> TYPE: DNA
<213> ORGANISM: Unknown
<220> FEATURE:
<223> OTHER INFORMATION: Exon/intron of TORB

<400> SEQUENCE: 80
gtgagtccac                                                                 10

<210> SEQ ID NO 81
<211> LENGTH: 10
<212> TYPE: DNA
<213> ORGANISM: Unknown
<220> FEATURE:
<223> OTHER INFORMATION: Exon/intron of TORB

<400> SEQUENCE: 81
gttcttgcag                                                                 10

<210> SEQ ID NO 82
<211> LENGTH: 10
<212> TYPE: DNA
<213> ORGANISM: Unknown
<220> FEATURE:
<223> OTHER INFORMATION: Exon/intron of TORB

<400> SEQUENCE: 82
gttggtccag                                                                 10

<210> SEQ ID NO 83
<211> LENGTH: 10
<212> TYPE: DNA
<213> ORGANISM: Unknown
<220> FEATURE:
<223> OTHER INFORMATION: Exon/intron of TORB

<400> SEQUENCE: 83
gcaaactcag                                                                 10

<210> SEQ ID NO 84
<211> LENGTH: 9
<212> TYPE: DNA
<213> ORGANISM: Unknown
<220> FEATURE:
<223> OTHER INFORMATION: Exon/intron of TORB
```

```
<400> SEQUENCE: 84 tgttctgag                                                             9

<210> SEQ ID NO 85
<211> LENGTH: 11
<212> TYPE: DNA
<213> ORGANISM: Unknown
<220> FEATURE:
<223> OTHER INFORMATION: Exon/intron of TORB

<400> SEQUENCE: 85
ctctcaagct g                                                         11

<210> SEQ ID NO 86
<211> LENGTH: 10
<212> TYPE: DNA
<213> ORGANISM: Unknown
<220> FEATURE:
<223> OTHER INFORMATION: Exon/intron of TORB

<400> SEQUENCE: 86
caatgcaggc                                                           10

<210> SEQ ID NO 87
<211> LENGTH: 10
<212> TYPE: DNA
<213> ORGANISM: Unknown
<220> FEATURE:
<223> OTHER INFORMATION: Exon/intron of TORB

<400> SEQUENCE: 87
tggcctgtgg                                                           10

<210> SEQ ID NO 88
<211> LENGTH: 378
<212> TYPE: DNA
<213> ORGANISM: Unknown
<220> FEATURE:
<223> OTHER INFORMATION: cDNA clone of DYT1 intron 1
<221> NAME/KEY: misc_feature
<222> LOCATION: (1)...(378)
<223> OTHER INFORMATION: n = A, T, C or G

<400> SEQUENCE: 88
ctgggaaaga caaagccaat caggagtggg gaagaaacac ggcaaaatgt agccacattt     60
acagcccata aganagccag caaagccgtc tagcctccaa gcaccttgcg aaacctcaag    120
tactgcggtc tggtaagctc ctggcccaga ggggacggcg gtccagggng ccctcccttt    180
gctggtcctg cctattctaa agccctggcc cgnctccttc ccgaaaagcc ccttggtgcc    240
actgccactg ccaccanttt gcnccctac ccctgtnctg ctcctcccac cccaaggcag    300
atgcggnngg ngaaaggaaa cantttggtc cctcctggtc ggctcgngga agactcctca    360
ccatccttcc tgtcttcc                                                 378

<210> SEQ ID NO 89
<211> LENGTH: 402
<212> TYPE: DNA
<213> ORGANISM: Unknown
<220> FEATURE:
<223> OTHER INFORMATION: cDNA clone of DYT1 intron 2

<400> SEQUENCE: 89
gaatatttac gagggtggtc tgaacagtga ctatgtccac ctgtttgtgg ccacattgct     60
```

-continued

```
ctttccacat gcttcaaaca tcaccttgta caaggcaagg atggaagttt ggaatccctt      120
cctggatgtc atcgggtttg gggtctcttt gttgtgggat gagatttggg agttctatgt      180
tgaaatgagt gagcccggaa aacggttcat gtctcagttc cccttggaaa ggtgtagaag      240
ttaagagttt gagatgcgtg gagcagttaa taccatcaaa gctttgtggt gggttctgaa      300
aatcggtcca gtgagtatgt agggtcatgg gattttagag gtggacatga tcaaatccat      360
cttagagatc aacacatctc actcattttt attttcttat tt                         402

<210> SEQ ID NO 90
<211> LENGTH: 200
<212> TYPE: DNA
<213> ORGANISM: Unknown
<220> FEATURE:
<223> OTHER INFORMATION: cDNA clone of DYT1 intron 3

<400> SEQUENCE: 90
ctcgactatt atgacctggt ggatggggtc tcctaccaga aagccatgtt catatttctc       60
aggtaaggtc agggctagga catgatggat gggccccgag cccaagcctc tgagctccag      120
gagaaaaccc tgtccttacc cactgggatt gttttgcagc aatgctggag cagaaaggat      180
cacagatgtg gctttggatt                                                  200
```

TORSIN, TORSIN-RELATED GENES AND METHODS OF DETECTING NEURONAL DISEASE

RELATED APPLICATIONS

This application is a Continuation-In-Part of U.S. application Ser. No. 09/461,921, filed on Dec. 15, 1999 now abandoned, which is a Continuation-In-Part of U.S. application Ser. No. 09/218,363, filed on Dec. 22, 1998 now U.S. Pat. No. 6,397,616 issue May 14, 2002, which is a Continuation-In-Part of U.S. application Ser. No. 09/099,454, filed on Jun. 18, 1998 now abandoned, which claims the benefit of U.S. Provisional Application 60/050,244, filed on Jun. 19, 1997, the entire teachings of which are incorporated herein by reference.

GOVERNMENT SUPPORT

Part of the work performed during development of this invention utilized U.S. Government funds. The U.S. Government has certain rights to this invention.

BACKGROUND OF THE INVENTION

1. Field of the Invention

The present invention relates, in general, to torsin genes, preferably, torsinA which encodes the torsion dystonia gene, DYT1. In particular, the present invention relates to nucleic acid molecules coding for the torsin protein; purified torsin proteins and polypeptides; recombinant nucleic acid molecules; cells containing the recombinant nucleic acid molecules; antibodies having binding affinity specifically to torsin proteins and polypeptides; hybridomas containing the antibodies; nucleic acid probes for the detection of nucleic acids encoding torsin proteins; a method of detecting nucleic acids encoding torsin proteins or polypeptides in a sample; kits containing nucleic acid probes or antibodies; bioassays using the nucleic acid sequence, protein or antibodies of this invention to diagnose, assess, or prognose a mammal afflicted with torsion dystonia; therapeutic uses; and methods of preventing torsion dystonia in an animal (preferably, a human).

2. Related Art

Movement disorders constitute a group of human neurologic diseases in which aberrant neurotransmission in the basal ganglia is associated with uncontrollable body movements, such as chorea in Huntington disease, tremor and rigidity in Parkinson disease, and twisting contraction in torsion dystonia. Dystonic symptoms can be secondary to a number of neurologic conditions, and to drug or traumatic injury to the brain, but primary or torsion dystonia is distinguished by lack of other neurologic involvement (Fahn, S., *Adv Neurol* 50:1–8 (1988); Chutorian, A. H., *Acta Neuropediatricia* 2:33–45 (1996)) and, in contrast to these other two neurodegenerative diseases, the absence of any distinct neuropathology. The clinical manifestations of dystonia show wide variations in age and site of onset, as well as body regions involved. The prevalence of all forms of primary dystonia is estimated at 3/10,000 in North America (Nutt, J. G. et al., *Mov Disord* 3: 188–194 (1988)).

Early onset, generalized dystonia is the most disabling form of primary dystonia. Symptoms usually begin in an arm or leg at around 12 yrs (range 4–44 years) and spread to involve other limbs within about 5 years (Bressman, S. B. et al., *Annal Neurol* 36.771–777 (1994b); Greene, P. et al., *Mov Disord* 10: 143–152 (1995)). The clinical spectrum of early onset dystonia is similar in all ethnic populations, with highest prevalence in the Ashkenazi Jewish (termed here AJ) population (Zeman, W., & Dyken, P., *Psychiatr Neurol Neurochir* 10:77–121 (1967); Korczyn, A. D. et al., *Ann Neurol* 8:387–391 (1980); Eldridge, R., *Neurology* 20:1–78 (1970)), due to a founder mutation (Ozelius, L. et al., *Am. J. Hum. Genet.* 50:619–628 (1992); Risch, N. J. et al., *Nature Genetics* 9:152–159 (1995)). Early onset dystonia follows an autosomal dominant mode of inheritance with 30–40% penetrance (Bressman, S. B. et al., *Ann Neurol* 26:612–620 (1989); Risch, N. J. et al., *Am J Hum Genet* 46:533–538 (1990)). The responsible gene in Jewish and non-Jewish families has been mapped to human chromosome 9q34 (Ozelius, L. et al., *Neuron* 2:1427–1434 (1989); Kramer, P. L. et al., *Ann Neurol* 27:114–120 (1990) and Kramer, P. et al., *Am. J. Hum. Gen.* 55:468–475 (1994)). Haplotype analysis of the founder mutation in AJ families placed the DYT1 gene in a 1–2 cM interval centromeric to the ASS locus on chromosome 9 (Ozelius, L. et al., *Am. J. Hum. Genet.* 50:619–628 (1992)) with highest lod scores obtained with adjacent markers, D9S62a/b and D9S63 (Risch, N. et al., *Nature Genetics* 9:152–159 (1985)).

SUMMARY OF THE INVENTION

The present invention relates to dystonia, dystonia genes, encoded proteins and mutations in dystonia genes that result in a dystonia disorder. In particular, the invention provides isolated nucleic acid molecules coding for torsin proteins, preferably, torsinA.

The invention further provides purified polypeptides comprising amino acid sequences contained in torsin proteins.

The invention also provides nucleic acid probes for the specific detection of the presence of and mutations in nucleic acids encoding torsin proteins or polypeptides in a sample.

The invention further provides a method of detecting the presence of mutations in a nucleic acid encoding a torsin protein in a sample.

The invention also provides a kit for detecting the presence of mutations in a nucleic acid encoding a torsin protein in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a sequence complimentary to an RNA sequence encoding an amino acid sequence corresponding to the above-described polypeptide.

The invention also provides a cell that contains the above-described recombinant nucleic acid molecule.

The invention further provides a non-human organism that contains the above-described recombinant nucleic acid molecule.

The invention also provides an antibody having binding affinity specifically to a torsin protein or polypeptide.

The invention further provides a method of detecting a torsin protein or polypeptide in an sample.

The invention also provides a method of measuring the amount of a torsin protein or polypeptide in a sample.

The invention further provides a method of detecting antibodies having binding affinity specifically to a torsin protein or polypeptide.

The invention further provides a diagnostic kit comprising a first container means containing a conjugate comprising a binding partner of the monoclonal antibody and a label.

The invention also provides a hybridoma which produces the above-described monoclonal antibody.

The invention further provides diagnostic methods for dystonia disorders in humans, in particular, torsion dystonia. Preferably, a method of diagnosing the presence or absence of dystonia; predicting the likelihood of developing or a predisposition to develop dystonia in a human is provided herein. Specifically, methods of the present invention encompass detecting the presence or absence of a mutation in a gene wherein the mutation results in a dystonia disorder that affects humans. For example, the method comprises obtaining a sample from a human patient; evaluating the characteristics of nucleic acid encoding torsinA in the sample, wherein the evaluation comprises detecting the GAGGAG region (SEQ ID NO: 5 at nucleotide positions 946–951) in the sample; and diagnosing the presence or predisposition to develop torsion dystonia in a patient wherein the absence of three nucleotides from the GAGGAG region indicates the presence or predisposition to develop torsion dystonia.

The present invention also encompasses methods for diagnosing the presence or absence of a dystonia disorder in a human comprising detecting the presence or absence of at least one mutation in a dystonia gene, wherein the presence of a mutation in the dystonia gene is indicative of a positive diagnosis and the absence of the mutation is indicative of the absence of a dystonia disorder. The dystonia disorder can be, for example, torsion dystonia. A biological sample obtained from a human can be used in the diagnostic methods. The biological sample can be a bodily fluid sample such as blood, saliva, semen, vaginal secretion, cerebrospinal and amniotic bodily fluid sample. Alternatively or additionally, the biological sample is a tissue sample such as a chorionic villus, neuronal, epithelial, muscular and connective tissue sample. In both bodily fluid and tissue samples, nucleic acids are present in the samples. In another embodiment the sample is a nucleic acid preparation obtained from human chromosome 9q34.

The dystonia gene can be the DYT1 gene (SEQ ID NO: 1). In humans who are not affected by a dystonia disorder such as torsion dystonia, two normal alleles of the DYT1 gene are present. Humans affected with a dystonia disorder, such as torsion dystonia, have one normal allele and one abnormal allele characterized by at least one mutation in the nucleotide sequence. In one embodiment the mutation is a deletion mutation. Alternatively the mutation can be a missense, or frame shift mutation. In a preferred embodiment the deletion mutation is a deletion of one or more nucleotides from the GAGGAG region of SEQ ID NO: 5 at nucleotide positions 946–948; 949–951; 947–949; 948–950; or any combination thereof. For example, if the mutation to be detected is a deletion mutation, the presence or absence of three nucleotides in this region can result in the deletion of an A and two Gs, which, in turn, results in GAG rather than GAGGAG in the sequence. The presence or absence of these three nucleotides is indicative of a negative or positive diagnosis, respectively. The biological samples obtained from humans are evaluated in parallel to control samples with and without the appropriate dystonia disorder mutation.

The invention also relates to methods of detecting the presence or absence of dystonia disorder in a human wherein the dystonia disorder is characterized by one or more mutations in a dystonia gene. In this aspect of the invention a test sample comprising the dystonia gene is analyzed for the presence or absence of one or more mutations in the dystonia gene and compared to results of analysis of control samples. The test samples comprise biological samples from the human (e. g., blood, tissue). The control samples comprise biological samples with or without a mutation in the dystonia gene. The presence or absence of a mutation in the test sample is indicative of a positive or negative diagnosis, respectively, for a dystonia disorder.

Another aspect of the invention relates to methods of detecting the presence or absence of a dystonia disorder, wherein the test sample from the human is evaluated by performing a polymerase chain reaction, hereinafter "PCR," with oligonucleotide primers capable of amplifying a dystonia gene, such as the DYT1 gene (SEQ ID NO: 1). The PCR-specific primers can be, for example, designed for a region of exon 5 of the DYT1 gene (SEQ ID NO: 27), such as SEQ ID NOS: 28 and 29. Following PCR amplification of a nucleic acid sample, the amplified nucleic acid fragments are separated and mutations in the DYT1 gene and alleles of the dystonia gene detected. For example, a mutation in the DYT1 gene is indicative of the presence of the torsion dystonia, whereas the lack of a mutation is indicative of a negative diagnosis. In one embodiment the mutation is a deletion mutation comprising the deletion of three nucleotides in the DYT1 gene. In another embodiment the mutation is in three nucleotides from a GAGGAG region of SEQ ID NO: 5, preferably at nucleotide positions 946–948; 949–951; 947–949; 948–950; or any combination thereof. In yet another embodiment, the method further comprises the additional step of sequencing the amplified DNA fragments.

An additional aspect of the invention is a method of determining the presence or absence of a dystonia disorder in a human including the steps of contacting a biological sample obtained from the human with a nucleic acid probe to a dystonia gene; maintaining the biological sample and the nucleic acid probe under conditions suitable for hybridization; detecting hybridization between the biological sample and the nucleic acid probe; and comparing the hybridization signal obtained from the human to a control sample which does or does not contain a dystonia disorder. The absence of a hybridization signal is indicative of a positive diagnosis. The presence of a hybridization signal is indicative of a negative diagnosis. The dystonia disorder can be, for example, torsion dystonia. The hybridization is performed with a nucleic acid fragment of a dystonia gene such as DYT1 (SEQ ID NO: 1). The nucleic acid probe can be labeled (e. g., fluorescent, radioactive, enzymatic, biotin label).

The invention also encompasses methods for predicting whether a human is likely to be affected with a dystonia disorder, comprising obtaining a biological sample from the human; contacting the biological sample with a nucleic acid probe; maintaining the biological sample and the nucleic acid probe under conditions suitable for hybridization; and detecting hybridization between the biological sample and the nucleic acid probe. In another embodiment the method further comprises performing PCR with oligonucleotide primers capable of amplifying a dystonia gene (e.g., DYT1, SEQ ID NO: 1); and detecting a mutation in amplified DNA fragments of the dystonia gene, wherein the mutation in the dystonia gene is indicative of the presence or absence of the torsion dystonia. The hybridization can detect, for example, a deletion in nucleotides indicative of a positive diagnosis; or the presence of nucleotides indicative of a negative diagnosis. In one embodiment the deletion is of nucleotides corresponding to GAG from a GAGGAG region (SEQ ID NO: 5). The deletion mutation can be a deletion of nucleotides 946–948; 949–951; 947–949; 948–950; or any combination thereof from SEQ ID NO: 5. In another embodiment, the amplified DNA fragments can be sequenced to detect the presence or absence of mutations.

The invention further provides for methods of determining the presence or absence of a dystonia disorder in a human comprising obtaining a biological sample from the human; and assessing the level of a dystonia protein in the biological sample comprising bodily fluids, tissues or both from the human. The levels or concentrations of the dystonia protein are determined by contacting the sample with at least one antibody specific to a dystonia protein, and detecting the levels of the dystonia protein. An alteration in the dystonia protein levels is indicative of a diagnosis. The dystonia protein detected can be, for example, torsinA (SEQ ID NO: 2) encoded by the nucleic acid sequence of SEQ ID NO: 1. The antibody used in the method can be a polyclonal antibody or a monoclonal antibody and can be detectably labeled (e. g., fluorescence, biotin, colloidal gold, enzymatic). In another embodiment the method of assessing the level or concentration of the dystonia protein further comprises contacting the sample with a second antibody specific to the dystonia protein or a complex between an antibody and the dystonia protein.

The present invention also provides for a kit for diagnosing the presence or absence of a dystonia disorder in a human comprising one or more reagents for detecting a mutation in a dystonia gene, such as DYT1, or a dystonia protein, such as torsinA, in a sample obtained from the human. The one or more reagents for detecting the torsion dystonia are used for carrying out an enzyme-linked immunosorbent assay or a radioimmunoassay to detect the presence of absence of dystonia protein. In another embodiment the kit comprises one or more reagents for detecting the torsion dystonia by carrying out a PCR, hybridization or sequence-based assay or any combination thereof.

It is also envisioned that the methods of the present invention can diagnosis a mutation in a dystonia gene, such as DYT1, which encodes a dystonia protein, such as torsinA, wherein a mutation in the dystonia gene for the human is compared to a mutation in a dystonia gene for a parent of the human who is unaffected by a torsion dystonia, a parent of the human who is affected by the torsion dystonia and a sibling of the human who is affected by the torsin dystonia.

The invention also provides methods for therapeutic uses involving all or part of (1) the nucleic acid sequence encoding torsin protein or (2) torsin protein.

Another embodiment of the invention provides the exon structure and physical map of the human TOR1A and TOR1B genes.

The invention also provides 5' and 3' intron nucleic acid sequence flanking the exons of the TOR1A and TOR1B genes.

The invention further provides nucleic acid sequences useful as probes and primers for the identification of mutations or polymorphisms which mediate clinical neuronal diseases, or which confer increased vulnerability (e. g., genetic predisposition) respectively, to other neuronal diseases.

Another embodiment of the invention provides methods utilizing the disclosed probes and primers to detect mutations or polymorphisms in other neuronal genes implicated in conferring a particular phenotype which gives rise to overt clinical symptoms in a mammal that are consistent with (e. g., correlate with) the neuroanatomical expression of the gene. For example, the methods described herein can be used to confirm the role of TOR1A or TOR1B in neuronal diseases, including but not limited to dopamine-mediated diseases, movement disorders, neurodegenerative diseases, neurodevelopmental diseases and neuropsychiatric disorders.

A particular embodiment of the invention provides a method of detecting the presence or absence of Parkinson's disease in a mammal, for example a human.

An alternative embodiment provides a method of identifying a gene comprising a mutation or a polymorphism resulting in a dopamine-mediated disease, or a neuronal disease.

Another embodiment of the invention provides a method of identifying a mutation or polymorphism in a neuronal gene which confers increased susceptibility to a neuronal disease.

Definitions

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA. The "isolated" nucleic acid molecule is purified from its natural in vivo state.

Recombinant DNA. Any DNA molecule formed by joining DNA segments from different sources and produced using recombinant DNA technology (a.k.a. molecular genetic engineering).

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA).

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome can be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., *Current protocols in Molecular Biology*, John Wily & Sons, Inc., New York, N.Y. (1989). A nitrocellulose filter is incubated overnight at 68° C. with labeled probe in a solution containing 50% formamide, high salt (either 5×SSC[20×: 3M NaCl/0.3M trisodium citrate] or 5×SSPE [20×: 3.6 M NaCl/0.2 M $NaH_2PO_4$/0.02M EDTA, pH 7.7]), 5× Denhardt's solution, 1% SDS, and 100 µg/ml denatured salmon sperm DNA. This is followed by several washes in 0.2× SSC/0.1% SDS at a temperature selected based on the desired stringency: room temperature (low stringency), 42° C. (moderate stringency) or 68° C. (high stringency). The temperature is selected is determined based on the melting temperature (Tm) of the DNA hybrid.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The ears of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. AN oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cells, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptides(s).

Expression Vector. A vector or vehicle similar to a cloning vector but which is capable of expressing a gene which has been cloned into it after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additional contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modification for the performance of a specific function. The term "functional derivative" is intended to include the "fragment," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980).

Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result form a mutant nucleic acid molecule and also refers to a polypeptide which is modified at one, or more, amino acid residues from the wildtype (naturally occurring) polypeptide. The term "mutation", as used herein, can also refer to any modification in a nucleic acid sequence encoding a dystonia protein. For example, the mutation can be a point mutation or the addition, deletion, insertion and/or substitution of one or more nucleotides or any combination thereof. The mutation can be a missense or frameshift mutation. Modifications can be, for example, conserved or non-conserved, natural or unnatural.

Species. A "species" is a group of actually or potentially interbreeding natural populations. A species variation within a nucleic acid molecule or protein is a change in the nucleic acid or amino acid sequence that occurs among species and can be determined by DNA sequencing of a molecule in question.

Polyacrylamide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS. The polypeptides fractionated by polyacrylamide gel electrophoresis can be visualized directly by a staining procedure if the number of polypeptide component is small.

Western Transfer Procedure. The purpose of the Western transfer procedure (also referred to as blotting) is to physically transfer polypeptides fractionated by polyacrylamide gel electrophoresis onto a nitrocellulose filter paper or another appropriate surface or method, while retaining the relative positions of polypeptides resulting from the fractionation procedure. The blot is then probed with an antibody that specifically binds to the polypeptide of interest.

Purified. A "purified" protein or nucleic acid is a protein or nucleic acid that has been separated from a cellular component. "Purified" proteins or nucleic acids have been purified to a level of purity not found in nature.

Substantially Pure. A "substantially pure" protein or nucleic acid is a protein or nucleic acid preparation that is lacking in all other cellular components.

Nucleic Acids. Nucleic acids are defined herein as heteropolymers of nucleic acid molecules. Nucleic acid molecules are meant to refer to chains of nucleotides joined together by phosphodiester bonds to form a nucleic acid heteropolymer. The nucleic acid molecules can be double stranded or single stranded and can be deoxyribonucleotide (DNA) molecules, such as cDNA or genomic DNA, or ribonucleotide (RNA) molecules. As such, the nucleic acid molecule can include one or more exons, with or without, as appropriate, introns.

PCR. PCR refers to the polymerase chain reaction, a rapid procedure for the in vitro enzymatic amplification of nucleic acids. The nucleic acid to be amplified is denatured by heating in the presence of DNA polymerase, excess deoxyribonucleotide triphosphates and oligonucleotides that specifically hybridize to target sequences to prime new DNA synthesis. The amplification procedure is characterized by cycling which leads to a multi-fold amplification of a nucleic acid fragment of interest.

BRIEF DESCRIPTION OF THE DRAWINGS

FIG. 2. Sequence variations in cDNAs in DYT1 region. Diagrams are scaled representations of each of the four cDNA transcripts in the critical region. The striped black box indicated 5' untranslated sequence; the striped white box indicates deduced open reading frame; and the wavy line indicates 3' untranslated sequences. The dashed lines at the 5' end of the open reading frame of cDNAs DQ2 and DQ3 indicate that no stop codon 5' to the first predicted methionine (M) has been found. The numbers flanking the open reading frame box indicate the beginning and end of the cDNAs and the nucleotide position of the predicted start and stop codons. Regions generating SSCP shifts are indicated above the transcript diagram: + marks those for which nucleotide changes have not yet been determined; * marks the location of known nucleotide changes corresponding to SSCP shifts; ^ marks the GAG-deletion in cDNA DQ2. Nucleotide changes and resulting amino acid conversions are given below each cDNA. Transcript sizes were estimated by northern blot analysis.

FIGS. 3A and 3B. Northern blot analysis of DQ2 and DQ1 transcripts. Northern blots of human RNA (Clontech) in order from left to right-fetal: 1) brain, 2) lung, 3) liver and 4) kidney; and adult: 1) heart, 2) brain, 3) placenta, 4) lung, 5) liver, 6) skeletal muscle, 7) kidney and 8) pancreas. Blots hybridized to PCR probes corresponding in FIG. 3A to nucleotides 149–1307 of cDNA DQ2; and in FIG. 3B to nucleotides 28–728 of cDNA DQ1. Marker sizes are indicated by bars.

FIGS. 4A–4C. Comparison of predicted amino acid sequences of torsin gene family members.

FIG. 4A. Alignment of torsins and torps. torsinA (SEQ ID NO: 9) and torsinB (SEQ ID NO: 10) are encoded by cDNAs DQ2 and DQ1, respectively. TorpCel (SEQ ID NO: 11) is the predicted amino acid sequence from a *C. elegans* genomic sequence. Torp-1 (SEQ ID NO: 12) and torp-2 (SEQ ID NO: 13) correspond to overlapping expressed sequence tag cDNAs from human and mouse, respectively. The solid triangle represents the site of the GAG (E) deletion in torsinA. Conserved cysteine residues are represented by *. Darkly shaded residues are identical to a consensus sequence; lightly shaded residues are similar. Conserved possible phosphorylation sites for protein kinase C (PKC) and casein kinase 2 (CK2) are boxed.

FIG. 4B. Schematic representation of torsinA domains. The N-terminal region (left) contains about 40 hydrophobic amino acids, preceded by two basic residues (K, R) and bisected by a polar and an acidic residue (Q, E). The ATP-binding domain is indicated along with its conserved A and B motifs. Two additional motifs conserved with the HSP100 family (SN and IV) are shaded.

FIG. 4C. Comparison of torsin A (SEQ ID NO: 16), torsin B (SEQ ID NO: 17) torpCel (SEQ ID NO: 18), torp-1 (SEQ ID NO: 19), and torp-2 (SEQ ID NO: 20) with two representative members of the HSP100 family. SKD3 (SEQ ID NO: 14), from mouse is an HSP100 family member of class 2M; HSP101 (SEQ ID NO: 15) from soybean is a heat shock protein of class 1B (Schirmer, E. C. et al., 1996, *TIBS.* 21:289–296). Shaded residues are identical to a consensus sequence. The conserved motifs (A, B, SN and IV) occur in all seven proteins.

FIG. 5A. Sequence. Autoradiograph of sequencing gel showing mutant and normal sequence from amplified genomic DNA using primer 6419 (SEQ ID NO: 64). The sequence, which is read 5' to 3' from the bottom up, demonstrates the GAG-deletion found on one allele in an affected patient. This mutation occurs at nucleotides 946–948 in the coding region and results in the deletion of a Glu residue from the protein.

FIG. 5B. SSCP analysis of fragments. Autoradiograph showing PCR-SSCP analysis of genomic DNA from affected and control individuals. Primers (6418 and 6419) were used to produce 250 bp fragment which were resolved in non-denaturing acrylamide gels. Lane 1, 3, and 5 are affected individuals with typical early onset dystonia; lane 2 and 4 are unaffected individuals. Solid triangle indicates shifted band associated with GAG-deletion; open triangle indicates 2 bands associated with normal allele.

FIG. 5C. Digestion of PCR fragment with BseR1. PCR products were generated from genomic DNA with primers 6419 and H48 and the 200 bp product was digested with BseRI. Bands of 120 bp and 70 bp were generated from control DNA (lane 2), whereas a novel band of 130 bp was generated from affected individuals with the GAG-deletion (lane 1), because of the loss of a BseRI site. Lane 3 and 4 are markers: 3) PCR products of specific sizes (50, 1 00 and 130 bp) and 4) 100 bp ladder (Pharmacia).

FIG 5D. Sequence surrounding GAG-deletion. Normal genomic (SEQ ID NO: 21)/cDNA (SEQ ID NO: 22) sequence of torsinA showing position of primers (arrows); the GAGGAG sequence (bracketed) in which the GAG-deletion occurs; and BseRI sites (*, site deletion lost as a result of the deletion).

FIGS. 9A and 9B. Exon/intron structure of DYT1 (SEQ ID NOS: 67–77) and TORB genes (SEQ ID NOS: 78–87).

FIG. 10. Non-GAG deleted dystonia patients evaluated for mutations in TOR1A and TOR1B.

FIG. 11. Genotypes of dystonic individuals with apparent homozygosity in DYT1 region.

FIGS. 12A and 12B. Primers used to amplify DYT1 and TORB genes. 12A. SEQ ID NOS.: 30–39. 12B. SEQ ID NOS.: 40–47.

FIG. 13. GenBank sequences representing the Torsin gene family. Proteins are named as torsins or torps according to phylogenetic relationships as determined by ClustalX and shown in FIG. 8. Species are denoted for orthologs as follows: h-*Homo sapiens*, m-*Mus musculus*, r-*Rattus norvegicus*, dr-*Danio rerio*, dm-*Drosophila melanogaster*, ce-*Caenorhabditis elegans*. Gene names have been approved by mouse and human gene committees. Accession numbers indicate either a GenBank entry for a cloned gene, or a representative EST.

FIGS. 14A–14E. Nucleotide sequences (SEQ ID NOS.: 48–51 and 88) of DYT1 intron 1 cDNA clones.

FIGS. 15A–15C. Nucleotide sequences (SEQ ID NOS.: 52, 89 and 53) of DYT1 intron 2 cDNA clones.

FIGS. 16A and 16B. Nucleotide sequences (SEQ ID NOS.: 54 AND 90) of DYT 1 intron 3 cDNA clone.

FIGS. 17A and 17B. Nucleotide sequences (SEQ ID NOS.: 55 and 56) of DYT1 intron 4 cDNA clones.

FIGS. 18A and 18B. 5' nucleotide sequence of TORB intron 1 (FIG. 18A; SEQ ID NO.: 57) and 3' nucleotide sequence of TORB intron 1 (FIG. 18B; SEQ ID NO.: 58).

FIGS. 19A and 19B. 5' nucleotide sequence of TORB intron 2 (FIG. 19A; SEQ ID NO.: 59) and 3' nucleotide sequence of TORB intron 2 (FIG. 19B; SEQ ID NO.: 60).

FIGS. 20A and 20B. 5' nucleotide sequence of TORB intron 3 (FIG. 20A; SEQ ID NO.: 61) and 3' nucleotide sequence of TORB intron 2 (FIG. 20B; SEQ ID NO.: 62).

FIG. 21. Nucleotide sequence (SEQ ID NO.: 63) of TORB intron 4.

Figure 1:
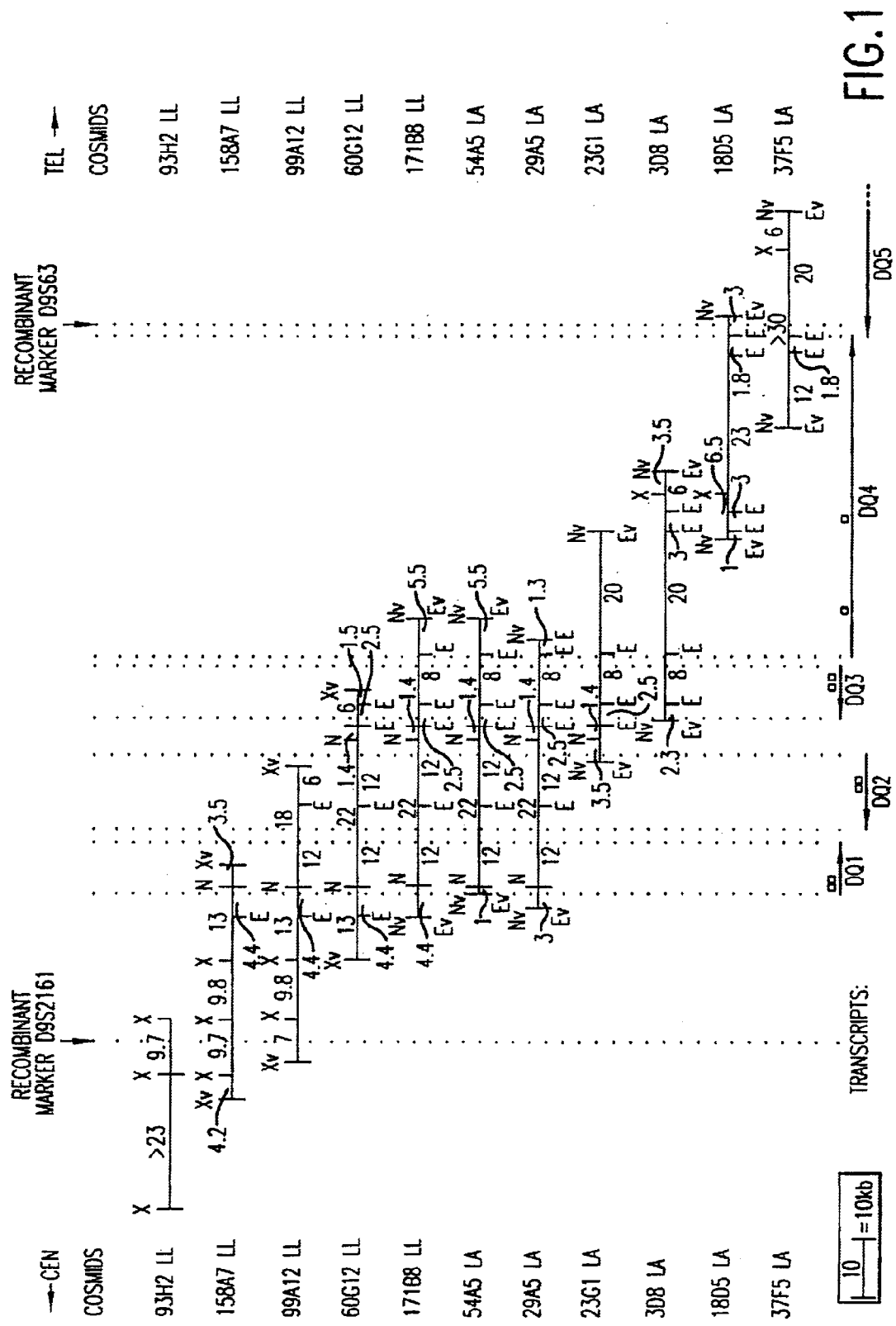
FIG. 1. Cosmid contig and transcript map across DYT1 target region. Horizontal lines depict cosmids, vertical lines denote restriction sites X=XhoI, E=EcoRI, and N=NotI (Nv,Xv,Ev=vector ends) and numbers indicate size of fragments in kilobases. The dotted vertical lines indicate the 5' and 3' ends of each cDNA and the position of the recombinant markers D9S2161 and D9S63. Dark horizontal arrows at the bottom represent transcripts, with the direction of the arrow indicating the direction of transcription. The boxes above the cDNAs point out some of the trapped exons. The cosmids used to construct the map are listed on both sides. The cosmid names followed by LL are from the Lawrence Livermore chromosome 9-specific library and designated names are all preceded by LL09NC01; those followed by LA are from the Los Alamos chromosome 9-specific library. CEN stands for centromere and TEL for telomere and indicate the orientation of this map with respect to chromosome 9q.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

For purposes of clarity of disclosure, and not by way of limitation, the detailed description of the invention is divided into the following subsections:

I. Isolated Nucleic Acid Molecules Coding for Torsin Polypeptides.
II. Purified Torsin Polypeptides.
III. A Nucleic Acid Probe for the Specific Detection of Torsin Nucleic Acid.
IV. A Method of Detecting the Presence of Torsin Nucleic Acid in a Sample.
V. A Kit for Detecting the Presence of Torsin Nucleic Acid in a Sample.
VI. DNA Constructs Comprising a Torsin Nucleic Acid Molecule and Cells Containing These Constructs.
VII. An Antibody Having Binding Affinity to a Torsin Polypeptide and a Hybridoma Containing the Antibody.
VIII. A Method of Detecting a Torsin Polypeptide or Antibody in a Sample.
IX. A Diagnostic Kit Comprising a Torsin Protein or Antibody.
X. Diagnostic Screening and Treatment.
XI. Transgenic Torsin "Knock-out" Mice.
XII. HSV-1 Amplicon Constructs.
XIII. DYT1, Related Genes and Methods of Detecting a Mutation or Polymorphism which Mediates Dystonia Disorders.
XIV. Methods of Identifying Genes Comprising a Polymorphism that Confers Susceptibility to Neuronal Diseases or a Mutation that Mediates Neuronal Disease.

I. Isolated Nucleic Acid Molecules Coding for Torsin Polypeptides.

The present invention relates to isolated nucleic acid molecules with sequences at least 90% identical (more preferably, 95%, 96%, 97%, 98%, 99% or 100% identical) to one or more of the following: a nucleotide sequence encoding the torsin polypeptide comprising the complete amino acid sequence in SEQ ID NOS: 2 or 4; a nucleotide sequence encoding the torsin polypeptide comprising the complete amino acid sequence encoded by the polynucleotide clone contained in ATCC Deposit No. 98454 or 98455; or a nucleotide sequence complementary to either of these nucleotide sequences.

More specifically, the isolated nucleic acid molecule can be a torsin nucleotide sequence with greater than 90% identity or similarity to the nucleotide sequence present in SEQ ID NOS: 1 or 3 (preferably greater than 95%, 96%, 97%, 98%, 99% or 100%). In another preferred embodiment, the isolated nucleic acid molecule comprises the torsin nucleotide sequence present in SEQ ID NOS: 1 or 3. In another embodiment, the isolated nucleic acid molecule encodes the torsin amino acid sequence present in SEQ ID NOS: 2 or 4.

The torsin nucleic acids were deposited at the American Type Culture Collection, 12301 Parklawn Drive, Rockville, Md. 20852, USA on Jun. 12, 1997 as ATCC Nos. 98454 and 98455.

Included within the scope of this invention are the functional equivalents of the herein-described isolated nucleic acid molecules and derivatives thereof. For example, the nucleic acid sequences depicted in SEQ ID NOS: 1 or 3 can be altered by substitutions, additions or deletions that provide for functionally equivalent molecules, Due to the degeneracy of nucleotide coding sequences, other DNA sequences which encode substantially the same amino acid sequence as depicted in SEQ ID NOS: 2 or 4 can be used in the practice of the present invention. These include but are not limited to nucleotide sequences comprising all or portions of torsin nucleic acid depicted in SEQ ID NOS: 1 or 3 which are altered by the substitution of different codons that encode a functionally equivalent amino acid residue within the sequence.

In addition, the nucleic acid sequence can comprise a nucleotide sequence that results from the addition, deletion or substitution of at least one nucleotide from the 5' and/or 3' end of the nucleic acid sequence shown in SEQ ID NOS: 1 or 3 or a derivative thereof. Any nucleotide or polynucleotide can be used in this regard, provided that its addition, deletion or substitution does not substantially alter coding for the amino acid sequence of SEQ ID NOS: 2 or 4. Moreover, the nucleic acid molecule of the present invention can, as necessary, have restriction endonuclease recognition sites added to its 5' and/or 3' end. All variations of the nucleotide sequence of the torsin gene and fragments thereof permitted by the genetic code are, therefore, included in this invention.

Further, it is possible to delete codons or to substitute one or more codons for codons other than degenerate codons to produce a structurally modified polypeptide, but one that has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to torsin proteins are provided. In particular, the nucleic acid molecule can be isolated from a biological sample containing torsin RNA or DNA.

The nucleic acid molecule can be isolated from a biological sample containing torsin mRNA using the techniques of cDNA cloning and subtractive hybridization. The nucleic acid molecule can also be isolated from a cDNA library using an homologous probe.

The nucleic acid molecule can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that genomes can be subject to slight allelic variations between individuals. Therefore, the isolated nucleic acid molecule is also intended to include allelic variations, so long as the sequence is a functional derivative of a torsin coding sequence. When a torsin allele does not encode the identical sequence to that found in SEQ ID NOS:1 or 3, it can be isolated and identified as torsin using the same techniques used herein, and especially PCR techniques to amplify the appropriate gene with primers based on the sequences disclosed herein.

One skilled in the art will realize that organisms other than humans will also contain torsin genes (for example, eukaryotes; more specifically, mammals (preferably, gorillas, rhesus monkeys, and chimpanzees), rodents, worms (preferably, *C. elegans*), insects (preferably, *D. melanogaster*) birds, fish, yeast, and plants). The invention is intended to include, but is not limited to, torsin nucleic acid molecules isolated from the above-described organisms.

B. Synthesis of Nucleic Acid

Isolated nucleic acid molecules of the present invention are also meant to include those chemically synthesized. For example, a nucleic acid molecule with the nucleotide sequence which codes for the expression product of a torsin gene can be designed and, if necessary, divided into appropriate smaller fragments. Then an oligomer which corresponds to the nucleic acid molecule, or to each of the divided fragments, can be synthesized. Such synthetic oligonucleotides can be prepared synthetically (Matteucci et al., 1981, *J. Am. Chem. Soc.* 103:3185–3191) or by using an automated DNA synthesizer.

An oligonucleotide can be derived synthetically or by cloning. If necessary, the 5' ends of the oligonucleotides can be phosphorylated using T4 polynucleotide kinase. Kinasing the 5' end of an oligonucleotide provides a way to label a particular oligonucleotide by, for example, attaching a radioisotope (usually $^{32}P$) to the 5' end. Subsequently, the oligonucleotide can be subjected to annealing and ligation with T4 ligase or the like.

II. Purified Torsin Polypeptides

In another embodiment, the present invention relates to a purified polypeptide preferably, substantially pure) having an amino acid sequence corresponding to a torsin protein, or a functional derivative thereof. In a preferred embodiment, the polypeptide has the amino acid sequence set forth in SEQ ID NOS: 2 or 4 or mutant or species variation thereof, or at least 80% identity or at least 90% similarity thereof (preferably, at least 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to torsin epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art (Sutcliffe et al., 1983, *Science.* 219:660–666). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15 or 20 amino acids) of the proteins of the invention. Examples of antigenic polypeptides or peptides include those listed in Table 1, below.

TABLE 1

ANTIGENIC EPITOPES

|  | Size (Number of Amino Acids) | AA Position |
|---|---|---|
| TorsinA | 5 | 50–55 |
|  | 5 | 92–96 |
|  | 6 | 225–230 |
|  | 7 | 287–293 |
|  | 6 | 315–320 |
| TorsinB | 9 | 49–57 |
|  | 3 | 133–135 |
|  | 4 | 189–192 |
|  | 7 | 275–281 |

Amino acid sequence variants of torsin can be prepared by mutations in the DNA. Such variants include, for example, deletions from, or insertions or substitutions of, residues within the amino acid sequence shown in SEQ ID NOS: 2 or 4. Any combination of deletion, insertion, and substitution can also be made to arrive at the final construct, provided that the final construct possesses the desired activity.

While the site for introducing an amino acid sequence variation is predetermined, the mutation itself need not be predetermined. For example, to optimize the performance of a particular polypeptide with respect to a desired activity, random mutagenesis can be conducted at a target codon or region of the polypeptide, and the expressed variants can be screened for the optimal desired activity. Techniques for making substitution mutations at predetermined sites in DNA having a known sequence are well known, e.g., site-specific mutagenesis.

Preparation of a torsin variant in accordance herewith is preferably achieved by site-specific mutagenesis of DNA that encodes an earlier prepared variant or a non-variant version of the protein. Site-specific mutagenesis allows the production of torsin variants through the use of specific oligonucleotide sequences that encode the DNA sequence of the desired mutation. In general, the technique of site-specific mutagenesis is well known in the art (Adelman et al., 1983, *DNA* 2:183; Ausubel, et al., In: *Current Protocols in Molecular Biology*, John Wiley & Sons, (1998)).

Amino acid sequence deletions generally range from about 1 to 30 residues, more preferably 1 to 10 residues.

Amino acid sequence insertions include amino and/or carboxyl terminal fusions from one residue to polypeptides of essentially unrestricted length, as well as intrasequence insertions of single or multiple amino acid residues. Intrasequence insertions, (i.e., insertions within the complete torsin sequence) can range generally from about 1 to 10 residues, more preferably 1 to 5.

The third group of variants are those in which at least one amino acid residue in the torsin molecule, and preferably, only one, has been removed and a different residue inserted in its place. Such substitutions preferably are made in accordance with the following Table 2 when it is desired to modulate finely the characteristics of torsin.

TABLE 2

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 2, i.e., selecting residues that differ more significantly in their effect on maintaining a) the structure of the polypeptide backbone in the area of the substitution, for example, as a sheet or helical conformation, b) the charge or hydrophobicity of the molecule at the target site, or c) the bulk of the side chain. The substitutions that in general are expected are those in which a) glycine and/or proline is substituted by another amino acid or is deleted or inserted; b) a hydrophilic residue, e.g., seryl or threonyl, is substituted for a hydrophobic residue, e.g., leucyl, isoleucyl, phenylalanyl, valyl, or alanyl; c) a cysteine residue is substituted for any other residue; d) a residue having an electropositive side chain, e.g., lysyl, arginyl, or histidyl, is substituted for a residue having an electronegative charge, e.g., glutamyl or aspartyl; or e) a residue having a bulky side chain, e.g., phenylalanine, is substituted for one not having such a side chain, e.g., glycine.

Some deletions, insertions and substitutions are not expected to produce radical changes in the characteristics of torsin. However, while it is difficult to predict the exact effect of the deletion, insertion or substitution in advance, one skilled in the art will appreciate that the effect can be evaluated by biochemical and in vivo screening assays. For example, a variant typically is made by site-specific mutagenesis of the native torsin-encoding nucleic acid, expression of the variant nucleic acid in cell culture, and, optionally, purification from the cell culture, for example, by immunoaffinity adsorption on a column (to absorb the variant by binding it to at least one immune epitope). The activity of the cell culture lysate or purified torsin variant is then screened by a suitable screening assay for the desired characteristic. For example, a change in the immunological character of the torsin molecule, such as affinity for a given antibody, can be measured by a competitive type immunoassay. Changes in immunomodulation activity can be measured by the appropriate assay. Modifications of such protein properties as redox or thermal stability, enzymatic activity, hydrophobicity, susceptibility to proteolytic degradation or the tendency to aggregate with carriers or into multimers are assayed by methods well known to those of ordinary skill in the art.

A variety of methodologies known in the art can be utilized to obtain the polypeptide of the present invention. In one embodiment, the polypeptide is purified from tissues or cells which naturally produce the peptide. Alternatively, the above described isolated nucleic acid fragments can be used to express the torsin protein in any organism. The samples of the present invention include cells, protein extracts or membrane extracts of cells, or biological fluids. The sample will vary based on the assay format, the detection method and the nature of the tissues, cells or extracts used as the sample.

Any organism can be used as a source for the polypeptide of the invention, as long as the source organism naturally contains such a peptide. As used herein, "source organism" refers to the original organism from which the amino acid sequence of the polypeptide is derived, regardless of the organism the polypeptide is expressed in and ultimately isolated from.

One skilled in the art can readily follow known methods for isolating proteins in order to obtain the polypeptide free of natural contaminants. These include, but are not limited to: immunochromotography, size-exclusion chromatography, ion-exchange chromatography, hydrophobic interaction chromatography, and non-chromatographic separation methods.

In a preferred embodiment, the purification procedures comprise ion-exchange chromatography and size exclusion chromatography. Any of a large number of ion-exchange resins known in the art can be employed, including, for example, monoQ, Sepharose-Q, macro-prepQ, AG1-X2, or HQ. Examples of suitable size exclusion resins include, but are not limited to, Superdex 200, Superose 12, and Sephycryl 200. Elution can be achieved with aqueous solutions of potassium chloride or sodium chloride at concentrations ranging from 0.01 M to 2. OM over a wide range of pH.

III. A Nucleic Acid Probe for the Specific Detection of Torsin Nucleic Acid.

In another embodiment, the present invention relates to a nucleic acid probe for the specific detection of the presence of torsin nucleic acid in a sample comprising the above-described nucleic acid molecules or at least a fragment thereof which hybridizes under stringent hybridization and wash conditions to torsin nucleic acid.

In one preferred embodiment, the present invention relates to an isolated nucleic acid probe consisting of 10 to 1000 nucleotides (preferably, 10 to 500, 10 to 100, 10 to 50, 10 to 35, 20 to 1000, 20 to 500, 20 to 100, 20 to 50, or 20 to 35) which hybridizes preferentially to torsin RNA or DNA, wherein said nucleic acid probe is or is complementary to a nucleotide sequence consisting of at least 10 consecutive nucleotides (preferably, 15, 18, 20, 25, or 30) from the nucleic acid molecule comprising a polynucleotide sequence at least 90% identical to one or more of the following: a nucleotide sequence encoding a torsin polypeptide (for example, those described by SEQ ID NOS: 2 or 4); a nucleotide sequence encoding a torsin polypeptide comprising the complete amino acid sequence encoded by the polynucleotide clone contained in ATCC Deposit No. 98454 or 98455; a nucleotide sequence complementary to any of the above nucleotide sequences; and any nucleotide sequence as previously described above.

Examples of specific nucleic acid probes which can be used in the present invention are set forth in Table 3 and in FIGS. 12 and 12B and FIGS. 14–21.

TABLE 3

NUCLEIC ACID PROBES

| | Size (no. of bases) | Nucleotides |
|---|---|---|
| TorsinA | 20 | 43–62 (SEQ ID NO: 5) |
| | 20 | 63–82 (SEQ ID NO: 5) |
| | 40 | 43–82 (SEQ ID NO: 5) |
| | 100 | 43–142 (SEQ ID NO: 5) |
| | 100 | 143–242 (SEQ ID NO: 5) |
| | 1158 | 149–1307 (SEQ ID NO: 5) |
| TorsinB | 20 | 994–1013 (SEQ ID NO: 3) |
| | 20 | 1014–1033 (SEQ ID NO: 3) |
| | 40 | 994–1033 (SEQ ID NO: 3) |
| | 100 | 994–1093 (SEQ ID NO: 3) |
| | 100 | 1094–1193 (SEQ ID NO: 3) |
| | 700 | 28–728 (SEQ ID NO: 6) |

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (Sambrook, J., Fritsch, E. F., and Maniatis, T., 1989, In: *Molecular Cloning. A Laboratory Manual.*, Cold Spring Harbor Laboratory Press, Cold Spring Harbor).

In the alternative, chemical synthesis is carried out in order to obtain nucleic acid probes having nucleotide sequences which correspond to N-terminal and C-terminal portions of the torsin amino acid sequence (Table 3). Thus, the synthesized nucleic acid probes can be used as primers in a polymerase chain reaction (PCR) carried out in accordance with recognized PCR techniques (*PCR Protocols, A Guide to Methods and Applications*, edited by Michael et al., Academic Press, 1990), utilizing the appropriate chromosomal, cDNA or cell line library to obtain the fragment of the present invention.

One skilled in the art can readily design such probes based on the sequence disclosed herein using methods of computer alignment and sequence analysis known in the art (Sambrook, J., Fritsch, E. F., and Maniatis, T., 1989, In: *Molecular Cloning. A Laboratory Manual.*, Cold Spring Harbor Laboratory Press, Cold Spring Harbor).

The hybridization probes of the present invention can be labeled for detection by standard labeling techniques such as with a radiolabeling, fluorescent labeling, biotin-avidin labeling, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the described methods will vary based on the assay format, the detection method and the nature of the tissues, cells or extracts used in the assay. Methods for preparing nucleic acid extracts of cells are well known in the art and can be readily adapted in order to obtain a sample which is compatible with the method utilized.

IV. A Method of Detecting the Presence of Torsin Nucleic Acid in a Sample.

In another embodiment, the present invention relates to a method of detecting the presence of torsin nucleic acid in a sample by contacting the sample with the above-described nucleic acid probe, under specific hybridization conditions such that hybridization occurs, and detecting the presence of the probe bound to the nucleic acid molecule. One skilled in the art would select the nucleic acid probe according to techniques known in the art as described above. Samples to be tested include but should not be limited to RNA or DNA samples from human tissue.

V. A Kit for Detecting the Presence of Torsin Nucleic Acid in a Sample.

In another embodiment, the present invention relates to a kit for detecting, in a sample, the presence of a torsin nucleic acid. The kit comprises at least one container having disposed therein the above-described nucleic acid probe. In a preferred embodiment, the kit further comprises other containers comprising wash reagents and/or reagents capable of detecting the presence of the hybridized nucleic acid probe. Examples of detection reagents include, but are not limited to radiolabeled probes, enzymatic probes (horseradish peroxidase, alkaline phosphatase), and affinity labeled probes (biotin, avidin, or streptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising a Torsin Nucleic Acid Molecule and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complementary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression can vary from organism to organism, but shall in general include a promoter region which, in prokaryotes for example, contains both the promoter, which directs the initiation of RNA transcription, as well as the DNA sequences that, when transcribed into RNA, will signal translational initiation. Such regions will normally include those 5' non-coding sequences involved with initiation of transcription and translation, such as the TATA box, capping sequence, CAAT sequence, and the like.

If desired, the non-coding region 3' to the torsin coding sequence can be obtained by the above-described methods. This region can be retained for its transcriptional termination regulatory sequences, such as termination and polyadenylation signals. Thus, by retaining the 3' region naturally contiguous to the DNA sequence encoding a torsin gene, the transcriptional termination signals are provided. Where the transcriptional termination signals are not functional in the expression host cell, then a functional 3' region derived from host sequences can be substituted.

Two DNA sequences (such as a promoter region sequence and an torsin coding sequence) are said to be operably linked if the nature of the linkage between the two DNA sequences does not (1) result in the introduction of a frameshift mutation, (2) interfere with the ability of the promoter region to direct the transcription of a torsin coding sequence, or (3) interfere with the ability of the torsin coding sequence to be transcribed by the promoter. Thus, a promoter region would be operably linked to a DNA sequence if the promoter were capable of effecting transcription of that DNA sequence.

The present invention encompasses the expression of the torsin coding sequence (or a functional derivative thereof) in either prokaryotic or eukaryotic cells. Prokaryotic hosts are, generally, the most efficient and convenient for the production of recombinant proteins. Prokaryotes most frequently are represented by various strains of $E.$ $coli$, however other microbial strains can also be used, including other bacterial strains such as those belonging to bacterial families such as $Bacillus, Streptomyces, Pseudomonas, Salmonella, Serratia$, and the like. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include λgt10, λgt11 and the like. For eukaryotic expression systems, suitable viral vectors include pMAM-neo, pKRC and the like. Preferably, the selected vector of the present invention has the capacity to replicate in the selected host cell.

To express torsin in a prokaryotic cell, it is necessary to operably link the torsin coding sequence to a functional prokaryotic promoter. Such promoters can be either constitutive or, more preferably, regulatable (i.e., inducible or derepressible). Examples of constitutive promoters include the in promoter of bacteriophage λ, the bla promoter of the β-lactamase gene, and the CAT promoter of the chloramphenicol acetyl transferase gene, and the like. Examples of inducible prokaryotic promoters include the major right and left promoters of bacteriophage λ ($P_L$ and $P_R$), the trp, recA, lacZ lacI, and gal promoters of $E.$ $coli$, the α-amylase (Ulmanen et al., 1985, $J.$ $Bacteriol.$ 162:176–182) and the ζ-28-specific promoters of $B.$ $subtilis$ (Gilman et al., 1984, $Gene$ $sequence$ 32:11–20), the promoters of the bacteriophages of $B.$ $subtilis$ (Gryczan, In: $The$ $Molecular$ $Biology$ $of$ $the$ $Bacilli$, Academic Press, Inc., N.Y. (1982)), and $Streptomyces$ promoters (Ward, et al., 1986, $Mol.$ $Gen.$ $Genet.$ 203:468–478).

Proper expression in a prokaryotic cell also requires the presence of a ribosome binding site upstream of the gene sequence-encoding sequence (Gold et al., 1981, $Ann.$ $Rev.$ $Microbiol.$ 35:365–404).

The selection of control sequences, expression vectors, transformation methods, and the like, is dependent on the type of host cell used to express the gene. The terms "transformants" or "transformed cells" include the primary subject cell and cultures derived therefrom, without regard to the number of transfers. It is also understood that all progeny cannot be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of the torsin peptide of interest. Suitable hosts include eukaryotic cells. Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells, such as the cauliflower mosaic virus 35S and 19S, nopaline synthase promoter and polyadenylation signal sequences are available.

Another preferred host is an insect cell, for example $Drosophila$ $melanogaster$ larvae. Using insect cells as hosts, the $Drosophila$ alcohol dehydrogenase promoter can be used (Rubin, 1988, $Science.$ 240:1453–1459). Alternatively, baculovirus vectors can be engineered to express large amounts of torsin protein in insect cells (Jasny, 1987, $Science.$ 238:1653; Miller et al., In: $Genetic$ $Engineering$ (1986), Setlow, J. K., et al., Eds., $Plenum$, Vol. 8, pp. 277–297).

Different host cells have characteristic and specific mechanisms for the translational and post-translational processing and modification (e.g., glycosylation and cleavage) of proteins. Appropriate cell lines or host systems can be chosen to ensure the desired modification of the foreign protein expressed.

Any of a series of yeast gene expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast provides substantial advantages over prokaryotes in that it can perform post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

For a mammalian host, several possible vector systems are available for the expression of torsin. A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of torsin in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer, et al., 1982, *J. Mol. Appl. Gen.* 1:273–288); the TK promoter of herpes virus (McKnight, 1982, *Cell.* 31:355–365); the SV40 early promoter (Benoist, et al., 1981, *Nature.* 290:304–310); the yeast gal4 gene promoter (Johnston, et al., 1982, *Proc. Nat. Acad Sci. USA* 79:6971–6975; Silver, et al., 1984, *Proc. Natl. Acad. Sci. USA* 81:595 1 5955) and the CMV immediate-early gene promoter (Thomsen, et al., 1984, *Proc. Natl. Acad. Sci. USA* 81:659–663).

As is widely known, translation of eukaryotic mRNA is initiated at a codon which encodes methionine. For this reason, it is preferable to ensure that the linkage between a eukaryotic promoter and a torsin coding sequence does not contain any intervening codons which are capable of encoding a methionine (i.e., AUG). The presence of such codons results either in a formation of a fusion protein (if the AUG codon is in the same reading frame as the torsin coding sequence) or a frame-shift mutation (if the AUG codon is not in the same reading frame as the torsin coding sequence).

A torsin nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected on the basis of one or more markers which allow for selection of host cells which contain the expression vector. Such markers can provide, for example, for autotrophy to an auxotrophic host or for biocide resistance, e.g., to antibiotics or to heavy metal poisoning, such as by copper, or the like. The selectable marker gene sequence can either be contained on the vector of the DNA gene to be expressed, or introduced into the same cell by co-transfection. Additional elements might also be necessary for optimal synthesis of mRNA. These elements can include splice signals, as well as transcription promoters, enhancer signal sequences, and termination signals. cDNA expression vectors incorporating such elements have been described (Okayama, 1983, *Molec. Cell Biol.* 3:280).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells that do not contain the vector; the desired number of copies of the vector present in the host cell; and the ability to "shuttle" the vector between host cells of different species, i.e., between mammalian cells and bacteria. Preferred prokaryotic vectors include plasmids such as those capable of replication in *E. coli* (for example, pBR322, ColE1, pSC101, pACYC 184, and πVX). Such plasmids are commonly known to those of skill in the art (Sambrook, J., Fritsch, E. F., and Maniatis, T., 1989, In: *Molecular Cloning. A Laboratory Manual.*, Cold Spring Harbor Laboratory Press, Cold Spring Harbor). *B. subtilis* derived plasmids include pC194, pC221, pT127, and the like (Gryczan, In: *The Molecular Biology of the Bacilli*, Academic Press, NY (1982), pp. 307–329). Suitable *Streptomyces* plasmids include pIJ101 (Kendall, et al., 1987, *J. Bacteriol.* 169:4177–4183), and streptomyces bacteriophages such as φC31 (Chater, et al., In: *Sixth International Symposium on Actinomycetales Biology*, Akademiai Kaido, Budapest, Hungary (1986), pp. 45–54). *Pseudomonas* plasmids have also been described (John, et al., 1986, Rev. *Infect. Dis.* 8:693–704; Izaki, 1978, *Jpn. J. Bacteriol.* 33:729–742).

Preferred eukaryotic plasmids include, for example, BPV, vaccinia, SV40, 2μ circle, and the like, or their derivatives. Such plasmids are well known in the art (Botstein, et al., 1982, *Miami Wntr. Symp.* 19:265–274; Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, 1982, *Cell.* 28:203–204; Bollon, et al, 1980, *J. Clin. Hematol. Oncol.* 10:39–48; Maniatis, In: *Cell Biology: A Comprehensive Treatise*, Vol. 3, Gene Sequence Expression, Academic Press, NY, pp. 563–608 (1980)).

Once the vector or nucleic acid molecule containing the construct has been prepared for expression, the DNA construct can be introduced into an appropriate host cell by any of a variety of suitable means, i.e., transformation, transfection, lipofection, conjugation, protoplast fusion, electroporation, particle gun technology, calcium phosphate precipitation, direct microinjection, and the like. After the introduction of the vector, recipient cells are grown in a selective medium that allows for selection of vector containing cells. Expression of the cloned gene results in the production of torsin. This can take place in the transformed cells as such, or following the induction of these cells to differentiate (for example, by administration of bromodeoxyuracil to neuroblastoma cells or the like).

VII. An Antibody Having Binding Affinity to a Torsin Polypeptide and a Hybridoma Containing the Antibody.

In another embodiment, the present invention relates to an antibody having binding affinity specifically to a torsin polypeptide as described above or specifically to a torsin polypeptide binding fragment thereof. An antibody binds specifically to a torsin polypeptide or binding fragment thereof if it does not bind to non-torsin polypeptides. Those which bind selectively to torsin would be chosen for use in methods which could include, but should not be limited to, the analysis of altered torsin expression in tissue containing torsin.

The torsin proteins of the present invention can be used in a variety of procedures and methods, such as for the generation of antibodies, for use in identifying pharmaceutical compositions, and for studying DNA/protein interaction.

The torsin peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to torsin which are produced in humans, or are "humanized" (i.e., non-immunogenic in a human) by recombinant or other technology. Humanized antibodies can be produced, for example by replacing an immunogenic portion of an antibody with a corresponding, but non-immunogenic portion (i.e., chimeric antibodies (Robinson, R. R., et al., International Patent Publication PCT/US86/02269; Akira, K., et al., European Patent Application 184,187; Taniguchi, M., European Patent Application 171,496; Morrison, S. L., et al., European Patent Application 173,494; Neuberger, M. S., et al., PCT Application WO 86/01533; Cabilly, S., et al., European Patent Application 125,023; Better, M., et al, 1988, *Science*. 240:1041–1043; Liu, A. Y., et al., 1987, *Proc. Natl. Acad. Sci. USA*. 84:3439–3443; Liu, A. Y., et al., 1987, *J. Immunol*. 139:3521–3526; Sun, L. K., et al., 1987, *Proc. Natl. Acad. Sci*. USA 84:214–218; Nishimura, Y., et al., 1987, *Canc. Res*. 47:999–1005; Wood, C. R., et al., 1985, *Nature*. 314:446–449); Shaw, et al., 1988, *J. Natl. Cancer Inst*. 80:1553–1559) and "humanized" chimeric antibodies (Morrison, S. L., 1985, *Science*. 229:1202–1207; Oi, V. T., et al., 1986, *BioTechniques* 4:214)). Suitable "humanized" antibodies can be alternatively produced by CDR or CEA substitution (Jones, P. T., et al., 1986, *Nature*. 321:552–525; Verhoeyan, et al., 1988, *Science*. 239:1534; Beidler, C. B., et al., 1988, *J. Immunol*. 141:4053–4060).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth, et al., 1980, *J. Immunol. Methods*. 35:1–21).

The inventive methods utilize antibodies reactive with torsinA or portions thereof. In a preferred embodiment, the antibodies specifically bind with torsinA or a portion or fragment thereof. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas by an ELISA assay, Western blot analysis, or radioimmunoassay (Lutz, et al., 1988, *Exp. Cell Res*. 175:109–124).

Hybridomas secreting the desired antibodies are cloned and the class and subclass is determined using procedures known in the art (Campbell, In: *Monoclonal Antibody Technology. Laboratory Techniques in Biochemistry and Molecular Biology, supra* (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art (Stemberger, et al., 1970, *J. Histochem. Cytochem*. 18:315; Bayer, et al., 1979, *Meth. Enzym*. 62:308; Engval, et al., 1972, *Immunol*. 109:129; Goding, 1976, *J. Immunol. Meth*. 13:215). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, et al., In: "*Handbook of Experimental Immunology,*" 4th Ed., Blackwell Scientific Publications, Oxford, England, Chapter 10 (1986); Jacoby, et al., 1974, *Meth. Enzym*. Vol. 34. Academic Press, N.Y.). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides (Hurby, et al., In: "Application of Synthetic Peptides: Antisense Peptides," In *Synthetic Peptides, A User's Guide*, W. H. Freeman, NY, pp. 289–307 (1992); Kaspczak, et al., 1989, *Biochemistry* 28:9230–9238).

Anti-peptide peptides can be generated in one of two fashions. First, the anti-peptide peptides can be generated by replacing the basic amino acid residues found in the torsin peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting a Torsin Polypeptide or Antibody in a Sample.

In another embodiment, the present invention relates to a method of detecting a torsin polypeptide in a sample, comprising: contacting the sample with an above-described antibody (or protein), under conditions such that immunocomplexes form, and detecting the presence of the antibody bound to the polypeptide. In detail, the methods comprise incubating a test sample with one or more of the antibodies of the present invention and assaying whether the antibody binds to the test sample. Altered levels of torsin in a sample as compared to normal levels can indicate a specific disease.

In a further embodiment, the present invention relates to a method of detecting a torsin antibody in a sample, comprising: contacting the sample with an above-described torsin protein, under conditions such that immunocomplexes form, and detecting the presence of the protein bound to the antibody or antibody bound to the protein. In detail, the methods comprise incubating a test sample with one or more of the proteins of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention (Chard, In: *An Introduction to Radioimmunoassay and Related Techniques*, Elsevier Science Publishers, Amsterdam, The Netherlands (1986); Bullock, et al., In: *Techniques in Immunocytochemistry*, Academic Press, Orlando, Fla. Vol. 1(1982), Vol. 2(1983), Vol. 3(1985); Tijssen, In: *Practice and Theory of enzyme Immunoassays: Laboratory Techniques in Biochemistry and Molecular Biology*, Elsevier Science Publishers, Amsterdam, The Netherlands (1985)).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

The claimed invention utilizes several suitable assays which can measure dystonia proteins such as torsinA. Suitable assays encompass immunological methods, such as radioimmunoassay, enzyme-linked immunosorbent assays (ELISA), and chemiluminescence assays. Any method known now or developed later can be used for performing the invention and measuring torsinA.

In several of the preferred embodiments, immunological techniques detect torsinA levels by means of an anti-torsinA antibody (i.e., one or more antibodies) which includes monoclonal and/or polyclonal antibodies, and mixtures thereof. For example, these immunological techniques can utilize mixtures of polyclonal and/or monoclonal antibodies, such as a cocktail of murine monoclonal and rabbit polyclonal.

One of skill in the art can raise anti-torsin antibodies against an appropriate immunogen, such as isolated and/or recombinant torsinA or a portion or fragment thereof (including synthetic molecules, such as synthetic peptides). In one embodiment, antibodies are raised against an isolated and/or recombinant torsinA or a portion or fragment thereof (e.g., a peptide) or against a host cell which expresses recombinant torsin. In addition, cells expressing recombinant torsinA, such as transfected cells, can be used as immunogens or in a screen for antibodies which bind torsinA.

Any suitable technique can prepare the immunizing antigen and produce polyclonal or monoclonal antibodies. The prior art contains a variety of these methods (Köhler, et al., 1975, *Nature.* 256:495–497; Köhler, et al., 1976, *Eur. J. Immunol.* 6:511–519; Milstein, et al., 1977, *Nature.* 266:550–552; Koprowski, et al., U.S. Pat. No. 4,172,124; Harlow, et al., In: *Antibodies: A Laboratory Manual*, Cold Spring Harbor Laboratory: Cold Spring Harbor, N.Y. (1988)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce well established art recognized assays such as ELISA, RIA and Western blotting can be used to select antibody producing cells with the desired specificity.

Other suitable methods can produce or isolate antibodies of the requisite specificity. Examples of other methods include selecting recombinant antibody from a library or relying upon immunization of transgenic animals such as mice which are capable of producing a full repertoire of human antibodies (Jakobovits, et al., 1993, *Proc. Natl. Acad. Sci. USA* 90:2551–2555; Jakobovits, et al., 1993, *Nature.* 362:255–258; Lonbert, et al., U.S. Pat. No. 5,545,806; Surani, et al., U.S. Pat. No. 5,545,807).

According to the method, an assay can determine the level or concentration of torsinA in a biological sample. In determining the amounts of torsinA, an assay includes combining the sample to be tested with an antibody having specificity for torsinA, under conditions suitable for formation of a complex between antibody and torsinA, and detecting or measuring (directly or indirectly) the formation of a complex. The sample can be obtained and prepared by a method suitable for the particular sample (e.g., whole blood, tissue extracts, serum) and assay format selected. For example, suitable methods for whole blood collection are venipuncture or obtaining blood from an indwelling arterial line. The container to collect the blood can contain an anti-coagulant such as CACD-A, heparin, or EDTA. Methods of combining sample and antibody, and methods of detecting complex formation are also selected to be compatible with the assay format. Suitable labels can be detected directly, such as radioactive, fluorescent or chemiluminescent labels; or indirectly detected using labels such as enzyme labels and other antigenic or specific binding partners like biotin and colloidal gold. Examples of such labels include fluorescent labels such as fluorescein, rhodamine, CY5, APC, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels and the like. The detection of antibodies in a complex can also be done immunologically with a second antibody which is then detected. Conventional methods or other suitable methods can directly or indirectly label an antibody.

IX. A Diagnostic Kit Comprising Torsin Protein or Antibody.

In another embodiment of the present invention, a kit is provided for diagnosing the presence or absence of a dystonia; or the likelihood of developing a dystonia in a mammal which contains all the necessary reagents to carry out the previously described methods of detection.

For example, the kit can comprise a first container means containing an above described antibody, and a second container means containing a conjugate comprising a binding partner of the antibody and a label.

The kit can also comprise a first container means containing an above described protein, and preferably a second container means containing a conjugate comprising a binding partner of the protein and a label. More specifically, a diagnostic kit comprises torsin protein as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits. The kit can be, for example, a RIA kit or an ELISA kit.

One skilled in the art will readily recognize that the antibodies described in the present invention can readily be incorporated into one of the established kit formats which are well known in the art.

X. Diagnostic Screening and Treatment.

It is to be understood that although the following discussion is specifically directed to human patients, the teachings are also applicable to any mammal that expresses a dystonia protein, such as torsinA or torsinB. The term "mammalian," as defined herein, refers to any vertebrate animal, including monotremes, marsupials and placental, that suckle their young and either give birth to living young (eutherian or placental mammals) or are egg-laying (metatherian or nonplacental mammals). Examples of mammalian species include primates (e.g., humans, monkeys, chimpanzees, baboons), rodents (e.g., rats, mice, guinea pigs, hamsters) and ruminants (e.g., cows, horses).

The diagnostic and screening methods of the present invention encompass detecting the presence, or absence of, a mutation in a gene wherein the mutation in the gene results in a neuronal disease in a human. For example, the diagnostic and screening methods of the present invention are especially useful for diagnosing the presence or absence of a mutation or polymorphism in a neuronal gene in a human patient, suspected of being at risk for developing a disease associated with an altered expression level of torsin based on family history, or a patient in which it is desired to diagnose a torsin-related disease.

Preferably, nucleic acid diagnosis is used as a means of differential diagnosis of various forms of a torsion dystonia such as early-onset generalized dystonia; late-onset generalized dystonia; or any form of genetic, environmental, primary or secondary dystonia. This information is then used in genetic counseling and in classifying patients with respect to individualized therapeutic strategies.

According to the invention, presymptomatic screening of an individual in need of such screening is now possible using DNA encoding the torsin protein of the invention. The screening method of the invention allows a presymptomatic diagnosis, including prenatal diagnosis, of the presence of a missing or aberrant torsin gene in individuals, and thus an opinion concerning the likelihood that such individual would develop or has developed a torsin-associated disease. This is especially valuable for the identification of carriers of altered or missing torsin genes, for example, from individuals with a family history of a torsin-associated disease. Early diagnosis is also desired to maximize appropriate timely intervention.

Identification of gene carriers prior to onset of symptoms allows evaluation of genetic and environmental factors that trigger onset of symptoms. Modifying genetic factors could include polymorphic variations in torsin proteins (specifically, torsinA) or mutations in related or associated proteins; environmental factors include sensory overload to the part of body subserved by susceptible neurons, such as that caused by overuse or trauma (Gasser, T., et al., 1996, Mov Disord. 11:163–166); high body temperature; or exposure to toxic agents.

In one embodiment of the diagnostic method of screening, a test sample comprising a bodily fluid (e.g., blood, saliva, amniotic fluid) or a tissue (e.g., neuronal, chorionic villous) sample would be taken from such individual and screened for (1) the presence or absence of the "normal" torsin gene; (2) the presence or absence of torsin mRNA and/or (3) the presence or absence of torsin protein. The normal human gene can be characterized based upon, for example, detection of restriction digestion patterns in "normal" versus the patients DNA, including RFLP, PCR, Southern blot, Northern blot and nucleic acid sequence analysis, using DNA probes prepared against the torsin sequence (or a functional fragment thereof) taught in the invention. In one embodiment the torsin sequence is the DYT1 sequence (SEQ ID NO: 1). In another embodiment the presence or absence of three nucleotides is indicative of a negative or positive diagnosis, respectively, of a torsion dystonia. In yet another aspect of the invention the presence or absence of an A and two Gs from a GAGGAG region of SEQ ID NO: 5 which results in GAG nucleotides remaining in the gene, is indicative of a negative or positive diagnosis, prognosis or likelihood of developing a torsion dystonia. For example, the presence or absence of nucleotides at positions 946–948; 947–949; 948–950; or 949–951, of SEQ ID NO: 5 are indicative of a negative or positive diagnosis, respectively. Similarly, torsin mRNA can be characterized and compared to normal torsin mRNA (a) levels and/or (b) size as found in a human population not at risk of developing torsin-associated disease using similar probes. Additionally or alternatively, nucleic acids can be sequenced to determine the presence or absence of a "normal" torsin gene. Nucleic acids can be DNA (e.g., cDNA or genomic DNA) or RNA.

Lastly, torsin protein can be (a) detected and/or (b) quantitated using a biological assay for torsin activity or using an immunological assay and torsin antibodies. When assaying torsin protein, the immunological assay is preferred for its speed. In one embodiment of the invention the torsin protein is torsinA (SEQ ID NO: 2) or a protein encoded by SEQ ID NO: 1. An (1) aberrant torsin DNA size pattern, and/or (2) aberrant torsin mRNA sizes or levels and/or (3) aberrant torsin protein levels would indicate that the patient is at risk for developing a torsin-associated disease.

Mutations associated with a dystonia disorder include any mutation in a dystonia gene, such as DYT1. The mutations can be the deletion or addition of at least one nucleotide in the coding or noncoding region, of the DYT1 gene which result in a change in a single amino acid or in a frame shift mutation.

Mutations associated with a torsion dystonia also include a deletion of three nucleotides of the DYT1 gene, specifically the deletion of nucleotides 946–948; 949–951; 947–949; 948–950 or any combination thereof from a GAG-GAG region of SEQ ID NO: 5.

In one method of diagnosing the presence or absence of a dystonia disorder, hybridization methods, such as Southern analysis, are used (Ausubel, et al., In: *Current Protocols in Molecular Biology*, John Wiley & Sons, (1998)). Test samples suitable for use in the present invention encompass any sample containing nucleic acids, either DNA or RNA. For example, a test sample of genomic DNA is obtained from a human suspected of having (or carrying a defect for) the dystonia disorder. The test sample can be from any source which contains genomic DNA, such as a bodily fluid or tissue sample. In one embodiment, the test sample of DNA is obtained from bodily fluids such as blood, saliva, semen, vaginal secretions, cerebrospinal and amniotic bodily fluid samples. In another embodiment, the test sample of DNA is obtained from tissue such as chorionic villous, neuronal, epithelial, muscular and connective tissue. DNA can be isolated from the test samples using standard, art-recognized protocols (Breakefield, X. O., et al., 1986, *J. Neurogenetics*. 3:159–175). The DNA sample is examined to determine whether a mutation associated with a dystonia disorder is present or absent. The presence or absence of a mutation or a polymorphism is indicated by hybridization with a neuronal gene, such as the DYT1 gene, in the genomic DNA to a nucleic acid probe. A nucleic acid probe is a nucleotide sequence of a neuronal gene. For example, the nucleic acid probe can be a region of exon 5 of the DYT1 gene SEQ ID NOS: 27–29 or SEQ ID NOS: 30–39. Additionally or alternatively, RNA encoded by such a probe can also be used.

To diagnose the presence or absence of a dystonia disorder by hybridization, a hybridization sample is formed by contacting the test sample containing a dystonia gene, such as DYT1, with a nucleic acid probe. The hybridization sample is maintained under conditions which are sufficient to allow specific hybridization of the nucleic acid probe to the dystonia gene of interest.

Specific hybridization can be detected under high stringency conditions. "Stringency conditions" for hybridization is a term of art which refers to the conditions of temperature and buffer concentration which permit and maintain hybridization of a particular nucleic acid to a second nucleic acid; the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations and subsequent washes are explained on pages 2.10.1–2.10.16 and pages 6.3.1–6 in Current Protocols in Molecular Biology (Ausubel, et al., In: *Current Protocols in Molecular Biology*, John Wiley & Sons, (1998)) the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in the art (Krause, M. H., et al., 1991, *Methods Enzymol*. 200:546–556). Also, low and moderate stringency conditions for washes are described (Ausubel, et al., In: *Current Protocols in Molecular Biology*, John Wiley & Sons, (1998)). Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

Specific hybridization between the sample and the nucleic acid probe is then detected using standard methods. More than one dystonia gene (e.g., DYT1) nucleic acid probe can also be used concurrently in this method, Specific hybridization of any one of the nucleic acid probes to two alleles of the DYT1 is diagnostic of the absence of the torsion dystonia whereas specific hybridization to one allele of the DYT1 gene is diagnostic for the presence of the torsion dystonia.

Other hybridization methods such as Northern analysis or slot blot analysis (Ausubel, et al., In: *Current Protocols in Molecular Biology*, John Wiley & Sons, (1998)) are used to diagnose a torsion dystonia. For Northern analysis or slot blot analysis, a sample of RNA is obtained from the human. Specific hybridization of a DYT1 nucleic acid probe, as described above, to RNA from the individual is indicative of the presence or absence of a mutation in the DYT1 gene that is associated with torsion dystonia and is, therefore, diagnostic for the disorder.

In another embodiment of the invention, deletion analysis by restriction digestion can be used to detect a deletion in a dystonia gene, such as the DYT1 gene, if the deletion in the gene results in the creation or elimination of a restriction site. For example, a test sample containing genomic DNA is obtained from the human. After digestion of the genomic DNA with an appropriate restriction enzyme, DNA fragments are separated using standard methods, and contacted with a probe specific for the DYT1 gene (e.g., SEQ ID NOS: 28 and 29) or cDNA. The digestion pattern of the DNA fragments indicates the presence or absence of the mutation associated with a dystonia disorder. Alternatively, polymerase chain reaction (PCR) can be used to amplify the dystonia gene of interest, such as DYT1, (and, if necessary, the flanking sequences) in a test sample of genomic DNA from the human. Direct mutation analysis by restriction digestion or nucleotide sequencing is then conducted. The digestion pattern of the relevant DNA fragment indicates the presence or absence of the mutation associated with the dystonia disorder. The presence of the nucleotides GAGGAG, in the region of SEQ ID NO: 5, is diagnostic and predictive of the absence of a torsion dystonia, whereas the absence of a GAG, for example, in the nucleotide sequence is diagnostic and predictive of the presence of a torsion dystonia. It is appreciated that any other mutations in a torsin gene or dystonia protein would be within the scope of the invention and could be used in methods of diagnosing, prognosing and predicting the presence or absence of a neuronal disease, for example a movement disorder, for example torsion dystonia.

Allele-specific oligonucleotides can also be used to detect the presence or absence of a neuronal disease by detecting a deletion or a polymorphism associated with a particular disease by PCR amplification of a nucleic acid sample from a human with allele-specific oligonucleotide probes. An "allele-specific oligonucleotide" (also referred to herein as an "allele-specific oligonucleotide probe") is an oligonucleotide of approximately 10–300 base pairs, that specifically hybridizes to a dystonia gene, such as DYT1, (or gene fragment) that contains a particular mutation, such as a deletion of three nucleotides. An allele-specific oligonucleotide probe that is specific for particular mutation in, for example, the DYT1 gene, can be prepared, using standard methods (Ausubel, et al., In: *Current Protocols in Molecular Biology*, John Wiley & Sons, (1998)). To identify mutations in the DYT1 gene associated with torsion dystonia, or any other neuronal disease a test sample of DNA is obtained from the human. PCR can be used to amplify all or a fragment of the DYT1 gene, and its flanking sequences. PCR primers comprise any sequence of a neuronal gene, for example, PCR primers can comprise nucleic acid sequences of an intron or exon of the DYT1 gene (SEQ ID NOS: 27–29; SEQ ID NOS 30–39). The PCR products containing the amplified neuronal gene, for example a DYT 1 gene (or fragment of the gene), are separated by gel electrophoresis using standard methods (Ausubel, et al., In: *Current Protocols in Molecular Biology*, John Wiley & Sons, (1998)), and fragments visualized using art-recognized, well-established techniques such as fluorescent imaging when fluorescently labeled primers are used. The presence or absence of specific DNA fragments indicative of the presence or absence of a mutation or a polymorphism in a neuronal gene are then detected. For example, the presence of two alleles of a specific molecular size is indicative of the absence of a torsion dystonia; whereas the absence of one of these alleles is indicative of a torsion dystonia. The samples obtained from humans and evaluated by the methods described herein will be compared to standard samples that do and do not contain the particular mutations or polymorphism which are characteristic of the particular neuronal disorder (see Example 5).

For example, a method of diagnosing the presence or predisposition to develop torsion dystonia in a patient is provided herein. The method comprises obtaining a sample from the human; evaluating the characteristics of torsinA nucleic acid in the sample, wherein the evaluation comprises detecting the GAGGAG region (SEQ ID NO: 5 at nucleotide positions 946–951) in the sample; and diagnosing the presence or predisposition to develop torsion dystonia in a patient wherein the absence of GAG from the GAGGAG region indicates the presence or predisposition to develop torsion dystonia.

The screening and diagnostic methods of the invention do not require that the entire torsin DNA coding sequence be used for the probe. Rather, it is only necessary to use a fragment or length of nucleic acid that is sufficient to detect the presence of the torsin gene in a DNA preparation from a normal or affected individual, the absence of such gene, or an altered physical property of such gene (such as a change in electrophoretic migration pattern). For example, a region of exon 5 of DYT1 nucleic acids of at least 15 (e.g., 20, 21, 25, 30, 35, 45 50) consecutive nucleic acids can be used as a probe or as the sequence for primers in PCR amplifications strategies.

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal torsin gene is present in a heterozygous state.

In the method of treating a torsin-associated disease in a patient in need of such treatment, functional torsin DNA can be provided to the cells of such patient in a manner and amount that permits the expression of the torsin protein provided by such gene, for a time and in a quantity sufficient to treat such patient. Many vector systems are known in the art to provide such delivery to human patients in need of a gene or protein missing from the cell. For example, retrovirus systems can be used, especially modified retrovirus systems and especially herpes simplex virus systems (Breakefield, X. O., et al., 1991, *New Biologist.* 3:203–218; Huang, Q., et al., 1992, *Experimental Neurology.* 115:303–316; W093/03743; W090/09441). Delivery of a DNA sequence encoding a functional torsin protein will effectively replace the missing or mutated torsin gene of the invention.

In another embodiment of this invention, the torsin gene is expressed as a recombinant gene in a cell, so that the cells can be transplanted into a mammal, preferably a human in need of gene therapy. To provide gene therapy to an individual, a genetic sequence which encodes for all or part of the torsin gene is inserted into a vector and introduced into a host cell. Examples of diseases that can be suitable for gene therapy include, but are not limited to, neurodegenerative diseases or disorders, primary dystonia (preferably, generalized dystonia and torsion dystonia).

Gene therapy methods can be used to transfer the torsin coding sequence of the invention to a patient (Chattedee and Wong, 1996, *Curr. Top. Microbiol. Immunol.* 218:61–73; Zhang, 1996, *J. Mol. Med.* 74:191–204; Schmidt-Wolf and Schmidt-Wolf, 1995, *J. Hematotherapy.* 4:551–561; Shaughnessy, et al., 1996, *Seminars in Oncology.* 23:159–171; Dunbar, 1996,*Annu. Rev. Med.* 47:11–20).

Examples of vectors that may be used in gene therapy include, but are not limited to, defective retroviral, adenoviral, or other viral vectors (Mulligan, R. C., 1993, *Science.* 260:926–932). The means by which the vector carrying the gene can be introduced into the cell include but is not limited to, microinjection, electroporation, transduction, or transfection using DEAE-Dextran, lipofection, calcium phosphate or other procedures known to one skilled in the art (Sambrook, J., Fritsch, E. F., and Maniatis, T., 1989, In: *Molecular Cloning. A Laboratory Manual.*, Cold Spring Harbor Laboratory Press, Cold Spring Harbor).

The ability of antagonists and agonists of torsin to interfere or enhance the activity of torsin can be evaluated with cells containing torsin. An assay for torsin activity in cells can be used to determine the functionality of the torsin protein in the presence of an agent which may act as antagonist or agonist, and thus, agents that interfere or enhance the activity of torsin are identified.

The agents screened in the assays can be, but are not limited to, peptides, carbohydrates, vitamin derivatives, or other pharmaceutical agents. These agents can be selected and screened at random, by a rational selection or by design using, for example, protein or ligand modeling techniques (preferably, computer modeling).

For random screening, agents such as peptides, carbohydrates, pharmaceutical agents and the like are selected at random and are assayed for their ability to bind to or stimulate/block the activity of the torsin protein.

Alternatively, agents may be rationally selected or designed. As used herein, an agent is said to be "rationally selected or designed" when the agent is chosen based on the configuration of the torsin protein.

In one embodiment, the present invention relates to a method of screening for an antagonist or agonist which stimulates or blocks the activity of torsin comprising incubating a cell expressing torsin with an agent to be tested; and assaying the cell for the activity of the torsin protein by measuring the agents effect on ATP binding of torsin.

Any cell may be used in the above assay so long as it expresses a functional form of torsin and the torsin activity can be measured. The preferred expression cells are eukaryotic cells or organisms. Such cells can be modified to contain DNA sequences encoding torsin using routine procedures known in the art. Alternatively, one skilled in the art can introduce mRNA encoding the torsin protein directly into the cell.

In another embodiment, the present invention relates to a screen for pharmaceuticals (e.g., drugs) which can counteract the expression of a mutant torsin protein. Preferably, a neuronal culture is used for the overexpression of the mutant form of torsinA using the vector technology described herein. Changes in neuronal morphology and protein distribution is assessed and a means of quantification is used. This bioassay is then used as a screen for drugs which can ameliorate the phenotype.

Using torsin ligands (including antagonists and agonists as described above) the present invention further provides a method for modulating the activity of the torsin protein in a cell. In general, agents (antagonists and agonists) which have been identified to block or stimulate the activity of torsin can be formulated so that the agent can be contacted with a cell expressing a torsin protein in vivo. The contacting of such a cell with such an agent results in the in vivo modulation of the activity of the torsin proteins. So long as a formulation barrier or toxicity barrier does not exist, agents identified in the assays described above will be effective for in vivo use.

In another embodiment, the present invention relates to a method of administering torsin or a torsin ligand (including torsin antagonists and agonists) to an animal (preferably, a mammal (specifically, a human)) in an amount sufficient to effect an altered level of torsin in the animal. The administered torsin or torsin ligand could specifically effect torsin associated functions. Further, since torsin is expressed in brain tissue, administration of torsin or torsin ligand could be used to alter torsin levels in the brain.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of torsin or torsin ligand, in one or more administrations daily, for one or several days. Torsin or torsin ligand can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like (*Remington's Pharmaceutical Science*, 16th ed., Eds.: Osol, A., Ed., Mack, Easton Pa. (1980)).

In another embodiment, the present invention relates to a pharmaceutical composition comprising torsin or torsin ligand in an amount sufficient to alter is torsin associated activity, and a pharmaceutically acceptable diluent, carrier, or excipient. Appropriate concentrations and dosage unit sizes can be readily determined by one skilled in the art as described above (*Remington's Pharmaceutical Sciences*, 16th ed., Eds.: Osol, A., Ed., Mack, Easton Pa. (1980); WO 91/19008).

XI. Transgenic Torsin "Knock-Out" Mice.

Methods of Generating Transgenic Non-Human Animals

The non-human animals of the invention comprise any animal having a transgenic interruption or alteration of the endogenous gene(s) (knock-out animals) and/or into the genome of which has been introduced one or more transgenes that direct the expression of human torsin.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i. e., by human manipulation), one or more genes that do not occur naturally in the animal, e.g., foreign genes, genetically engineered endogenous genes, etc. The non-naturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene (Watson, J. D., et al., In: *Recombinant DNA*, 2d Ed., W. H. Freeman & Co., New York (1992), pg. 255–272; Gordon, J. W., 1989, *Intl. Rev. Cytol.* 115:171–229;

Jaenisch, R., 1989, *Science.* 240:1468–1474; Rossant, J., 1990, *Neuron.* 2:323–334).

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

Microinjection of zygotes is the preferred method for incorporating transgenes into animal genome in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 pL of a solution containing transgenic DNA sequences. The use of a zygote for introduction of transgenes has the advantage that, in most cases, the injected transgenic DNA sequences will be incorporated into the host animal's genome before the first cell division (Brinster, et al., 1985, *Proc. Natl. Acad. Sci.* USA 82:4438–4442). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

Viral integration can also be used to introduce the transgenes of the invention into an animal. The developing embryos are cultured in vitro to the developmental stage known as a blastocyst. At this time, the blastomeres may be infected with appropriate retroviruses (Jaenisch, R., 1976, *Proc. Natl. Acad. Sci.* USA 73:1260–1264). Infection of the blastomeres is enhanced by enzymatic removal of the zona pellucida (Hogan, et al., In: *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., 1985, *Proc. Natl. Acad. Sci.* USA 82:6927–6931; van der Putten, et al., 1985, *Proc. Natl. Acad. Sci.* USA 82:6148–6152). Transfection is easily and efficiently obtained by culture of blastomeres on a mono-layer of cells producing the transgene-containing viral vector (van der Putten, et al., 1985, *Proc. Natl. Acad. Sci.* USA 82:6148–6152; Stewart, et al., 1987, *EMBO J.* 6:383–388). Alternatively, infection may be performed at a later stage, such as a blastocoele (Jahner, D., et al., 1982, *Nature.* 298:623–628). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., 1982, *Nature.* 298:623–628). However, once a transgene has been introduced into germline cells by this method, offspring may be produced in which the transgenic allele is present in all of the animal's cells, i.e., in both somatic and germline cells.

Embryonic stem (ES) cells can also serve as target cells for introduction of the transgenes of the invention into animals. ES cells are obtained from pre-implantation embryos that are cultured in vitro (Evans, M. J., et al., 1981, *Nature.* 292:154–156; Bradley, M. O., et al., 1984, *Nature.* 309:255–258; Gossler, et al., 1986, *Proc. Natl. Acad. Sci.* USA 83:9065–9069; Robertson, E. J., et al., 1986, *Nature.* 322:445–448; Robertson, E. J., In: *Teratocarcinomas and Embryonic Stem Cells: A Practical, Approach*, Ed.: Robertson, E. J., IRL Press, Oxford (1987), pg. 71–112). ES cells, which are commercially available (from, e.g., Genome Systems, Inc., St. Louis, Mo.), can be transformed with one or more transgenes by established methods (Lovell-Badge, R. H., In: *Teratocarcinomas and Embryonic Stem Cells: A Practical Approach*, Ed.: Robertson, E. J., IRL Press, Oxford (1987), pg. 153–182). Transformed ES cells can be combined with an animal blastocyst, after which the ES cells colonize the embryo and contribute to the germline of the resulting animal, which is a chimera composed of cells derived from two or more animals (Jaenisch, R., 1988, *Science.* 240:1468–1474; Bradley, A., In: *Teratocarcinomas and Embryonic Stem Cells. A Practical Approach*, Ed.: Robertson, E. J., IRL Press, Oxford (1987), pg. 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a non-Mendelian event. However, the transgenes of the invention may be stably integrated into germline cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into non-human animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism; Leder, et al., U.S. Pat. No. 5,175,383; Kindt, et al., U.S. Pat. No. 5,183,949; Small, et al., 1986, *Cell.* 46:13–18; Hooper, et al., 1987, *Nature.* 326:292–295; Stacey, et al., 1988, *Nature.* 332:131–136; Windle, et al., 1990, *Nature.* 343:665–669; Katz, et al., 1993, *Cell.* 74:1089–1100). Transgenically introduced mutations can give rise to null ("knock-out") alleles in which a DNA sequence encoding a selectable and/or detectable marker is substituted for a genetic sequence normally endogenous to a non-human animal. Resultant transgenic non-human animals that are predisposed to a disease, or in which the transgene causes a disease, may be used to identify compositions that induce the disease and to evaluate the pathogenic potential of compositions known or suspected to induce the disease (Berns, A. J. M., U.S. Pat. No. 5,174,986), or to evaluate compositions which may be used to treat the disease or ameliorate the symptoms thereof (Scott, et al., WO 94/12627).

Offspring that have inherited the transgenes of the invention are distinguished from litter mates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the selectable marker of the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention, such as the selectable marker thereof. The presence of such nucleic acid sequences may be determined by, e.g., Southern blot analysis with DNA sequences corresponding to unique portions of the transgene, analysis of the products of PCR reactions using DNA sequences in a sample as substrates and oligonucleotides derived from the transgene's DNA sequence, etc.

XII. HSV-1 Amplicon Constructs.

In another embodiment, the present invention relates to a recombinant DNA molecule comprising an HSV-1 amplicon and at least one above-described torsin nucleic acid molecule.

Several features make HSV-1 an ideal candidate for vector development: (i) HSV-1 is essentially pantropic and can infect both dividing and non-dividing cells, such as neurons and hepatocytes; (ii) the HSV-1 genome can remain in neurons for long periods with at least some transcriptional activity; and (iii) the HSV-1 genome encodes more than 75 genes of which 38 are dispensable (nonessential) for viral replication in cell culture (Ward, P. L. and Roizinan, B., 1994, *Trends Genet.* 10:267–274). This offers the opportunity to replace large parts of the genome with foreign DNA, including one or more therapeutic genes of interest.

The technology to construct recombinant HSV-I vectors was developed more than a decade ago (Mocarski, E. S., et al., 1980, *Cell.* 22:243–255; Post, L. E. and Reizman, B., 1981, *Cell.* 25:2227–2232; Roizman, B. and F. J. Jenkins, 1985, *Science.* 229:1208–1214). With the goal to create a prototype HSV-1/HSV-2 recombinant vaccine, the HSV-1 genome was deleted in certain domains in order to eliminate some loci responsible for neurovirulence, such as the viral thymidine kinase gene, and to create space for the insertion of a DNA fragment encoding the herpes simplex virus type 2 (HSV-2) glycoproteins D, G, and I (Meignier, B., et al., 1988, *J. Inf. Dis.* 158:602–614). Currently, recombinant herpes virus vectors are being evaluated in numerous protocols primarily for gene therapy of neurodegenerative diseases and brain tumors (Breakefield, X. O., et al, In: *Cancer Gene Therapeutics*, (1995), pp. 41–56; Glorioso, J. C., et al., "Herpes simplex virus as a gene-delivery vector for the central nervous system," In: *Viral vectors: Gene therapy and neuroscience applications*, Eds.: Kaplitt, M. G. and Loewy, A. D., Academic Press, NY (1995), pp. 1–23).

The development of a second type of HSV-1 vector, the so-called HSV-1 "amplicon" vector, was based on the characterization of naturally occurring defective HSV-I genomes (Frenkel, N., et al., 1976, *J. Virol.* 20:527–531). Amplicons carry three types of genetic elements: (i) prokaryotic sequences for propagation of plasmid DNA in bacteria, including an *E. coli* origin of DNA replication and an antibiotic resistance gene; (ii) sequences from HSV-1, including an ori and a pac signal to support replication and packaging into HSV-1 particles in mammalian cells in the presence of helper virus functions; and (iii) a transcription unit with one or more genes of interest (Ho, D. Y., 1994, *Meth. Cell. Biol.* 43:191–210) defective viruses and development of the amplicon system (*Viral vectors: Gene therapy and neuroscience applications*, Eds.: Kaplitt, M. G., and Loewy, A. D., Academic Press, NY (1995), pp. 25–42).

Replication of amplicon DNA in mammalian cells is mediated by interaction of the HSV-1 origins of DNA replication ($ori_s$ or $ori_l$) with proteins provided in trans by the helper virus. These include: (i) the products of the UL5, 8 and 52 genes which form a complex that has helicase-primase activity; (ii) the UL9 gene product, which binds directly to ori; and (iii) a single stranded DNA binding protein (the product of UL29), which forms a complex with the products of UL42, a double stranded DNA binding protein, and the UL30 gene product, which is a virus encoded DNA polymerase (Ward, P. L. and Roizman, B., 1994, *Trends Genet.* 10:267–274). The $Ori_L$ sequence (144 bp) is an A-T rich palindrome which is unstable in bacteria due to its dyad symmetry (Weller, S. K., et al., 1985, *Mol. Cell Biol.* 5:930–942) and thus has not proven useful in the generation of amplicon vectors defective viruses and development of the amplicon system (*Viral vectors: Gene therapy and neuroscience applications*, Eds.: Kaplitt, M. G., and Loewy, A. D., Academic Press, NY (1995), pp. 25–42). The $ori_s$ sequence (90 bp), in contrast, with a shorter A-T rich sequence and imperfect palindrome, has proven more stable in bacteria (Stow, N. D. and McMonagle, E. C., 1983, *Virology.* 130:427–438) and is typically incorporated into amplicons. $Ori_s$ sequences from HSV-1 and HSV-2 (Kaplitt, M. G., et al, 1991, *Mol. Cell. Neurosci.* 2:320–330) have both been used, although the HSV-1 one is the most typical. HSV-1 $ori_s$ is located between the promoters for the immediate-early (IE) 3 and 4/5 genes (FIG. 2A). These promoters contain TAATGARAT sequences which respond to the vision tegument protein, VP16, as well as SP1 enhancer elements (Stem, S., 1989, *Nature.* 341:624–630), but they also increase the efficiency of DNA replication (Wong, S. W. and Schaffer, P. A., 1991, *J. Virol.* 65:2601–2611). Thus larger fragments (0.5–1 kb) bearing $ori_s$ can be used both for efficient amplicon replication in mammalian cells and to direct the expression of the transgenes from the IE3 and/or IE4/5 promoters. However, to reduce the non-specific effects of these viral regulatory elements on cell-specific or inducible promoters, several groups have used minimal $ori_s$ elements (237–295 bp) without compromising the efficient generation of amplicon vectors (Kaplitt, M. G., et al., 1991, *Mol. Cell Neurosci.* 2:320–330; Ho, D. Y., 1994, *Meth. Cell. Biol.* 43:191–210; Lu, B. and Federoff, H. J., 1995, *Hum. Gene Ther.* 6:419–428).

Replication of amplicon DNA in cells co-transduced with HSV-I helper virus proceeds by a rolling-circle mechanism creating a linear concatemer of amplicon DNA sequences. For packaging into vision capsids concatemeric genomes are cleaved between pairs of a repeat sequences after filling of the capsid, which holds about 152 kb of DNA (Deiss, L. P. and Frenkel, N., 1986, *J. Virol.* 59:605–618; Roizman, B. and Sears, A. E., "Herpes simplex viruses and their replication," In: *Virology,* 3rd. edition, Ed.: Fields, S. N., et al., Lippincott-Raven, Philadelphia, Pa. (1996), pp. 2231–2295). The pac sequences within the a repeat define the cleavage point and consist of alternating repeat and unique sequences of 250–500 bp, depending on the virus strain, in the following configuration: direct repeat (DR) 1 (20 bp)—unique sequence (U) b (65 bp)—DR2 12 bp×19–23)—DR4 (37 bp×2–3)—Uc (58 bp)—DR1 (Davison, A. J., and Wilkie, N. M., 1981, *J. Gen. Virol.* 55:315–331). The repeat nature of these sequences may contribute to their instability in bacteria, and in addition, they contain elements which can serve as recombinational hot spots in the context of the HSV-1 infection of mammalian cells (Umene, K., 1993, *J. Virol.* 67:5685–5691). Also, the promoter of the γ34.5 gene, which is located in the a repeat, can potentially influence transgene expression mediated by amplicon vectors. Current vectors contain one to two transgene cassettes (Kaplitt, M. G., et al., 1991, *Mol. Cell. Neurosci.* 2:320–330; Ho, D. Y., 1994, *Meth. Cell. Biol.* 43:191–210; Linnik, M. D., et al., 1995, *Stroke* 26:1670–1674; Lawrence, M. S., et al., 1996, *Blood Flow Metab.* 16:181–185; New, K. and Rabkin, S., 1996, *Mol. Brain Res.* 37:317–323; Pechan, P. A., et al., 1996, *Hum. Gene Ther.* 7:2003–2013), but, even within the 15 kb limit, three or more genes could be included, depending on the size of the transgenes.

A number of different promoter elements have been used to regulate transgene expression in mammalian cells, including HSV-1 IE promoters and cell-specific promoters (Smith, R. L., 1995, et al., *J. Virol.* 69:4593–4599). Since the IE promoters are induced by the tegument protein, VP 16, which is carried into the nucleus by the vision, they tend to give robust expression in the first few days after infection and then decrease dramatically as VP16 is degraded by the cells. However, IE promoters can be re-activated by superinfection with HSV-1 (Starr, P. A., et al., 1996, *Gene Ther.* 3:615–623). Other viral promoters, including hCMV IE1 and SV40 T. also direct strong but transient transgene expression in most cells (Ho, D. Y., et al., 1993, *Proc. Natl. Acad. Sci.* USA 90:3655–3659; Pechan, P. A., et al., 1996, *Hum. Gene Ther.* 7:2003–2013). Several groups have utilized cell specific promoters in the context of amplicon vectors, including those for preproenkephalin (Kaplitt, M. G., et al., 1994, *Proc. Natl. Acad. Sci.* USA 91:8979–8983), neurofilament light and heavy gene, tyrosine hydroxylase (Oh, Y. J., et al., 1996, *Mol. Brain Res.* 35:227–236; Jin, B. K., et al., 1996, *Hum. Gene Ther.* 7:215–2024; Fraefel, C., et al., 1996, 21st *International Herpesvirus Workshop*, DeKalb Ill.), neuron specific enolase, sodium channel, albumin, and α-antitrypsin. Some of these promoters appear to retain their cell specificity in the context of amplicon sequences, although levels of expression tend to be lower than with viral promoters. Moreover, the extent of specificity is difficult to assess given the altered transcriptional regulation in neural cells in culture versus in vivo and the difficulty in identifying neural cell types in vivo. Only two reports have demonstrated inducible expression mediated by amplicon vectors. Using a minimal $ori_s$ sequence (Lu, B. and Federoff, H. J. 1995, *Hum. Gene Ther.* 6:419–428) up to 50-fold dexamethasone induction of lacZ expression in primary rat hepatocytes using five copies of a tandemly repeated rat tyrosine aminotransferase (TAT) glucocorticoid responsive element GRE can be achieve (Jantzen, H. M., et al., 1987,*Cell.* 49:29–38).

Cell lines have been developed which allow the helper virus-free packaging of certain other vectors, such as retrovirus vectors (Mann, R., et al., 1983, *Cell.* 33:153–159). A similar approach for the generation of HSV-1 amplicon vectors, however, would presumably require both the expression of at least the 38 essential genes of HSV-1 (Ward, P. L. and Roizman, B., 1994, *Trends Genet.* 10:267–274; Roizman, B. and Sears, A. E., "Herpes simplex viruses and their replication," In: *Virology*, 3rd. edition, Eds.: Fields, B. N., et al., Lippincott-Raven, Philadelphia, Pa. (1996), pp. 2231–2295) and replication of the HSV-1 genome which is essential for the expression of some late genes. To circumvent these problems, a helper virus-free packaging system has been developed which utilized transient cotransfection of amplicon DNA with a set of five cosmids that overlap and represent the entire HSV-I genome but which were mutated to inactivate the pac signals (Fraefel, C. et al., 1996,*J. Virol.* 70:7190–7197; Cunningham, C. and Davison, A. J., 1993, *Virology.* 197:116–124) demonstrated that after transfection of cells, a HSV-I cosmid set could form a complete replication-competent virus genome, via homologous recombination between the overlapping sequences, and produce infectious virus particles. Deleting the pac signals, however, renders these viral genomes incapable of being packaged, while still providing all the helper-functions required for the replication and packaging of the cotransfected amplicon DNA (Fraefel, C., et al., 1996, *J. Virol.* 70:7190–7197). The resulting vector stocks are free of detectable helper virus and have titers of 106 to 107 infectious vector particles per milliliter of culture medium. Moreover, in the absence of helper virus, these vector stocks can efficiently transduce many different cell types, including neural cells and hepatocytes in culture and in vivo, while causing minimal cytopathic effects.

The basic structure of amplicon vectors has remained relatively unchanged and includes the HSV-1 $ori_s$ and pac elements responsible for replication and packaging of constructs into HSV-1 virions. New variations have evolved in response to the demand for stable and cell specific expression. These include the use of. (i) different promoters, (ii) multiple transgenes, and (iii) elements from other virus vectors.

In the central nervous system (CNS), viral promoters such as the hCMV IE1 promoter and the HSV-1 IE4/5 promoter, support strong expression of amplicon delivered transgenes (Ho, D. Y., 1993, et al., *Proc. Natl. Acad. Sci.* USA 90:3655–3659; Smith, R. L., et al., 1995, *J. Virol.* 69:4593–4599). In general, however, the time span of expression is relatively short-lived, due to poorly understood promoter inactivation. Cell type specific expression in the CNS has been attempted using several promoters, and specificity in the context of an amplicon has been reported using the neuronal preproenkephalin (PPE) promoter (Kaplitt, M. G., et al., 1994, *Proc. Natl. Acad. Sci.* USA 91:8979–8983) and the TH promoter (Jin, B. K., et al., 1996, *Hum. Gene Ther.* 7:2-15–2024). In these reports, cell specificity is due to the incorporation of large 5' regulatory sequences upstream of the minimal promoter elements of these mammalian genes. After amplicon vector delivery to the rat brain, the 2.7 kb PPE promoter and regulatory regions supported the expression of an *E. coli* lacZ marker gene for 2 months in cells morphologically resembling neurons. In transgenic mice, the 9.0 kb TH promoter/regulatory sequence efficiently directs cell and region specific expression of a lacZ marker gene (Min, N., et al., 1994, *Mol. Brain Res.* 27:281–289). The importance of this large upstream region was confirmed by comparative analysis of two amplicons with lacZ marker genes driven by either the minimal HSV-1 IE4/5 promoter or the 9.0 kb TH promoter (Jin, B. K., et al., 1996, *Hum. Gene Ther.* 7:2-15–2024). Both amplicons supported transient synthesis of β-galactosidase at the site of inoculation. However, the TH amplicon continued to express the lacZ gene at apparently similar levels and in the same number of cells for up to ten weeks post-inoculation. As confirmed by double labeling experiments, expression was anatomically restricted to neurons in the substantia nigra (SN) and locus coeruleus (LC), where endogenous catecholamines are synthesized. These reports strongly support other studies indicating that the genetic elements which contribute to cell specificity and long term expression are contained in the 5' regions upstream of the minimal promoter elements (Jin, B. K., et al., 1996, *Hum. Gene Ther.*

7:2–15–2024). The ability of HSV-1 amplicons to carry these large regulatory sequences makes this a valuable system for cell-specific gene expression in the CNS.

HSV-1 amplicons have been designed that transfer multiple transgenes using bicistronic genes or multiple expression cassettes. The picornavinis 5' ribosome binding region has been used as an internal entry site, thus linking the expression of two coding regions to a single promoter. This approach has been employed to "tag" the expression of a therapeutic gene with a marker gene. For example, amplicons overexpressing the rat brain glucose transporter (GLUT-1), linked by the internal ribosome entry site (JRES) to the E. coli lacZ gene, have been used in several experimental models (Ho, D. Y., et al., 1995, J. Neurochem. 65:842–850; Dash, R., et al., 1996, Exp. Neurol. 137:43–48). These authors demonstrated protection of neuronal death against hypoglycemia, glutamate, and 3-nitroproprionic acid. The GLUT-1/lacZ bicistronic construct allowed the authors to conclude that there was an inverse correlation between the expression of the delivered transgenes and the degree of hippocampal neuron loss in a kainate induced seizure model (Lawrence, M. S., et al., 1995, Proc. Natl. Acad. Sci. USA 92:7247–7251; Lawrence, M. S., et al, 1996, Blood Flow Metab. 16:181–185) incorporated two independent marker genes, lacZ and alkaline phosphatase (AP), both under control of human cytomegalovirus (hCMV) IE1 promoters. In a variety of cell lines and primary neurons m culture, as well as neurons in vivo, this vector supported the expression of both transgene products in about 40% of labeled cells. In the remaining labeled cells, only AP or β-galactosidase was detected at about the same rate (~30%).

The so-called "piggyback" system has been designed to improve the amplicon packaging efficiency (Pechan, P. A., et al., 1996, Hum. Gene Ther. 7:2003–2013). In traditional packaging systems, cells infected with helper virus alone generate more helper virus, and those transfected with amplicon plasmid can generate vector particles only if infected with helper virus, and consequently, they also produce helper virus. This discrepancy favors the production of helper virus and ensures that the ratios of amplicon vector to helper virus ratios remains low (usually <1). The piggyback amplicon encodes an HSV-1 gene essential for replication (IE3) which can complement a replication-incompetent helper virus deleted in IE3. In this system, packaging can be performed on any susceptible cell line as it does not need to complement the replication-defective helper virus. Packaging occurs only in cells in which both the helper virus and the amplicon are present, thus eliminating helper virus propagated independently of the amplicon. This system supports high amplicon titers of $6 \times 10^7$ transducing units per mL (t.u./mL), requires fewer passages to generate high titer vector stocks, and has apparent ratios of amplicon vector to helper virus of 3:5.

The newest generation of amplicon vectors incorporates both multiple transgenes and multiple genetic elements taken from other virus-based vectors. These "hybrid" amplicons are packaged in HSV-1 virions, and therefore retain the advantages of this virus for gene delivery to the CNS (see below), but include elements which are predicted to maintain the vector in a stable state that could support long-term gene expression in transduced cells. An amplicon vector has been constructed (Wang, S. and Vos, J., 1996, J. Virol. 70:8422–8430) that includes HSV-1 elements for replication and packaging, as well as the Epstein-Barr virus (EBV) nuclear antigen 1 (EBNA-1) gene and oriP, and the hygromycin resistance gene (HygR). EBV elements were included to support the autonomous replication of the vector genome and to maintain it as a stable episome in the host cell nucleus. After transfection of the amplicon into cells, stable colonies were isolated by hygromycin selection, and packaged vectors were generated by superinfecting these colonies with replication-incompetent helper HSV-1. Because all cells contain the hybrid amplicon, packaging was comparably efficient to the piggyback system ($4 \times 10^6$ t.u./mL), and resulted in high ratios of amplicon vector to helper virus. This vector was successfully used to infect a number of human cell lines in culture, and two human tumor lines, the hepatoma line HepG2 and the glioma line T98G in vivo. Expression of a lacZ transgene was noted for at least two weeks after delivery (Wang, S. and Vos, J., 1996, J. Virol. 70:8422–8430).

The second hybrid amplicon system incorporates the adeno-associated virus (AAV) inverted terminal repeats (ITRs), and the AAV rep gene in addition to the HSV-1 replication and packaging elements (FIG. 2B). The AAV Rep isozymes have several functions, including the recognition of the ITRs for replication of the virus genome and subsequent integration in a site-specific manner into human chromosome 19q13 (Samulski, R. J., et al., 1991, EMBO J. 10:3941–3950; Bems, K. I., "Paravoviridae: the viruses and their replication," In: Virology, 3rd edition, Eds.: Fields, S. N., et al., Lippincott-Raven, Philadelphia, Pa. (1996), pp. 2173–2197). It has been postulated that these functions would allow a transgene flanked by the ITRs to be amplified from the hybrid vector and then to remain in the transduced cell as a stable provirus, integrated in a directed manner into this non-essential locus (Johnston, K. M., et al., 1997, Hum. Gene Ther. 8:359–370). These events should be able to occur in both dividing and post-mitotic cells. These hybrid amplicons have been packaged by using both HSV-1 helper virus and helper virus-free systems. The replicative and packaging functions of the AAV ITRs in the context of the hybrid amplicon was confirmed by co-transfecting the hybrid amplicon with a plasmid that carries AAV helper functions in the presence of either adenovirus or HSV-1 helper virus. Under these conditions, an ITR-flanked marker lacZ transgene was efficiently excised from the HSV/AAV amplicon, replicated, and packaged as a recombinant AAV. The HSV/AAV amplicon vector, in comparison to a conventional HSV-1 arnplicon, supported extended transgene expression in dividing human U87 glioma cells. At fifteen days post-infection, the HSV/AAV amplicon packaged with helper virus produced about 100-fold more β-galactosidase-positive cells than conventional amplicons. Interestingly, although the helper virus-free packaged HSV/AAV amplicon vector had no demonstrable toxicity, gene expression was only 10-fold greater than with the conventional amplicon, suggesting that the helper virus may augment HSV/AAV-mediated gene expression. At fifteen days post-transduction, the hybrid amplicon-transduced cells contained significantly more lacZ transgene DNA than cells transduced with conventional amplicons, as determined by PCR analysis. The two hybrid amplicon systems discussed here are designed to extend transgene expression by adding genetic elements from other vector systems that support stable retention of the vector genome in target cells. The packaging of these hybrid amplicon vectors as defective virions ensures efficient and safe delivery of transgenes to the nucleus of host cells.

a. Amplicon Vectors for Gene Transfer into Neurons

In another embodiment, the present invention relates to the use of the above-described amplicon vectors for transfer of a torsin nucleic acid molecule into neurons.

HSV-1 has several biological properties that facilitate its use as a gene transfer vector into the CNS. These include: (i)

a large transgene capacity (theoretically up to 150 kb), (ii) tropism for the CNS in vivo, (iii) nuclear localization in dividing as well as non-dividing cells, (iv) a large host cell range in tissue culture, (v) the availability of a panel of neuroattenuated and replication incompetent mutants, and (vi) the possibility to produce relatively high virus titers.

Another important property of the HSV-1 derived vector systems for the CNS is the ability of these virions to be transported retrogradely along axons. After fusion with the cell membrane, the virus capsid and associated tegument proteins are released into the cytoplasm. These capsids associate with the dynein complex which mediates energy dependent retrograde transport to the cell nucleus along microtubules (Topp, K. S., et al, 1994, *J. Neurosci.* 14:318–325). Replication-incompetent, recombinant and amplicon HSV-1 vectors expressing the lacZ gene have been used to determine the localization and spread of vectors after injection. After single injections into many areas, including caudate nucleus, dentate gyrus and cerebellar cortex, the distribution of β-galactosidase-positive cells was determined (Chiocca, E. A., et al., 1990, *N. Biol.* 2:739–746; Fink, D. J., et al., 1992, *Hum. Gene Ther.* 3:11–19; Huang, Q., et al., 1992, *Exp. Neurol.* 115:303–316; Wood, M., et al., 1994, *Exp. Neurol.* 130:127–140). Neurons and glia were transduced at the site of injection, and activity was also detected at distant secondary brain areas, in neurons that make afferent connections with the cells in the primary injection site. The retrograde transport to secondary sites is selective to neuroanatomic pathways, suggesting trans-synaptic travel of the virus capsids. Retrograde transport of an amplicon vector has been demonstrated after striatal injections in both the substantia nigra pars compacta and the locus coeruleus (Jin, B. K., et al., 1996, *Hum. Gene Ther.* 7:2015–2024). The ability of HSV-1 to travel by retrograde transport to neurons in afferent pathways suggests that the delivery of genes by these vectors can be spread beyond the original injection site to other regions of neuroanatomic importance.

The original report of amplicon-mediated gene delivery to neurons used primary cells in culture (Geller, A. I. and Breakefield, X. O. 1988, *Science* 241:1667–1669). Amplicon vectors have been used to study neuronal physiology, for example effects of expression of GAP43 or the low affinity nerve growth factor (NGF) receptor on morphology and growth of neuronal cells (Neve, R. L., et al., 1991, *Mol. Neurobiol.* 5:131–141; Battleman, D., et al., 1993, *J. Neurosci.* 13:941–951). Amplicons can direct rapid and stable transgene expression in hippocampal slice cultures (Bahr, B., et al., 1994, *Mol. Brain Res.* 26:277–285), and this has been used to model both kainate receptor-mediated toxicity (Bergold, P. J., et al., 1993, *Proc. Natl Acad. Sci.* USA 90:6165–6169) and glucose transporter-mediated protection of neurons (Ho, D. Y., et al., 1995, *J. Neurochem.* 65:842–850). In vivo, amplicons have been used to deliver a number of candidate therapeutic genes in different models of CNS diseases. For example, expression of the glucose transporter protects neurons in an induced seizure model ((Ho, D. Y., et al., 1995, *J. Neurochem.* 65:842–850; Lawrence, M. S., et al., 1995, *Proc. Natl. Acad. Sci.* USA 92:7247–7251; Lawrence, M. S., et al., 1996, *Blood Flow Metab.* 16:181–185), bcl-2 rescues neurons from focal ischemia (Linnik, M. D., et al., 1995, *Stroke* 26:1670–1674), and expression of TH mediates behavioral changes in parkinsonian rats (During, M. J., et al., 1994, *Science* 266:1399–1403). Thus, amplicons have proven effective for functional expression of many transgenes in the CNS.

Amplicons have recently been used to generate mouse somatic mosaics, in which the expression of a host gene is activated in a spatial and developmentally regulated fashion. Transgenic mice were engineered with a germline transmitted NGF gene that contained an inactivating insertional element between the promoter and transcript flanked by the loxP sites. The somatic delivery of cre recombinase by an amplicon vector successfully activated the expression of NGF in these animals (Brooks, A. I., et al., 1997, *Nat. Biotech.* 15:57–62). The ability to express genes in specific cells at various points in development will have broad applications, especially for genes for which germline deletion ("knockouts") are conditional lethal mutants.

Traditionally, the stability of transgene expression after transduction, and the cytopathic effect of the helper virus were the limiting features of amplicon mediated gene delivery into cells of the CNS. Recent advancements have largely addressed these constraints. Several promoter elements, such as preproenkephalin and tyrosine hydroxylase, can drive long-term transgene expression from amplicon vectors when upstream regulatory sequences are included (Kaplitt, M. G., et al., 1994, *Proc. Natl. Acad. Sci.* USA 91:8979–8983; Jin, B. K., et al., 1996, *Hum. Gene Ther.* 7:2015–2024). The development of hybrid amplicons containing non-HSV genetic elements that can potentially integrate in a site directed manner (Johnston, K. M., et al., 1997, *Hum. Gene Ther.* 8:359–370), or form stable replicating episomes (Wang, S. and Vos, J., 1996, *J. Virol.* 70:8422–8430), should maintain the-introduced transgene in a emetically stable configuration. Finally, the development of a packaging system devoid of contaminating helper virus (Fraefel, C., et al., 1996, *J. Virol.* 70:7190–7197) has significantly reduced the cytopathic effects of amplicon vectors in culture and in vivo. The easily manipulated plasmid-based amplicon, and the helper virus-free packaging system allows the construction of a virtually synthetic vector which retains the biological advantages of HSV-1, but reduces the risks associated with virus-based gene therapy.

b. Amplicon Vectors for Gene Transfer into Hepatocytes

In another embodiment, the present invention relates to the use of the above-described amplicon vectors for transfer of a torsin nucleic acid molecule into hepatocytes. As discussed in the previous section, HSV-I amplicon vectors have been extensively evaluated for gene transfer into cells of the nervous system. However, amplicon vectors can also be an efficient means of gene delivery to other tissues, such as the liver.

Certain hereditary liver disorders can be treated by enzyme/protein replacement or by liver transplantation. However, protein infusion can only temporarily restore the deficiency and is not effective for many intracellular proteins. Liver transplantation is limited by donor organ availability and the need for imnmunosuppression for the lifetime of the patient. Thus, gene transfer to the liver is highly desirable, and consequently, various virus vector systems, including adenovirus vectors (Stratford-Perricaudet, L. D., et al., 1990, *Hum. Gene Ther.* 1:241–256; Jaffe, A. H., et al., 1992, *Nat. Genet.* 1:372–378; Li, Q., et al., 1993, *Hum. Gene Ther.* 4:403–409; Herz, J. and Gerard, R. D., 1993, *Proc. Natl. Acad. Sci.* USA 90:2812–2816), retrovirus vectors (Hafenrichter, D. G., et al., 1994, *Blood* 84:3394–3404), baculovirus vectors (Boyce, F. M. and Bucher, N. R. L., 1996, *Proc. Natl. Acad. Sci.* USA 93:2348–2352; Sandig, V., et al., 1996, *Hum. Gene Ther.* 7:1937–1945) and vectors based on HSV-I (Miyanohara, A., et al., 1992, *New Biologist* 4:238–246; Lu, B., et al., 1995, *Hepatology* 21:752–759; Fong, Y., et al., 1995, *Hepatology* 22:723–729; Tung, C., et al., 1996, *Hum. Gene Ther.* 7:2217–2224) have been evaluated for gene transfer into hepatocytes in culture and in experimental animals. Recombinant HSV-1 vectors have been used to express hepatitis B virus surface antigen (HBsAG), *E. coli* β-galactosidase, and canine factor IX-CFM in infected mouse liver (Miyanohara, A., et al., 1992, *New Biologist* 4:238–246). Virus stocks were either injected directly into the liver parenchyma or applied via the portal vein. By either route, gene transfer proved to be highly efficient and resulted in high levels of HB SAG or CFIX in the circulation, and in a large number of β-galactosidase-positive hepatocytes. Although detectable gene expression was transient, a significant number of vector genomes was demonstrated to persist for up to two months after gene transfer. The efficiency of long term gene expression could be increased somewhat by replacing the HCMV IE1 promoter with the HSV-1 LAT promoter to direct the expression of the transgene.

In two different ex vivo studies, primary mouse or human hepatocytes were successfully transduced with HSV-1 amplicon vectors which express *E. coli* β-galactosidase or human growth hormone, respectively. After reimplantation of the transduced primary mouse hepatocytes into mouse liver, β-galactosidase-positive cells could be demonstrated for up to two weeks (Lu, B., et al., 1995, *Hepatology*. 21:752–759).

Both recombinant HSV-1 and amplicon vectors can be used for cancer therapy. With the goal to enhance the immunogenicity of hepatoma cells and consequently their elimination by host defense systems (Tung, C., et al., 1996, *Hum. Gene Ther.* 7:2217–2224) constructed an amplicon vector that expresses the human interleukin-2 gene (HSV-IL-2). Mouse hepatoma cells (HEPA 1–6) were transduced with either HSV-IL-2 or a control amplicon vector that expressed *E. coli* β-galactosidase (HSVlac), irradiated, and then used to immunize mice. Animals pre-treated in this way were subsequently challenged with intraportal injection of $10^6$ viable tumor cells. In the control group (HSVlac), seven out of ten animals developed liver, tumors, whereas in the group of the ten animals pre-treated with HSV-IL-2 transduced hepatoma cells, only one animal developed a tumor and that had a much smaller size as compared to those in the control group. Similar amplicon vectors can be used in the present invention.

XIII. DYT1, Related Genes and Methods of Detecting a Mutation or Polymorphism which Mediates Dystonia Disorders.

As discussed above, many cases of early onset torsion dystonia are caused by a three-base-pair deletion (GAG) in the coding region of the TOR1A gene (alias DYT1, DQ2), resulting in loss of a glutamic acid in the carboxy terminal of the encoded protein, torsinA. TOR1A and its homolog TOR1B (alias DQ1, also referred to herein as TORB) are located adjacent to each other on human chromosome 9q34. Both genes comprise five similar exons; each gene spans a 10 kb region. While the following example exemplifies the invention by describing how the methods disclosed herein can be utilized to screen for a mutation which mediates a movement disorder, it is to be understood that the invention is not limited to identifying mutations, which mediate a particular clinical disorder or disease, or polymorphisms which increase an individual's risk of developing a particular disease or disorder. The invention provides a general method which can be utilized to detect mutations or polymorphisms in any neuronal gene putatively associated with a particular phenotype. For example, utilizing the sequence information provided herein one of skill in the art can confirm the role of a torsin or a torsin-related gene in other neuronal disease. Involvement of a torsin or torsin-related gene can be implied from a neuroanatomical correlation of gene expression (e.g., peripheral nervous system or central nervous system specific, or more specifically by a particular type of neuron such as dompaminergic neurons in the substantia nigra) and clinical symptoms which indicate the involvement of a particular neuronal gene or its encoded product.

For example, mutational analysis of most of the coding region and splice junctions of TOR1A and TOR1B do not reveal additional mutations in typical early onset cases lacking the GAG deletion (N=17), in dystonic individuals with apparent homozygosity in the 9q34 chromosomal region (N=5), or in a representative Ashkenazi Jewish individual with late onset dystonia, who shared a common haplotype in the 9q34 region with other late onset individuals in this ethnic group.

A database search revealed a family of nine related genes (50–70% similarity) and their orthologs in species including human, mouse, rat, pig, zebrafish, fruitfly, and nematode. At least four of these occur in the human genome. Proteins encoded by this gene family share functional domains with the AAA/HSP/Clp-ATPase superfamily of chaperone-like proteins, but appear to represent a distinct evolutionary branch.

Over 12 different gene loci have been implicated in various forms of primary, hereditary dystonia (Mueller, U., et al., 1998, *Neurogenetics* 1:165–177.). As discussed above, the TOR1A (DYT1) locus on human chromosome 9q34 is responsible for the most severe form of hereditary dystonia—early onset, generalized torsion dystonia (Ozelius, L., et al., 1989, *Neuron*. 2:1427–1434; Kramer, P., et al, 1994, *Am. J. Hum. Gen.* 55:468–475). In this form, symptoms usually begin in a limb at a mean age of 12.5 yrs, with progression, in most cases, to involve multiple body parts over a subsequent 5 yr period (Bressman, S. B., et al., 1994, *Ann. Neurol.* 36:771–777). Inheritance follows an autosomal dominant mode of transmission with reduced penetrance (30–40%; Risch, N. J., et al., 1990, *Am. J. Hum. Genet.* 46:533–538). The TOR1A gene on human chromosome 9q34 (Ozelius, L., et al., 1989, *Neuron.* 2:1427–1434) was recently identified and determined to encode a novel protein, torsinA (Ozelius, L. J., et al., 1997, *Genome Res.* 7:483–494). A single mutation, a three base pair (GAG) deletion, in the heterozygous state accounts for 50–60% of non-Jewish (NJ) individuals and over 90% of Ashkenazi Jewish (AJ) individuals with this form of dystonia (Bressman, S. B., et al., 1994, *Ann. Neurol.* 36:771–777). The predominance of this mutation can reflect both a unique phenotype produced by the altered protein, with loss of one of a pair of glutamic acids in the carboxy terminal region, and an increased frequency of this mutation, due to genetic instability in an imperfect tandem 24 base pair repeat in the region of the deletion (Klein, C., et al., 1998, *Human Mol. Genet.* 7:1133–1136).

The TOR1A gene is expressed selectively in specific regions of the human brain, with highest levels in the dopaminergic neurons of the substantia nigra (Augood, S. J., et al., 1998, *Ann. Neurol.* 43:669–673.). The involvement of these neurons in the etiology of dystonia is consistent with other genetic, pharmacologic and clinical studies. Metabolic deficiency states which compromise dopamine synthesis can also manifest with severe childhood-onset dystonia, including mutations in genes for GTP-cyclohydrolase I (Ichinose, H., et al., 1994, *Nature Genetics.* 8:236–242.) and tyrosine hydroxylase (Ludecke, B., et al., 1995, *Hum. Genet.* 95:123–125; Knappskog, P. M., et al., 1995, *Hum. Mol. Genet.* 4:1209–1212; Wevers, R. A., et al., 1999, *J. Inherit.*

*Metab. Dis.* 22:364–373.) underlying dopa-responsive dystonia, and for L-aromatic amino acid decarboxylase (Hyland, K., et al., 1998, In: *Fifth International Congress of Parkinson's Disease Movement Disorders.* New York, N.Y.) and dihydropteridine reductase (Blau, N., et al., 1998, *J. Inherit. Metab Dis.* 21:433–434.) in other neurologic syndromes with marked dystonic features. Dystonic symptoms can also be elicited by D2 receptor blockers (LeWitt, P. A., 1995, "Dystonia caused by drugs" In: *Handbook of Dystonia.* Eds.: King, J., Tsui, C. and Calne, D. B., pp. 227–240, Marcel Dekker, Inc., New York, N.Y.); and a missense mutation in the D2 receptor has been implicated in a family with myoclonus dystonia (Klein, C., et al., 1999, *Proc. Natl Acad. Sci.* USA 27:5173–5176.).

The TOR1A gene encoding torsinA is a member of a larger gene family, including an adjacent gene, TOR1B (DQ1) which encodes a highly homologous (70%) protein, torsinB. The human genome contains at least two other related genes, TOR2A and TOR3A (TORP1 and TORP2; Ozelius, L. J., et al., 1997, *Genome Res.* 7:483–494). All four human genes are expressed in most fetal and adult tissues. The interest in the TOR1A gene family derives not only from its role in a neurologic disease, but also from the similarity of the deduced protein, torsinA, to a superfamily of proteins with a variety of chaperone-like functions. The similarity includes an ATP-binding domain, eleven conserved motifs and predicted secondary structure (Neuwald, A. F., 1999, *Structure* 7:R19-R23; Ozelius, L. J., et al., 1997, *Genome Res.* 7:483–494; Lupas, A., et al., 1997 *Trends Biochem. Sci.* 22:399–404), shared with the heat shock protein (HSP)/Clp ATPase and the "ATPase Associated with a variety of cellular Activities" (AAA) superfamily (Parsell, D. A. and Lindquist, S., 1993, *Ann. Rev. Genet.* 27:437–496; Gottesman, S., et al., 1997, *Genes Dev.* 11:815–823; Confalonieri, F. and Duguet, M., 1995, *Bioessays* 17:639–650). This AAA+family includes the N-ethylmaleimide-sensitive fusion (NSF) protein, which has been implicated in vesicle fusion and neurotransmitter release (Hanson, P. I., et al., 1997, *Curr. Opin. Neurobiol.* 7:310–315; Haas, A. 1998, *Trends Cell Biol.* 0:471–473.) and HSP104, which has been shown to determine the state of prion aggregation (DeBurman, S. K., et al., 1997, *Proc. Natl. Acad. Sci.* USA 94:13938–13943).

Thus, another embodiment of the invention, is the exon structure and physical map of the human TOR1A and TOR1B genes and the use of intron primers to detect other mutations in other neuronal genes that are implicated as mediating a particular phenotype which gives rise to clinical symptoms that correlate with the neuroanatomical expression of the gene. For example, the methods described herein can be used to investigate the role of TOR1A or TOR1B in other neuronal diseases, including but not limited to the neurodegenerative disease, for example Parkinson's disease.

More specifically, test samples obtained from patients afflicted with a neuronal disease, for example, Parkinson's disease patient samples can be screened for mutations in genomic DNA, as well as RNA by RT-PCR analysis in lymphoblast lines. To assess the relative contribution of the two alleles to the mRNA expression in cells from patients, we will carry out parallel analysis in genomic DNA and lymphoblast RNA (RT-PCR) using polymorphic variations and/or mutations in the coding region to mark alleles.

One of skill in the art could easily modify the methods described herein to screen other neuronal genes for mutations using intronic and flanking primers (e.g., SEQ ID NOS: 30–47) to amplify and scan or sequence genomic DNA isolated from patients afflicted with different clinical manifestations of a related disease or disorder suspected of having a common genetic basis. For example, sample can be isolated from three types of dystonia patients: those with early onset, generalized dystonia who lack the GAG-deletion; those who appear to be homozygous in this 9q34 chromosomal region; and a representative AJ individual with late onset dystonia, who shared a common haplotype of polymorphic alleles in this region with other late onset AJ individuals, suggesting a founder mutation. Using the primers (e.g., intronic and flanking primer sequences) and methods described herein the TOR1A and TOR1B genes present in the test samples can be analyzed for mutations by amplifying and screening genomic DNA. Further it is anticipated that one of skill in the art could use the cDNA nucleotide sequence information provided herein, for example the sequences embodies by SEQ ID NOS: 48–63, to design and/or isolate other nucleic acid molecules suitable for use as probes and primers. In general, a suitable primer will comprise at least about 15 (e.g., 15, 17, 19, 20, 21) to 50 consecutive nucleotides of a nucleic acid sequence from the group consisting of SEQ ID NOS: 48–63. An isolated nucleic acid molecule or its complement can be used in combination with each other, or with a primer selected from the group consisting of SEQ ID NOS: 30–39 (DYT1-specific primers) or SEQ ID NOS: 40–47 (TORB-specific primers).

The intron primers of the invention provide particularly useful tools for detecting the presence or absence of different types of neuronal disease in which a torsin or torsin-related gene has been implicated. In one embodiment of the invention, the primers and methods of the invention are used to detect dopamine-mediated diseases. In an alternative embodiment the primers and methods presented herein can be utilized to evaluate the role of TOR1A or TORB in a movement disorder (e.g., dystonia) or a neurodegenerative disease (e.g., Parkinson's disease). The term "dopamine-mediated disease" as used herein refers to a disease of a neuron that releases or responds to the neurotransmitter dopamine or any compound (e.g., small organic molecule, drug) that resembles dopamine in chemical structure or biological response (e.g., resulting in an action potential in a post-synaptic neuron).

Although the invention described herein is exemplified using the primers and methods disclosed herein to detect dopamine-mediated disease it is to understood that the invention encompasses the use of the disclosed primers and methods to investigate the involvement of torsin and torsin-related genes in other neuronal diseases.

Thus, it is envisioned that any intron primers of the TOR1A gene or any of its family members, such as torsin, can be used in the methods of the invention.

In summary, Applicants demonstrate herein that the DYT1 gene which is responsible for early onset torsion dystonia encodes a protein (torsinA) which is a member of a new family of human proteins with significant homology in their functional domains to the heat shock protein (HSP) 100/Clp ATPase family of chaperonins (Ozelius, L. J., et al., 1997, *Nature Genetics* 17:40–48). Further, DYT1 is expressed in the human brain at high levels in the dopamine neurons of the substantia nigra (Augood, S. J., et al., 1998, *Ann. Neurol.* 43:669–673). Thus, torsinA and related proteins may play pivotal roles in the pathogenesis of other neurodegenerative diseases, for example, Parkinson's disease, by facilitating correct folding or degradation of mutant (α-synuclein and other proteins found in Lewy bodies, thereby protecting dopaminergic neurons from damaging chemical and physical stresses. The importance of protein processing/trafficking in neurologic diseases has only recently begun to be appreciated (Brooks, A. I., et al., 1997, *Nat. Biotech.* 15:57–62; Welch, W. J. and Gambetti, P., 1998, *Nature* 392:23–24) subsequent to findings that proteins in these processing pathways can regulate accumulation of toxic, aggregated proteins, for example, amyloidogenic processing of Alzheimer's β-amyloid precursor protein, and involvement of ubiquitin proteolytic signaling domains in an hereditary form of early onset parkinsonism and in a disorder of neuronal development, Angelman syndrome. Considered together these observations suggest that modifier genes, or physical events, can determine disease status in individuals bearing specific mutations in one of two alleles for either disease gene (e.g., GAG deletion in early onset dystonia). Thus, it is likely that disruptive mutations in one or both alleles of the DYT1 and/or RDP genes could lead to greater compromise of protein function and a more severe condition, such as Parkinson disease.

XIV. Methods of Identifying Genes Comprising a Polymorphism that Confers Susceptibility to Neuronal Diseases or a Mutation that Mediates Neuronal Disease.

Many families appear to have a genetic predisposition for Parkinson's disease, and, in some, the disease follows a clear-cut pattern of autosomal inheritance. One of the genes responsible for hereditary autosomal dominant, late onset Parkinson's disease on chromosome 4q21–23 encodes variant forms of (α-synuclein; another causing autosomal recessive early onset Parkinsonism on chromosome 6q25.2–27, bears deletions in a novel protein, parkin, which has ubiquitin domains suggesting chaperone and proteolytic functions; and a third, as yet unidentified, gene involved in autosomal dominant, late onset Parkinson's disease has been located to chromosome 2p13 Gasser, T., et al.,1998, *Nat. Genet.* 18:262–265). Still, many familial cases of Parkinson's disease do not map to these loci, and there are undoubtedly additional major loci and modifier genes which underlie the occurrence, severity and age of onset of this disease.

As stated above, Applicants teach herein that the DYT1 gene is responsible for most cases of early onset dystonia (Ozelius, L. J., et al., 1997, *Nature Genetics* 17:40–48). The corresponding transcript is expressed at high levels in dopaminergic neurons of the substantia nigra in human brain, as well as in the CA1 region of the hippocampus and granule layer of the cerebellum (Augood, S. J., et al., 1998, *Ann. Neurol.* 43:669–673). Several lines of evidence suggest that this and other dystonia genes may also have a role in some familial forms of parkinsonism. Clinically early onset dystonia and Parkinson's disease can be considered a continuum in which compromise of the function of dopaminergic neurons in the substantia nigra during childhood leads to dystonic symptoms which persist into adulthood, and extensive death of these neurons in adulthood manifests as Parkinson's disease.

This association between dystonia and parkinsonism suggests that some dystonia genes, for example the DYT1 and RDP genes, may be involved in Parkinson's disease and vice versa. Early onset dystonia is inherited as an autosomal dominant disorder with 30–40% penetrance, such that most (60–70%) carriers of the defective gene are not actually affected (Risch, N. J., et al., 1990, *Am. J Hum. Genet.* 46:533–538). The mean age of onset is nine years beginning with twisting, contracted positioning of an arm or leg and progressing to involvement of other limbs and the torso, with no remittance and no effective therapy (Bressman, S. B., et al., 1994, *Ann. Neurol* 36:771–777). There is a developmental window of susceptibility, such that if a gene carrier passes the age of 28 years without onset of symptoms, he/she will usually remain disease-free for life. Examination of the brains of early onset dystonia patients after death reveals no apparent neuronal degeneration, but from secondary cases, the syndrome is believed to arise from dysfunction of neurons in the basal ganglia and striatum (Hedreen, J. C., et al.,1988, *Adv. Neurol.* 50:123–132). Almost all cases of early onset dystonia are caused by a three base pair deletion (GAG) in the coding region of a novel protein, termed torsinA, resulting in loss of a glutamic acid residue in the carboxy terminal region of the protein (Ozelius, L. J., et al., 1997, *Nature Genetics* 17:40–48). Thus, the predisposition to early onset dystonia is caused by a small change in the structure of only some of the torsinA molecules in a cell, with other normal torsinA molecules being present, presumably due to a dominant-negative effect of the mutant protein, a new function of the mutant protein, or haploinsufficiency of the normal protein. The RDP syndrome in some ways bridges early onset dystonia and Parkinson's disease by sharing features of each. Like both these diseases, RDP (rapid onset dystonia with parkinsonism) is inherited as an autosomal dominant condition with reduced penetrance (40–75%), onset of symptoms correlates with stressful events, e.g. child birth, marathon running, and meningitis, and is associated with apparent reduction in dopaminergic neurotransmission. Simultaneous onset of both dystonic and parkinsonian symptoms occurs in an age interval (14–45 yrs.) between that of onset of early onset dystonia and (usually between 5–20 yrs.) and typical Parkinson's disease (usually >52 yrs.)

In addition, several forms of hereditary dystonia, including dopa-responsive dystonia (DRD) and X-linked dystonia-parkinsonism (lubag) have predominantly dystonic symptoms in childhood followed by parkinsonian symptoms in adulthood; while rapid onset dystonia with parkinsonism (RDP), with an intermediate age of onset, presents with both dystonic and parkinson features. Further it is well known that drugs which partially block dopamine receptors, such as neuroleptics, can lead to tardive dystonia in a substantial fraction of patients (LeWitt, P. A., 1995, "Dystonia caused by drugs" In: *Handbook of Dystonia*. Eds.: King, J., Tsui, C., and Calne, D. B., pp. 227–240, Marcel Dekker, Inc., New York, N.Y.) Other indications which are consistent with a role for dystonia genes include the observations that early onset Parkinson patients frequently manifest dystonic postures early in the course of the disease, followed later by typical Parkinsonian features; and in some Parkinson patients dystonic symptoms appear when levels of administered L-dopa are low.

Effects of dopaminergic drugs also implicate a relationship between the molecular etiology of dystonia and Parkinson's disease. Drugs which partially block dopamine receptors, such as neuroleptics used to treat psychiatric illness, can lead to tardive dystonia in 5–10% of patients (LeWitt, P. A., 1995, "Dystonia caused by drugs" In: *Handbook of Dystonia* Eds.: King, J., Tsui, C., and Calne, D. B., pp. 227–240, Marcel Dekker, Inc., New York, N.Y.) This form of secondary dystonia is thought to result from blockade and supersensitivity of dopamine receptors in the striatum, resulting from sustained inhibition of dopaminergic neurotransmission. Interestingly, patients who develop tardive dystonia before the age of 30 years have an increased tendency to progress to generalized dystonia, whereas those affected in later life tend to have focal dystonias (LeWitt, P. A., 1995, "Dystonia caused by drugs" In: *Handbook of Dystonia* Eds.: King, J., Tsui, C., and Calne, D. B., pp. 227–240, Marcel Dekker, Inc., New York, N.Y.) Dystonic symptoms can be ameliorated in some patients with dopamine agonists, e.g., L-dopa or apomorphine, or drugs which stimulate synaptic release of dopamine, e.g., tetrabenazine which under chronic use acts as a dopamine depleter. Dystonic movements have also been noted in Parkinson patients under two circumstances. In cases of early onset Parkinson's disease, patients frequently manifest dystonic posturing early in the course of the disease with later onset of typical parkinsonian symptoms. Further, detailed symptomatic evaluation of Parkinson patients during L-dopa treatment has revealed that in a small percentage of patients, dystonic symptoms appear early in the course of treatment, when blood levels of L-dopa are still low, resolve when levels are elevated (i.e., at the same time parkinsonian symptoms improve), and then reoccur as L-dopa levels drop. These individuals (termed D-I-D for Dystonia—Improvement of Parkinson's—Dystonia) tended to be relatively young and have been hypothesized to represent a genetic subgroup. In a recent article on MPTP inducing dystonia and parkinsonism demonstrated transient dystonia preceding hemiparkinsonism, correlated with decreased striatal dopamine in baboons treated with MPTP.

While not wishing to be bound by theory, it appears that insufficient release of dopamine in the human striatum during childhood can cause predominantly dystonic symptoms, which can persist into adulthood and if the insufficiency progresses the resulting loss of dopaminergic innervation can result in the onset of parkinsonian symptoms. Clinical observations which are consistent with this theory include the fact that several forms of hereditary dystonia: X-linked dystonia-parkinsonism (lubag), dopa-responsive dystonia (DRD), and rapid onset dystonia with parkinsonism (RDP), manifest parkinsonian symptoms in latter life. Further, lubag a disease which is endemic to the Philippines, shows predominantly dystonic features in childhood and progresses to frank parkinsonism with extensive degeneration of dopaminergic neurons in the substantia nigra in adulthood. Dopa-responsive dystonia (DRD) looks clinically similar to early onset dystonia during childhood, and also has no apparent neuropathology (Ozelius, L. J. and Breakefield, X. O., 1994, *Nature Genetics* 8:207–209). In contrast to typical early onset dystonia, DRD can be virtually cured at any age by administration of L-dopa. Dopa-responsive dystonia has been found to be caused by a deficiency in synthesis of dopamine, due either to an autosomal dominantly inherited haploinsufficiency of GTP cyclohydrolase I (needed for synthesis of biopterin, the co-factor for tyrosine hydroxylase; (Ichinose, H., et al., 1994, *Nature Genetics* 8:236–242.) or to an autosomal recessive loss of tyrosine hydroxylase (Ludecke, B., et al., 1995, *Hum Genet.* 95:123–125; Knappskog, P. M., et al., 1995, *Hum. Mol. Genet.* 4:1209–1212). A dominantly inherited rapid onset form of dystonia, RDP, manifests with both dystonic and parkinsonian features in mid-life, but with no apparent neuronal degeneration. CSF levels of the dopamine metabolite, homovanillic acid (HVA) are abnormally low in RDP patients, as well as in some asymptomatic obligate carriers, suggesting decreased dopaminergic transmission. Early onset dystonia and RDP share several interesting features; they are both inherited as autosomal dominant conditions with reduced penetrance (about 40% of gene carriers manifest symptoms; Bressman, S. B., et al., 1989, *Ann. Neurol.* 26:612–620); and onset of symptoms is frequently associated with stress, including infectious disease, injury or strong physical exertion.

As shown herein torsinA is a heat-shock/chaperone protein. Studies in a number of neurodegenerative diseases indicate that such proteins may be critical in preventing accumulation of toxic protein aggregates in cells. The finding that torsinA is highly expressed in the dopaminergic neurons suggests that these neurons may be especially dependent on it for protein trafficking and/or protection from stress (Augood, S. J., et al., 1998, *Ann. Neurol.* 43:669–673). By analogy, although there are many tumor suppresser proteins, they are differentially expressed in various cell types, such that loss of function of the ubiquitously expressed retinoblastoma protein preferentially causes retinoblastoma tumors. Thus developmentally immature retinoblasts appear to rely essentially exclusively on this tumor suppressor protein for control of cell growth. The mutation in torsinA responsible for early onset dystonia is a very discrete one with 80% of cases having a predicted loss of a single glutamic acid residue only in half the cellular torsinA proteins. Still, expression of this mutant protein creates a metastable condition such that another insult, either genetic or environmental, during (and only during) early life can precipitate a permanent dystonic state (without apparent neurodegeneration) in 30% of carriers. Because of its role as a protective protein, it is feasible that a polymorphism could confer increased risk (e.g., a genetic predisposition or increased susceptibility) to the development of a neuronal disease and that a mutation can mediate pathologic consequences, for example damage and/or death of dopaminergic neurons in concert with other genetic and environmental factors.

Thus, another embodiment of the instant invention provides a method of detecting the presence or absence of a polymorphism or mutation in a neuronal gene (e.g., TOR1A, TOR1B, TORP1 or TORP2) in a mammal. More specifically, it is envisioned that the nucleotide sequence information disclosed herein would enable one of skill in the art to isolate probes and primers which can be used in the methods taught herein to predict an individual's susceptibility to a neuronal disease or to identify particular mutations associated with a phenotype that is consistent with a particular neuronal disease.

In summary, based on the clinical and neuroanatomical correlations between dystonia and Parkinson's disease, and on the predicted protective function of torsinA and related family members, it is reasonable to believe that: 1) different mutations in the same genes (e.g., intron sequences) can underlie both dystonia and Parkinson's disease; 2) torsinA and homologous proteins, torsinB and the torps, may serve to protect neurons from stress conditions and/or facilitate correct folding of proteins, such as α-synuclein; and 3) loss of torsinA will compromise function of dopaminergic neurons, thereby altering synaptic communication in the striatum.

The following Examples are offered for the purpose of illustrating the present invention and are not to be construed to limit the scope of this invention. The teachings of all references cited herein are hereby incorporated by reference.

EXAMPLE 1

Chromosomal DNA

Clinical Criteria and Patient Samples

Individuals and families were ascertained from a database of patients diagnosed and treated by members of the Movement Disorders Group at Columbia Presbyterian Medical Center and the Movement Disorders Division at Mount Sinai Medical Center (New York), and through advertisements in the newsletters of the Dystonia Medical Research Foundation. The criteria for the diagnosis of primary torsion dystonia and the method of evaluation were the same as described previously (Bressman, S. B., et al., 1994, *Ann. Neurol.* 36:771–777). All subjects gave informed consent prior to their participation in the study.

Two groups of individuals with primary dystonia were considered. The first group consisted of known DYT1 gene carriers from four non-Jewish families previously linked to chromosome 9q34 (Kramer, P., et al., 1994, *Am. J. Hum. Gen.* 55:468–475). These four families were chosen from the seven previously described families based on individual family lod scores of >+2 at 9q34 markers. Included in this group were also Ashkenazi individuals who carried the founder haplotype of 9q34 alleles (Bressman, S. B., et al., 1994, *Ann. Neurol.* 36:771–777). The second group of individuals had primary dystonia but their linkage status was unknown, i.e., non-Jewish and non-Ashkenazi Jewish individuals from small families and Ashkenazi Jewish individuals who did not have the founder haplotype. This latter group was further subdivided into three clinical subgroups, based on previous studies delineating the DYT1 phenotype (Bressman, S. B., et al., 1994, *Ann. Neurol.* 36:771–777; Bressman, S. B., et al., 1994, *Neurology.* 44:283–287; Kramer, P., et al., 1994, *Am. J. Hum. Gen.* 55:468–475). These subgroups are: 1) typical or likely DYT1 phenotype: i.e., early (<28 years) limb-onset with spread of dystonia to at least one other limb, but not to cranial muscles; 2) atypical or unlikely DYT1 phenotype; i.e., focal or segmental cervical-cranial dystonia of any age at onset, or writer's cramp beginning after age 44 years; 3) uncertain DYT1 phenotype; i.e., dystonia not fitting into either of these other categories, such as writer's cramp beginning before age 45, cervical or cranial-onset dystonia spreading down to limbs, or limb-onset spreading up to cranial muscles. Patients with symptoms typical of early onset dystonia were also categorized as uncertain if they had confounding neurological abnormalities.

The four uncertain cases that carried the GAG-deletion are described below. One had a clinical phenotype typical for DYT1, but was classified as uncertain because she had polio as a child, possibly confounding the classification. Another carrier was also typical of DYT1 but was classified as uncertain because of concurrent head tremor and a family history of head and arm tremor. The remaining two carriers had features of typical early onset dystonia; one had early limb onset which spread to other limbs, but also to cranial muscles, and the other had onset in an arm spreading to the neck.

In families of unknown linkage status with multiple affected members a single classification was assigned to all affecteds within the family. If families had members with both uncertain and typical phenotypes, a classification of typical was assigned; if families had members with both uncertain and atypical phenotypes, a classification of atypical was assigned; if families had members with both atypical and typical phenotypes, a classification of uncertain was assigned.

Individuals with a wide range of ethnic and geographic ancestry were also sought to be included. This study was approved by the review boards of both institutions.

DNA Isolation, Lymphoblast Lines and Southern Blots

Venous blood samples were obtained from participating individuals. DNA was extracted from whole blood (Gusella, J., et al., 1979, *Proc. Natl. Acad. Sci.* USA 76:5239–5242) or from lymphoblast lines established from blood lymphocytes by EBV transformation (Anderson, M. and Gusella, J., 1984, *In Vitro.* 29:856–858). CEPH pedigree DNA was obtained from CEPH (Centre d'Etude du Polymorphisms Humain, Paris, France). For Southern blots genomic DNA was digested with PstI, HindIII and EcoRI (NEB) according to the manufacturer's instructions. Digested DNA was resolved on 1% agarose gels at 70V for 16 h. Southern blotting was performed using standard techniques and the filters were hybridized to cDNAs (see below).

Isolation of RNA, Northern Blots, RT-PCR

Cytoplasmic RNA was isolated from lymphoblasts and fibroblasts established from patients and controls (Sambrook, J., Fritsch, E. F., and Maniatis, T., 1989, In: *Molecular Cloning A Laboratory Manual*, Cold Spring Harbor Laboratory Press, Cold Spring Harbor). Total RNA was extracted from human adult and fetal tissue obtained at autopsy using the guanidinium thiocyanate method (Chirgwin, J. M., et al., 1979, *Biochem.* 18:5294–5300). Tissues were obtained from both control and DYT1 carrier individuals and included brain cortex, cerebellum, hippocampus, lung, liver, muscle, placenta, spleen, thyroid, intestines, and eye. A Northern blot was prepared from this RNA following standard procedures (Sambrook, J., Fritsch, E. F., and Maniatis, T., 1989, In: *Molecular Cloning A Laboratory Manual*, Cold Spring Harbor Laboratory Press, Cold Spring Harbor). In addition, Northern blot filters containing 2 $\mu$g of poly (A+) RNA from 8 different adult human tissues and four different fetal human tissues were used (Clontech). First strand cDNA synthesis was performed on lymphoblast RNA samples with oligo-dT and random primers using Superscript II reverse transcriptase (Gibco; Newman, P. J., et al., 1988, *J. Clin. Invest.* 22:739–743). The reactions were carried out at 42° C. for 90 minutes followed by gene specific PCR amplification to generate the various cDNAs in the critical DYT1 region from patients and controls.

Cosmid Contig

Cosmids were isolated from two human chromosome 9-specific libraries: the Lawrence Liver-more library, which was constructed in Lawrist 16 using DNA from a chromosome 9-only somatic cell hybrid (van Dilla, M. A. and Deaven, L. L., 1990, *Cytometry* 11:208–218); and the Los Alamos library, which was constructed in sCos (Stratagene) from flow-sorted metaphase human chromosomes (Deaven, L. L., et al, 1986, *Symp. Quant. Biol.* 51:159–167). Cosmid colony grid filters were stamped and prepared for hybridization as described (McConnick, M. K., et al., 1993, *Genomics.* 18:553–558; Murrell, J., et al., 1995, *Genomics.* 25:59–65). Filters were screened with gel-purified YAC DNA from a 400 kb critical region and over 800 positive colonies were picked, gridded and stamped for hybridization. A cosmid walk was initiated from both ends of the critical region starting with the end clone of cosmid LL09NC0150H11 and several D9S63 positive cosmids (18D5LA, 37H5LA). End sequences of hybridizing cosmids were used to generate PCR primers to continue the walk by re-screening grids. The resulting set of about 60 cosmids was digested with EcoRI and fragments were resolved by agarose gel electrophoresis to distinguish similar and novel regions. An overlapping subset of 11 cosmids was then aligned by digestion with EcoRI, XhoI and NotI in a series of single and double digests. Fragments were resolved by electrophoresis in 1% agarose gels, transferred to Southern blots and hybridized to cosmid ends, exons and unique sequence in the region, generated by PCR or with synthetic 20 bp oligonucleotides.

Hybridization

Probes (gel-purified YAC DNA, cosmid ends, exon clones, PCR products and cDNAs) were labeled by random priming (Feinberg, A. P. and Vogelstein, B., 1984, *Anal Biochem.* 137:266–267) using $\alpha$-$^{32}$P-dATP (3000 Ci/mmol;

NEN). Oligonucleotides were end-labeled with T4 polynucleotide kinase (NEB) using α-$^{32}$P-dATP (6000 Ci/mmol; NEN). Probes were preannealed with CotI DNA, human placenta DNA and vector DNA, as necessary to saturate repeat sequences.

Hybridizations were performed in Church-Gilbert buffer at 55° C. overnight Northern filters were hybridized in 5×SSPE, 50% formamide, 5× Denhard's solution, 0.5% SDS and 300 μg/mL salmon sperm DNA overnight at 42° C. Filters were washed and exposed to autoradiographic film as described (Murrell, J., et al., 1995, *Genomics.* 25:59–65).

Exon Amplification, cDNA Library Screening and Extension

Exon amplification was performed on cosmids spanning the region using vectors pSPL1 (Buckler, A. J., et al., 1991, *Proc. Natl. Acad. Sci.* USA 88:4005–4009) and pSPL3-IV. RT-PCR products were digested with BstX1 to eliminate vector-only products (Church, D. M. et al., 1994, *Nat. Genet.* 6:98–105). Cloned exon fragments were used to screen human fetal and adult cDNA libraries by colony hybridization (Sambrook, J., Fritsch, E. F., and Maniatis, T., 1989, In: *Molecular Cloning. A Laboratory Manual*, Cold Spring Harbor Laboratory Press, Cold Spring Harbor). Libraries were prepared in ZAP by Stratagene and included adult human striatum, hippocampus, substantia nigra, caudate putamen, brainstem, heart, spleen and liver, and fetal human brain and retina. The sequences generated from these cDNA clones were aligned and edited using the Sequencher program (Gene Codes). cDNA contigs were extended in two ways—by re-screening libraries with PCR fragments generated from the ends of the contig; and by using 5' and 3' RACE and THON PCR systems (Frolunan, M. A., et al., 1988, *Proc. Natl. Acad. Sci.* USA 85:8998–9002; Apte, A. N. and Siebert, P. D. 1993, *Biotechniques* 15:890–893) as modified by Clontech.

Sequencing

Dideoxy sequencing was performed using the Sequitherm Long Read Cycle Sequencing Kit (Epicenter Technologies) either with infrared labeled vector primers for the LICOR sequencing machine or with specific primers labeled with α-$^{33}$P-dATP (2000 Ci/mmol, NEN) for standard sequencing. Direct sequencing of PCR products was done using an enzymatic cleanup process with exonuclease I and shrimp alkaline phosphatase (USB) for 15 minutes at 37° C. and 15 minutes at 85° C., followed by sequencing with Sequenase (USB). The LICOR sequence was read using the BaselmagIR software package (LICOR) which includes data collection and image analysis software. The α-$^{33}$P-dATP gels were transferred to 3 MM Whatman, dried and exposed to autoradiographic film overnight and then read and entered manually into the GCG programs (Wisconsin Package Version 9.0, Genetics Computer Group, Madison, Wis.).

SSCP Analysis

DNA sequences were screened for mutations by PCR of 100–300 bp fragments followed by SSCP analysis, using first strand cDNAs synthesized from patient and control lymphoblast RNA and genomic DNA. PCR reactions were performed as described (Ozelius, L., et al., 1992, *Am. J. Hum. Genet.* 50:619–628). SSCP analysis of the PCR amplification products was carried out as described (Orita, M., et al., 1989, *Genomics.* 5:874–879; Hayashi, K. and Yandell, D. W. 1993, *Hum. Mutation.* 2:338–346). All fragments with altered migration were sequenced directly and evaluated in families to check inheritance, and in controls to determine whether they represented normal polymorphisms. When single base pair changes altered restriction sites, restriction digestion of PCR products was used to replace SSCP analysis. In these cases, standard PCR was performed in a 25 μl final volume without radioactivity. The PCR products were digested according to manufacturer's instructions (NEB) and visualized by staining with ethidium bromide after electrophoresis in 2–3.5% agarose gels. and adult liver; DQ2 from adult substantia nigra, hippocampus and frontal cortex; DQ3 from adult frontal cortex; DQ4 from adult frontal cortex and fetal brain; and DQ5 from adult occipital cortex, substantia nigra and frontal cortex. All but three of the 28 unique putative exons were accounted for by these cDNAs. Hybridization of these three to Northern blots from a number of adult human tissues (Clontech) revealed no corresponding message species. Further screening of cDNA libraries with these putative exons did not yield positive clones. Therefore these three may be the result of cryptic splice junctions or may represent low abundance messages.

The five cDNAs were extended in both directions by 5' and 3' RACE (Frohman, M. A., et al., 1988, *Proc. Natl. Acad. Sci.* USA 85:8998–9002) and sequenced in multiple clones. Transcripts were then aligned across the cosmid contig by hybridizing Southern blots of restriction digested cosmid DNA with 5' and 3' cDNA ends, exon clones and oligonucleotides corresponding to cDNA sequence. Estimated genomic regions covered by these genes are: 8 kb for DQ1; 13 kb for DQ2; 10 kb for DQ3; 52 kb for DQ4 and >40 kb for DQ5. Since only the 3' untranslated region of cDNA DQ5 overlapped the critical interval, this gene was excluded from this study. Given the extensive exon trapping carried out in this region, and the fact that 2–10 exons were identified for each cDNA, it is possible that these transcripts account for all the genes in the critical region. However, several large regions (>10 kb each), one centromeric to DQ1 and two within the first two introns of DQ4, could contain other genes, particularly genes with one or no introns that would be missed by exon amplification.

EXAMPLE 2

Cosmid Contig and Transcript Map

A cosmid contig was constructed across the 150 kb target region on chromosome 9q34 between polymorphic markers, D9S2161 and D9S63 to facilitate identification of genes. Gridded arrays of cosmids from two chromosome 9-specific libraries were screened initially with four YACs: 8HI2, 183D9, 251H9 and 22A4, spanning this region. A positive subset of cosmids was screened sequentially with end sequences from cosmids, starting on the centromeric side with the end of cosmid LL09NCO150H11, which hybridized to YAC 8H12, and, at the telomeric end, with D9S63-positive cosmids, 37F5LA and 18D5LA, which hybridized to the other three YACs. New overlapping cosmids were compared by restriction digestion and gel electrophoresis, and end sequences were obtained from novel fragments and used to rescreen secondary cosmid grids. A cosmid contig with over 3-fold redundancy was generated across the genomic region between LL09NC0150H11 and 37F5LA. A restriction map was constructed using a representative subset of 11 overlapping cosmids by determining fragment sizes following gel electrophoresis of single and double digests using the restriction enzymes, EcoRI, XhoI and NotI. Fragments were aligned by size and hybridization patterns using markers D9S2161 and D9S63, cosmid end clones, cloned exons, and oligonucleotides from unique regions (FIG. 1). The estimated length of the contig between the defining markers is 150 kb.

Genes in this region were identified by exon amplification, which allows cloning of exons by virtue of flanking splice sites in genomic DNA during cellular processing of RNA expressed by splicing vectors (Buckler, A. J., et al., 1991, *Proc. Natl. Acad. Sci.* USA 88:4005–4009; Church, D. M., et al., 1994, *Nat. Genet.* 6:98–105). A subset of cosmids from the critical region were digested with PstI or Sacd, or with both BamHI and BglII, and cloned into these vectors. Of over 60 putative exons trapped, 28 produced independent sequences. These exon clones were then used to screen human cDNA libraries from different human adult and fetal tissues, which had been generated by priming with oligo dT or random primers. Five cDNAs were represented in multiple overlapping clones: DQ1 from fetal brain, adult frontal cortex

EXAMPLE 3

Sequence of cDNAs

DQ1 (encoding a torsinB sequence, SEQ ID NO: 4) and DQ2 (encoding a torsinA sequence, SEQ ID NO: 2) are highly homologous transcripts with 72% identity at the nucleotide level and 69% amino acid identity in the predicted protein sequence. The genes are in opposite orientations with their 3' ends <12 kb apart in the genome. The longest transcript for DQ2 consists of 2,072 bp with a predicated open reading frame of 998 bp from nucleotide 43 to 1041 of (SEQ ID NO: 5). A composite nucleotide sequence of the torsinA gene comprised of genomic and cDNA sequence is set forth in SEQ ID NO: 1. A composite nucleotide sequence of the torsinA gene comprised of cDNA sequence is set forth in SEQ ID NO: 5.

The sequence around the putative ATG translation start site contains the critical −3 purine residue, but none of the other features of the Kozak consensus sequence (Kozak, M., 1987, *Nucleic Acids Res.* 15:8125–8148). There is an in-frame termination codon in overlapping genomic sequence from cosmid 23GILA starting 365 bp upstream of the 5' end of this cDNA. The 3' untranslated portion is 1031 bp long and contains two poly $A^+$ addition sites, one, ATTTAAA, at nucleotide 1390 and the other, AATAAA, at nucleotide 2054, with poly A tails present about 20 bp down from each of them in several of the cDNA clones.

The cloned DQ2 cDNA appears to be essentially full length based on the sizes of corresponding transcripts. Clone H4, ATCC Accession No. 98454 contains nucleotides 99 to 1377 as set forth in SEQ ID NO: 5. Northern blots of adult and fetal human RNA showed two ubiquitous messages of about 1.8 kb and 2.2 kb which hybridized to a probe from the coding portion of the cDNA. Only the 2.2 kb message hybridized to sequences 3' to the first poly $A^+$ addition site, indicating that the larger species may represent utilization of the second poly $A^+$ addition site. In fetal brain, lung and kidney, as well as adult brain, heart and pancreas, another message species of about 5 kb was present in low abundance. The 1.8 kb and 2.2 kb messages, and no novel species, were seen in autopsy tissues from AJ individuals bearing the founder mutation, including adult, lymphoblasts, fibroblasts and cerebellum, as well as fetal brain, muscle, spleen, intestines, eye, lung and liver. The open reading frame of transcript DQ2 predicts a 6.81 pI polypeptide of 332 amino acids with a calculated molecular weight of 37,813 D, which is termed torsinA (SEQ ID NO: 2).

cDNA DQI is 2504 bp with an open reading frame of 802 bp (SEQ ID NOS: 6 and 7) and was deposited at the ATCC as Accession No. 98455. Based on the strong similarities between cDNAs DQI and DQ2, and between genomic sequence 5' to cDNA DQ1 in cosmid 54A5LA and the 5' coding end of cDNA DQ2, the methionine start site for the DQ1 message is probably not in the existing DQ1 clone. The nucleotide sequence set forth in SEQ ID NO: 3 and the corresponding amino acid sequence set forth in SEQ ID NO: 4 were generated from a combination of genomic and cDNA sequence. The 3' untranslated portion is 1702 bp long with a poly $A^+$ addition site, AATAAA, at position 2483 and a poly A tail about 20 bps downstream (SEQ ID NO: 7). Northern blot analysis revealed a ubiquitously expressed message of about 2.8 kb, present at low levels in adult brain, but not detectable in fetal brain. The open reading frame of the existing clone encodes 290 amino acids, suggesting that the corresponding protein, which we have named torsinB, has a molecular weight >32,000 D (SEQ ID NO: 4).

EXAMPLE 4

Mutational Analysis

Two possible mechanisms of mutation were considered in this dominant disorder: disruptive mutations, which would inactivate the protein and result in haploinsufficiency of the encoded protein; and missense mutations, which would cause a "gain-of-function" or "dominant negative" effect of the mutant form of the protein that would override the function of the normal protein or interfere with other proteins.

Gross alterations in sequence were excluded by Southern blot analysis using genomic DNA from 30 dystonia patients from different ethnic backgrounds hybridized to the four cDNAs. Transcripts from the critical region were then screened for sequence variations using lymphoblast RNA from 14 individuals affected with torsion dystonia from different families representing 12 unique haplotypes in an extended region surrounding the DYT1 gene (D9S62a to ASS) and two control individuals, one AJ and one non-Jewish. Of these 12 unique haplotypes, four were from families that demonstrated clear chromosome 9 linkage. Theses included four non-Jewish families (Kramer, P., et al, 1994, *Am. J. Hum. Gen.* 55:468–475), two of which were French-Canadian and shared a common haplotype and the AJ founder mutation. The four distinct disease-linked haplotypes in these six families were initially assumed to represent independent mutations in DYT1. After initial RT-PCR with primers in the 3' and 5' end of the transcripts, nested PCR was carried out in overlapping fragments of 150–300 bp. Fragments were resolved by SSCP analysis and all variant bands were sequenced in both directions. All transcripts showed a number of variations in both coding and noncoding regions. Most of these were "silent," involving single base pair substitutions in the 5' and 3' untranslated regions or in the third position of triplet codons, such that the encoded amino acid would not be altered. Only three of these changes affected the amino acid sequence: 1) valine isoleucine in DQ4; 2) aspartic acid histidine in DQ2; and 3) deletion of a glutamic acid in DQ2. All sequence variations in the coding regions were analyzed in genomic DNA after determining the exon/intron structure in cosmid DNA. All of these nucleotide changes, except one—the GAG-deletion in DQ2 (SEQ ID NO: 5 at nucleotide positions 946–948), were confirmed as polymorphisms by their presence in control samples. Surprisingly, the GAG-deletion in DQ2 was present in all six individuals representing the four confirmed DYT1-linked haplotypes.

To pursue this finding, the co-segregation of the GAG-deletion with carrier status in all known chromosome 9-linked families was examined, as well as in a large number of AJ and non-Jewish controls. This GAG-deletion was analyzed using PCR products generated from genomic DNA samples in three ways: SSCP, direct sequencing, or digestion with BseRI, which cuts 10 bp downstream of the normal GAGGAG sequence, but does not cut the 5 GAG-deletion sequence. The association of the GAG-deletion with carrier status in the chromosome 9-linked families was complete. All 261 affected and unaffected obligate gene carriers in 68 chromosome 9-linked families were heterozygous for this deletion (including 64 AJ families carrying the founder haplotype and 4 non-Jewish families). Strikingly, the deletion was not present in 260 AJ and 274 non-Jewish control chromosomes, and was never observed in the homozygous state in any individual.

To further assess the role of this deletion in primary dystonia, an additional 155 individuals with varying clinical manifestations from families which were too small for linkage analysis were typed. The association with the typical manifestation of early onset torsion dystonia was very strong in these families. Among 41 cases of typical early onset dystonia from 19 different families, all affected individuals in 14 of the families carried the GAG-deletion, while affected individuals from five other families did not. Affecteds from two of these five families are suspected to have dopa-responsive dystonia, which closely mimics the phenotype of DYT2, but were unconfirmed. Some typical cases that do not carry the GAG-deletion may have other, as yet unidentified, mutations in DQ2, or mutations in other genes; for example, features of the DYT1 phenotype occur in some individuals who carry a mutation on chromosome 8. Among 38 cases (from 11 AJ, 27 non-Jewish families), for which the diagnosis of early onset dystonia was uncertain, four carried the GAG-deletion (1 AJ, 3 non-Jewish) while the remaining 34 did not (for clinical description of these four uncertain carriers see Methods.). Among the 76 individuals classified as atypical, that is not having features typical of early onset dystonia (36 AJ, 2 Sephardic Jewish [SJ] and 38 non-Jewish families), none carried the GAG-deletion. Collectively, these observations provide compelling evidence that the GAG-deletion is responsible for the vast majority of cases of typical early onset dystonia. These include individuals of AJ descent, in whom the founder mutation causes >95% of cases (Risch, N., et al., 1995, *Nature Genetics* 9:152–159), as well as most non-Jewish cases of varied ethnic backgrounds.

The identification of a single mutation (GAG-deletion) on affected chromosomes responsible for almost all cases of typical early onset dystonia is remarkable. Two possible explanations may account for this surprising finding: 1) all these cases may be ancestrally related, representing a unique founder mutation which predates the introduction of this mutation into the AJ population; or 2) the same mutation has arisen independently, and is the only change (or perhaps one of a few) that can result in the early onset dystonia phenotype. To distinguish between these possibilities, three polymorphic sequence variations (A, B, and C) were identified in a 5 kb region surrounding the GAG-deletion and used these to perform a more detailed allelic analysis. In affected individuals carrying the four confirmed DYT1-linked haplotypes, two different patterns of alleles were observed, 1, 1, 2 on three of the disease-bearing chromosomes (families 5, 9, and 16) and 1, 2, 1 on one of the disease-bearing chromosome (family 1). This finding clearly supports the idea that the same mutation (GAG-deletion) has arisen more than once. Sixty AJ and 60 non-Jewish control individuals were also typed with these markers and the frequencies determined for the different allele patterns. Among the controls, only three patterns were observed at loci A, B, C: 1, 1, 2 (AJ controls=68%; non-Jewish controls=55%); 1, 2, 1 (AJ=20%; non-Jewish=34%); and 2, 1, 2 (AJ=12%; non-Jewish 11%), suggesting that these polymorphisms are in strong linkage disequilibrium with each other. The high frequency of the 1, 1, 2 pattern in GAG-deleted chromosomes in 9-linked families is consistent with the high incidence of this pattern in controls and is not in conflict with independent mutations. When the other 18 GAG-deleted chromosomes in patients with unknown linkage status were typed for A, B and C alleles- 15 carried 1, 1, 2 (families 2–4, 6–8, 10–15, and 17–22), one had the 1, 2, 1 pattern (family 2) and two others (families 3, 4) were unphaseable but likely have the 1, 2, 1 pattern. These observations support the conclusion of at least two independent mutations but the high frequency of the 1, 1, 2 pattern in the normal population might mask our ability to distinguish additional independent events.

To examine whether the individuals bearing identical allelic patterns at markers A, B, and C showed additional evidence of common ancestry, their haplotypes were investigated at flanking microsatellite markers (D9SI59, D9S2160, D9S2161, D9S63 and D9S2162). This analysis revealed that the four individuals carrying the uncommon (1, 2, 1) pattern at A, B, C are likely to share a common ancestry (families 1–4). All of these families come from the same region of North Carolina and Virginia, have British ancestry, and affected individuals share alleles across ≧200 kb surrounding the GAG-deletion. Examination of the remaining 18 chromosomes, all of which carry the same (1, 1, 2) haplotype, also reveals some interesting commonalities that fall into two categories. First, three families share a portion of the alleles characteristic of the AJ founder mutation. The SJ individual (family 6) carries a haplotype at four loci which is identical to the Ashkenazi founder haplotype (family 5). A natural question is whether the disease chromosome in this Sephardic individual was introduced recently through an unidentified Ashkenazi ancestor, or alternatively whether this progenitor mutation existed in the Jewish population prior to the separation of the Sephardim from the Ashkenazim approximately 1,000 years ago. The affected individual in family 7, reported to be non-Jewish of mixed English and Austria-Hungarian ancestry, was consistent with carrying the founder AJ chromosome across the whole 500 kb haplotype region. It is likely that this individual has inherited the DYT1 gene from a recent Ashkenazi ancestor. A third, possibly related chromosome was found in an Italian family (family 8). This individual shared the AJ founder alleles ≧90 kb centromeric to the GAG-deletion. This raises the intriguing possibility of a Mediterranean origin for this mutation predating its introduction into the Ashkenazi Jewish population. Alternatively, as before, the chromosome could be of more recent Ashkenazi ancestry. Second, three common haplotypes are found in other families, distinct from the AJ founder haplotype: 1) family 9 (German origin) shared the haplotype across ≧420 kb with family 10 (Irish origin), and apparently with family 11 (Ashkenazi Jewish; although was unphased). The long stretch of DNA shared by these individuals suggests a common origin, despite the varied ethnicity. 2) Two of the French-Canadian families (12 and 13) also bear a shared haplotype over a smaller region, ≧130 kb. Thus, there may be shared ancestry here as well, but in the more distant past. 3) Another two families, 14 (German origin) and 15 (Irish origin) shared the same haplotype across ≧320 kb. Among the remaining families, there appears to be an additional seven haplotypes. In total, there appears to be at least 12 distinct classes of haplotypes, suggesting that the same mutation has occurred at least that many times, however, it remains possible that all of the chromosomes with the 1,1,2 pattern are ancestrally related in the very distant past.

TABLE 4

Genotype of GAG deletion in candidate cDNA in affected individuals and controls

| Categories | Families | Genotype in Individuals | | |
|---|---|---|---|---|
| | | +/+[a] | +/− | −/− |
| Controls: | | | | |
| AJ | 130 | 130 | 0 | 0 |
| NJ | 137 | 137 | 0 | 0 |
| Affected and obligate carriers[b] in 9-linked families: | | | | |
| AJ founder haplotype | 64 | 0 | 173 | 0 |
| NJ | 4 | 0 | 88 | 0 |
| Affecteds of unknown linkage[c]: | | | | |
| AJ: typical[d] | 1 | 0 | 4 | 0 |
| uncertain | 11 | 10 | 1 | 0 |
| atypical | 36 | 36 | 0 | 0 |
| SJ: typical | 1 | 0 | 2 | W0 |
| atypical | 2 | 2 | 0 | 0 |
| NJ: typical | 17 | 5 | 30[e] | 0 |
| uncertain | 27 | 24 | 3 | 0 |
| atypical | 38 | 38 | 0 | 0 |

[a]+: GAGGAG, −: GAG(del)
[b]lod score > +2 for 9q34 markers (Kramer et al., Am. J. Hum. Gen. 55:468–475 (1994)
[c]families too small for linkage analysis
[d]see clinical criteria in methods for definitions
[e]from 12 families autosomal dominant pattern of inheritance with reduced penetrance (30–40%). Six genes causing non-degenerative forms of dystonia have been mapped on human chromosomes: dopa-responsive—dominant on 14q21–22 (Nygaard, T., et al., 1993, *Nature Genetics* 5:386–391; Endo, K., et al., In: *Monographs in Neural Sciences Age-related dopamine-dependent disorders*, Eds.: Segawa, M and Nomura, Y., Karger Publishers, New York (1995), pp. 120–125) and recessive on 11p11.5 (Ludecke, B., et al., 1995, *Hum. Genet.* 95:123–125; Knappskog, P. M., et al., 1995, *Hum. Mol. Genet.* 4:1209–1212); paroxysmal on 2q (Fink, J. K., et al., 1996, *Am. J. Hum. Genet.* 59:140–145; Fouad, G. T., et al., 1996, *Am. J Hum. Genet.* 59:13 5–139); a late onset, focal on 18p (Leube, B., et al., 1996, *Hum. Mol. Genetics* 5:1673–1678); a mixed phenotype on 8; and, the DYT1 gene on chromosome 9q34 (Ozelius, L., et al., 1989, *Neuron.* 2:1427–1434). Two of these other dystonia genes have been identified and both implicate decreased dopaminergic transmission in dystonia. Dopa-responsive dystonia can be caused by disruption of tyrosine hydroxylase, the rate limiting enzyme in dopa synthesis (Ludecke, B., et al., 1995, *Hum. Genet.* 95:123–125; Knappskog, P. M., et al., 1995, *Hum. Mol. Genet.* 4:1209–1212) and by haploinsufficiency of GTP cyclohydrolase 1, needed for synthesis of the tyrosine hydroxylase cofactor, biopterin (Furukawa, Y., et al., 1996, *Adv. Neurol.* 69:327–337). The only genetic rodent models reported to date—the dystonic (dt) mt (LeDoux, M. S., et al., 1995, *Brain Res.* 697:91–103), the mouse mutant, dystonia musculorum (dMd) (Brown, A., et al., 1995, *Nat. Genet.* 10:301–306); and hamsters with paroxysmal dystonia (dt52) (Nobrega, J. N., et al., 1995, *Neurosci.* 64:229–239; Nobrega, J. N., et al., 1996, *Neurosci.* 71:927–937) do not match the genetic or neurobiologic features of human dystonias.

Although there is no distinctive neuropathology in primary dystonia (Hedreen, J. C., et al., 1988, *Adv. Neurol.* 50:123–132; Zeman, W., et al., 1967, *Psychiatr. Neurol. Neurochir.* 10:77–121), this condition is believed to result from imbalance of neural transmission in the basal ganglia, since cases of secondary dystonia reveal lesions in the caudate nucleus, putamen, and globus pallidus, as well as the thalamus and rostral brain (Dooling, E. C., et al., 1975. *Brain.* 98:29–48; Bhatia, K. P., et al., 1994, *Brain.*

Discussion

Positional cloning was used to identify a strong candidate for the DYT1 gene on human chromosome 9q34 which is responsible for the early onset form of p dystonia. Mutational analysis revealed a 3-bp deletion in the coding on of a transcript which was the only non-polymorphic change identified on disease-bearing chromosomes. This mutation was uniquely associated with typical cases of early onset dystonia and appears to have arisen independently on different haplotypes in a number of ethnic groups. Thus, apparently only one, or one of a few variations in the encoded protein can give rise to this particular phenotype. The deletion results in loss of one of a pair of glutamic acid residues near the carboxy terminus of a novel protein, termed torsinA. These glutamic acids and flanking cysteine residues are conserved in an adjacent, homologous human gene, encoding a protein termed torsinB, and in related mouse and rat sequences. TorsinA and B define a new family of ATP-binding proteins with a distant relationship to the HSP100/Clp family of proteins (Schirmer, E. C., et al., 1996, *TIBS.* 21:289–296).

Insights into the protein relationships and possible function of torsinA were revealed by searches of GenBank protein databases. A closely related deduced protein sequence is encoded by cosmids from *Caenorhabditis elegans*, here termed, torsin-related protein *C. elegans* (torpCel). ESTs were also identified corresponding to human, mouse and rat torsinA and torsinB, as well as to two other related proteins, torp1 and torp2. FIG. 4A shows an amino acid alignment of these predicted proteins. The glutamic acid pair, bearing the deletion in affected individuals, is conserved in all human, rat and mouse torsinA and torsinB transcripts, suggesting it is part of a functional domain. Although the glutamic acid pair is absent in the torps, the neighboring residues are fairly well conserved, including the cysteine residues which flank this region. A phylogeny analysis suggests that torsinA and torsinB are most closely related to each other (~70% amino acid sequence identity), and that they and the torps are equally distant (~50% identity). A more distant similarity to known proteins offers some insight into potential function: the middle ~200 amino acids of the torsins and torps are similar to a conserved domain in the HSP 100/Clp family of proteins (Schirmer, E. C., et al., 1996, *TIBS.* 21:289–296; Perier, F., et al., 1995, *Gene.* 152:157–163). Members of the HSP100/Clp family have chaperone functions or proteolytic activity, which can confer thermotolerance, allow correct folding of proteins and regulate protein signaling (Parsell, D. A., et al., 1993, *Annu. Rev. Genet.* 27:437–496). HSP100/ Clp proteins are distinguished by two features: they bind ATP and/or have ATPase activity; and they occur in oligomeric complexes with one or more additional protein species. FIG. 4C compares the torsin family to two representative members of the HSP100 protein family: HSP101, a heat shock protein from soybeans in the HSP100 Subfamily 1B; and SKD3, a ubiquitous mouse protein in the Subfamily 2M (Perier, F., et al., 1995, *Gene.* 152:157–163; Schirmer, E. C., et al., 1996, *TIBS.* 21:289–296). The most robust feature is a conserved ATP/GTP-binding sequence comprising two motifs: the nucleotide-binding site "A" (GxTGxGKT/S;

SEQ ID NO: 65) followed ~60 amino acids later by the Mg$^{++}$-binding site "B" (ShhhFDEhEKxH; SEQ ID NO: 66), where x indicates variable residues and h indicates hydrophobic residues (Walker, J. E., et al., 1982, *EMBO J.* 1:945–950; Confalonieri, F. and Duguet, M., 1995, *Bioessays.* 17:639–650). In a conserved stretch of 140 amino acids that include the nucleotide binding domain, torsin family members are 25–30% identical to HSP100 family proteins. Key residues of the HSP100 consensus site IV (Schirmer, E. C., et al., 1996, *TIBS.* 21:289–296) and another site (SN; FIG. 4C) are also conserved, but consensus site V is absent in the torsins. Interestingly, a mutation in the carboxy region of the *E. coli* HSIV/ClpY in this family blocks binding to its companion protein (Missiakas, D., et al., 1996, *EMBO J.* 15:6899–6909). The discrete lutamic acid deletion in the carboxy end of torsinA would be consistent with the ability of the mutant protein to interfere with binding and activity of other subunits. It is tempting to consider torsinA in the same superfamily as the heat shock/proteolytic proteins, as it would be consistent with a dominant-negative effect mediated by disruption of a multimeric complex.

Figure 4B:
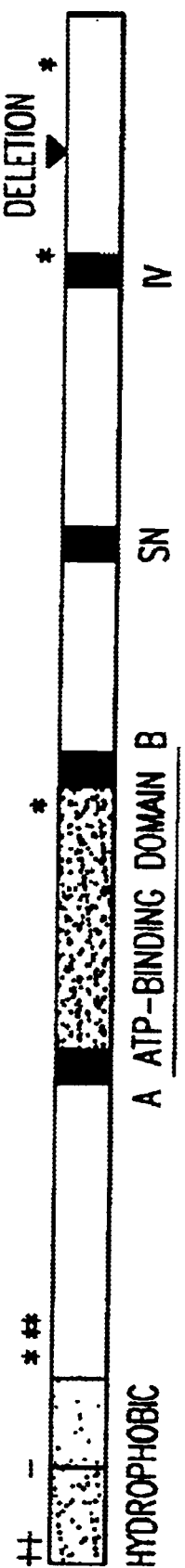
Figure 4C:
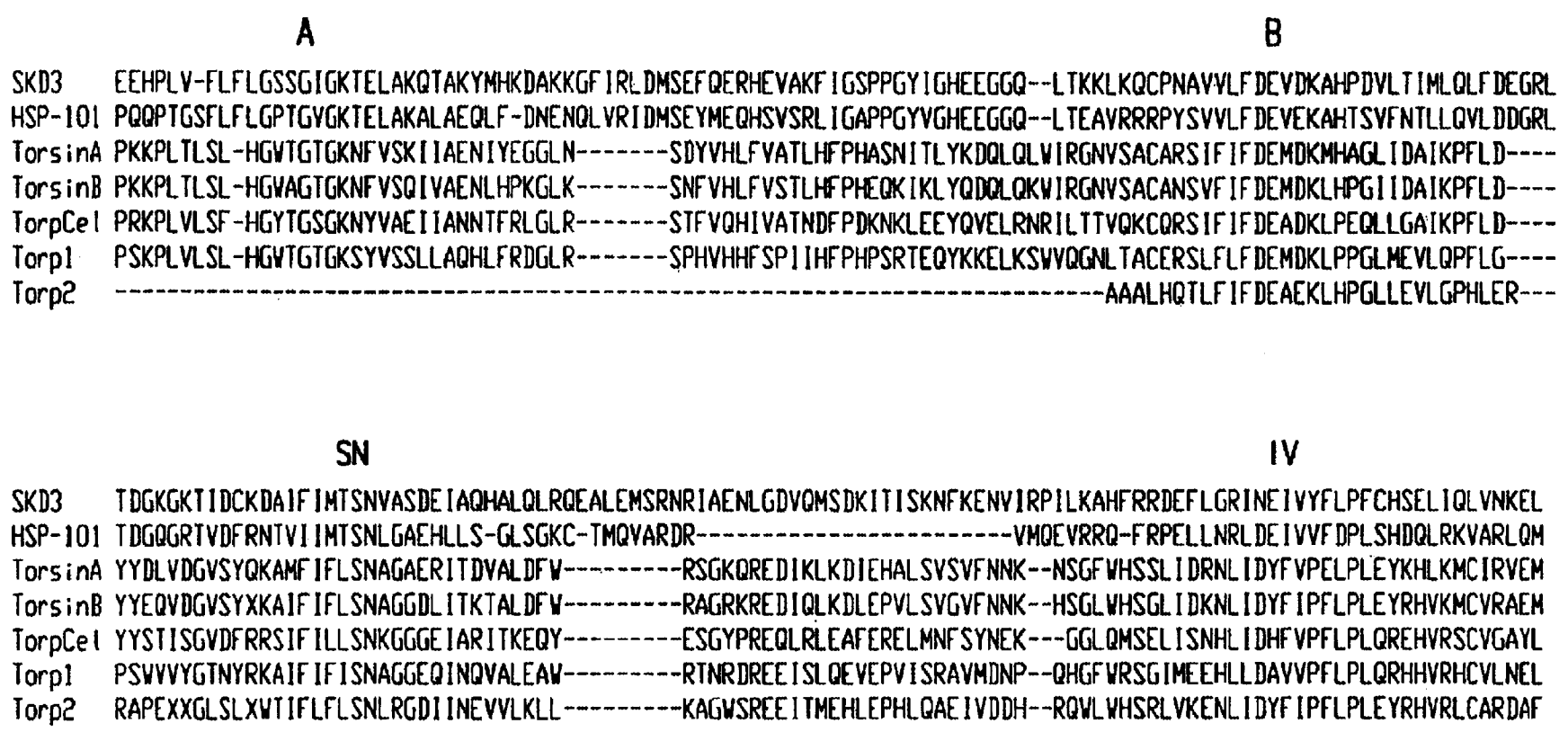
Figure 5B:
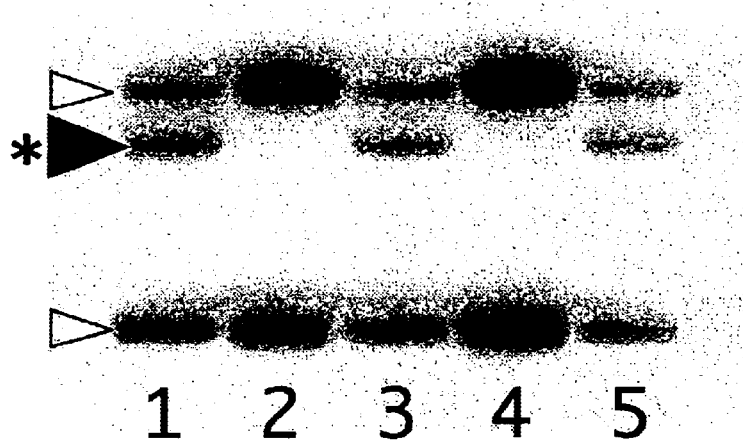
FIGS. 5A–5D. Resolution of GAG-deletion associated with early onset dystonia.
Figure 5C:
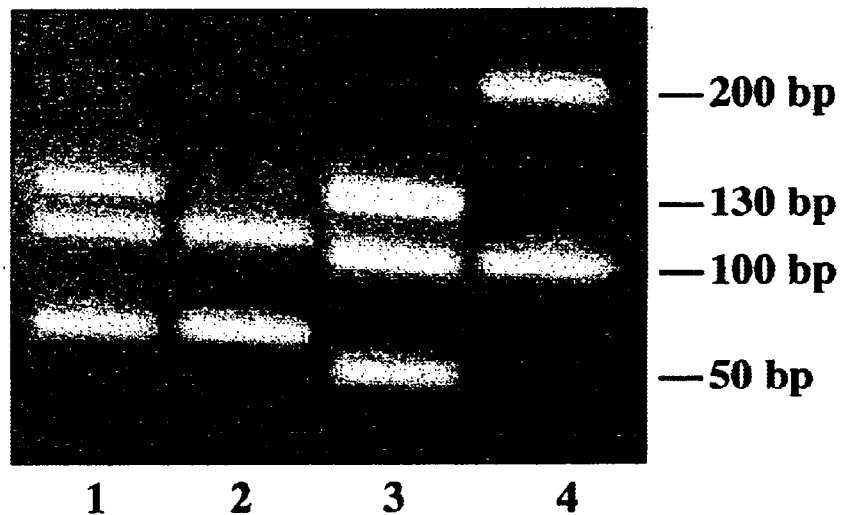
Figure 5A:
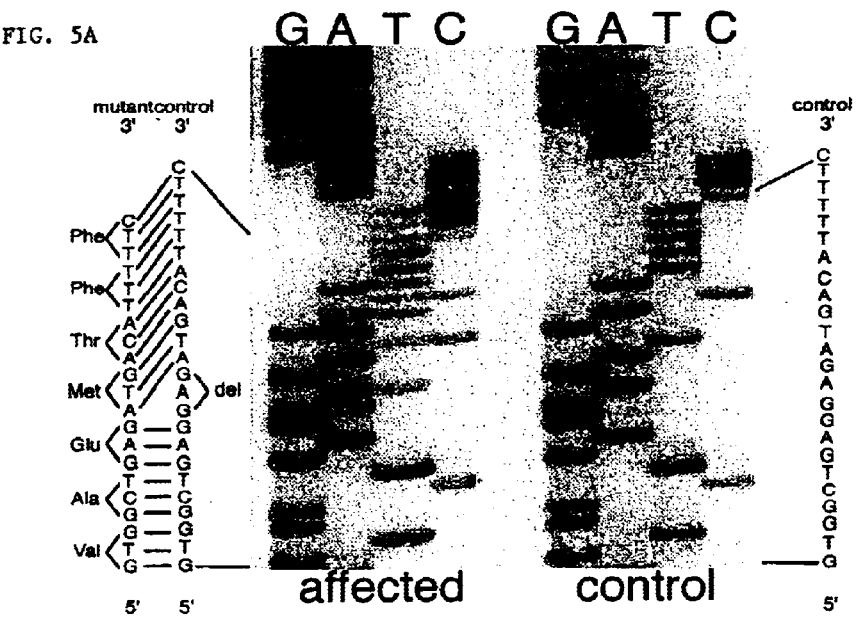
Figure 5D:
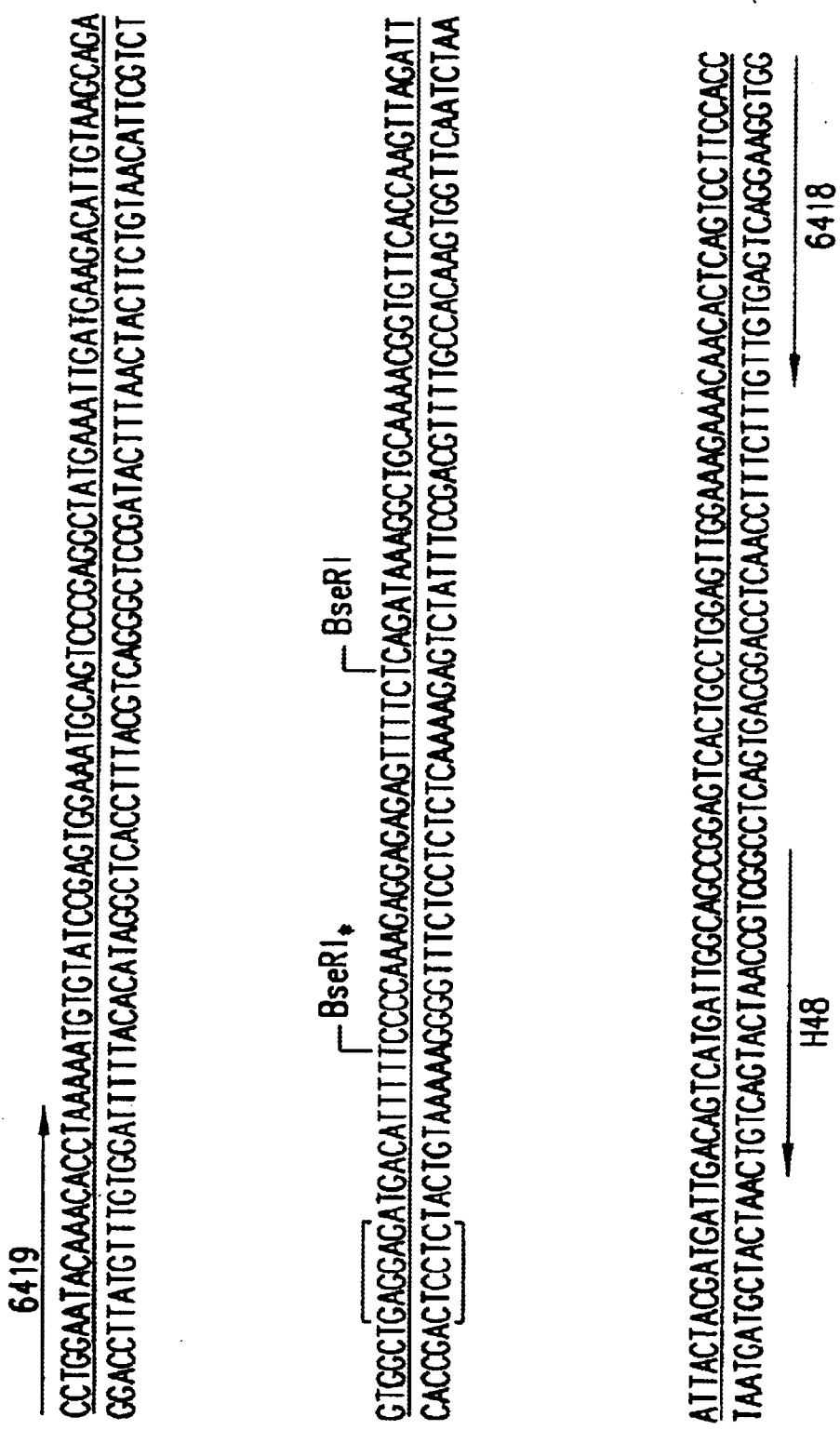
Figure 6:
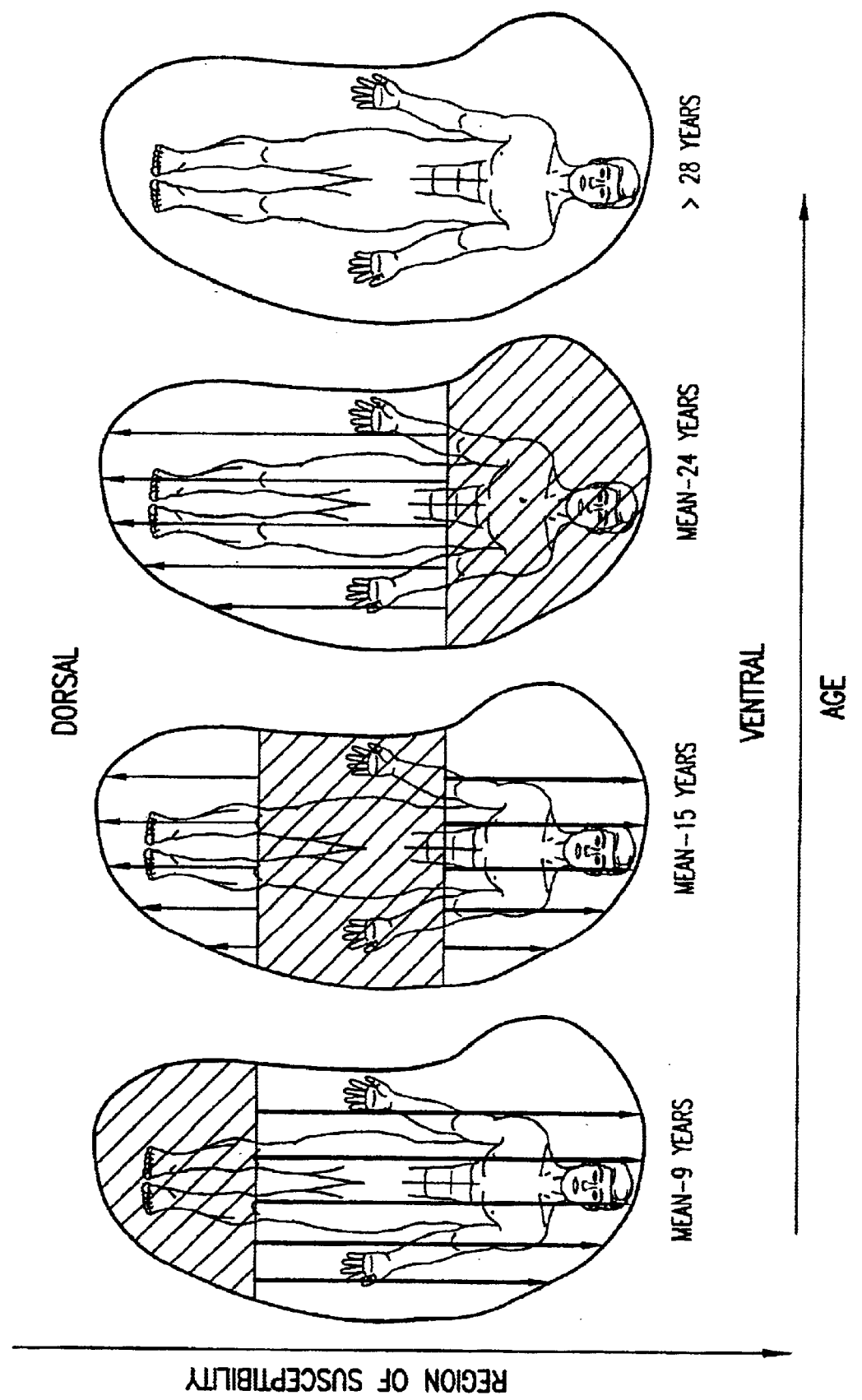
FIG. 6. Hypothetical model of neuronal involvement in early onset dystonia as a function of age. Dystonic symptoms are believed to arise through neuronal dysfunction in the basal ganglia. Neurons in this region of the brain have a anatomical patterning corresponding to the movements they subserve in the body, which can be represented roughly as an inverted homunculus. In early onset dystonia the physical site of onset of symptoms and tendency to generalize as a function of age can be represented as a zone of susceptibility (cross-hatched area) moving ventrally in the basal ganglia with age. Clinical analysis of carriers of the AJ founder mutation (Bressman, S. B., et al., 1994, *Annal. Neurol.* 36:771–777) reveals that the earlier the onset of symptoms, the more likely they are to commence in lower limbs and the greater the tendency (thick black arrows) to generalize and involve upper parts of the body. With increasing age of onset, symptoms tend to involve progressively higher body parts, and still tend to progress upward. By >28 years of age, carriers of the early onset gene have passed the age of susceptibility and have only a small remaining chance of manifesting any symptoms. Still, as gene carriers, these "escapees" are at equal risk as affected gene carriers for having affected children.

There are few other clues from the deduced protein sequences of this apparently new class of proteins that yield insight into their function. The forty-one amino acids at the putative N-terminal of torsinA consist of two 20 amino acid hydrophobic domains. The first of these begins with two basic amino acids, and ends with a polar and an acidic amino acid; it fulfills the criteria of a leader sequence for a transmembrane or membrane translocated protein (Boyd, D., et al., 1990, *Cell* 62:1031–1033). There are several possible phosphorylation sites which are conserved in both torsinA and torsinB: two for protein kinase C, and one for casein kinase II; as well as a number of putative N-myristylation sites (Prosite analysis). Six cysteine residues are conserved with other torsin family members (FIG. 4B).

The finding of the same 3-bp mutation in the heterozygous state in most cases of typical early onset dystonia is surprising. There are only a few examples of recurrent mutations which cause dominantly inherited conditions. These include: loss of a positively charged arginine in the fourth transmembrane helix of the I subunit of the L-type voltage sensitive calcium channel, which is the only type of mutation found to cause hypokalemic periodic paralysis (Grosson, C. L., et al., 1995, *Neuro. Disord.* 6:27–31; Fontaine, E., et al., 1994, *Nat. Genet.* 6:267–272); a glycine to arginine substitution in the membrane domain of the fibroblast growth factor receptor-3 (FGFR3) seen in almost all cases of achondroplasia (Bellus, G. A., et al., 1995, *Am. J. Hum. Genet.* 56:368–373); common missense mutations seen in hypertrophic cardiomyopathy (Watkins, H., et al., 1993, *Am. J. Hum. Genet.* 53:1180–1185); and CAG expansions in the coding regions of a number of genes causing neurodegenerative diseases (Gusella, J., et al., 1979, *Proc. Natl. Acad. Sci.* USA 76:5239–5242; Paulson, H. L. and Fishbeck, K. H., 1996, *Ann. Rev. Neurosci.* 19:79–107). In all these cases it appears that the same mutations occur repeatedly as independent events, while other mutations in the same gene apparently cause a different syndrome, have no phenotype, or are incompatible with life.

Early onset dystonia (DYT 1) represents the most severe and most common form of hereditary dystonia. This and other genetic forms of dystonia usually follow an 117:859–876; Kulisevsky, J., et al., 1993, *Movement Disorder* 8:239–240). Dystonia may result, in particular, from disruption of dopaminergic neurotransmission as genes defective in dopa-responsive dystonia encode proteins in the dopamine pathway (above); drugs that block dopaminergic transmission via the D2 receptor can elicit acute or tardive dystonic symptoms (Christian, C. D., et al., 1958, *Eng. J. Med.* 259:828–830; Burke, R. E., et al., 1982, *Neurology.* 32:1335–1346), and abnormally low levels of dopaminergic metabolites have been noted in the cerebrospinal fluid of some dystonic patients (Tabaddor, K., et al., 1978, *Neurology.* 28:1249–1253; Wolfson, L. I., et al., 1988, *Adv. Neurol.* 50:177–181; Brashear, A., et al., 1996, *Mov. Disord.* 2:151–156). The clinical features of early onset dystonia reflect developmental and somatotopic patterns in the basal ganglia. Neuromorphologic and physiologic studies in experimental animals have demonstrated an anatomic gradient of postnatal modelling in neural cell adhesion molecules (Szele, F. G., et al., 1994, *Neurosci.* 60:133–144) and dopaminergic innervation of the striatum (Graybiel, A. M., 1984, *Neuroscience.* 13:1157–1187). This developmental gradient overlies a somatotopic distribution of neurons in the basal ganglia subserving movements of different body parts (Crutcher, M. D., et al., 1984, *Exp. Brain Res.* 53:233–243), corresponding roughly to an inverted homunculus. In dystonia patients with the AJ founder mutation, the earlier the onset of symptoms between about 6 and 24 yrs of age, the more likely they are to occur in a lower limb and to generalize to other upper body parts (Bressman, S. B., et al., 1994, *Annal. Neurol.* 36:771–777). These ages appear to define a developmental period of susceptibility; as carrier's of the same mutation who manifest no symptoms by 28 years will usually remain symptom-free for life. This developmental model of neuronal involvement in dystonia provides a platform for evaluating subtle neuromorphologic and physiologic changes in the basal ganglia. The ability to identify cells expressing the torsinA transcript should help to identify the neurons involved in dystonia.

The apparent lack of neuronal degeneration in early onset dystonia provides hope for therapeutic intervention. In fact, even delaying onset of symptoms in this form of dystonia might result in a milder phenotype. Most patients with dopa-responsive dystonia, a condition that mimics DYT 1 clinically, are virtually cured by administration of levo-dopa and this treatment remains effective over the patient's lifetime. A minority of patients with typical early onset dystonia have shown improvement with various medications, including high dose anticholinergics, doparnine agonists and antagonists, and GABAergic agents, and in some cases drugs have been terminated without remission after the age of susceptibility is past (Fahn, S., et al, In: *Movement Disorders* 2, Eds.: Marsden, C. D. et al., London: Butterworths (1987), pp. 332–358; Pranzatetti, M. P, 1996, *J. Child Neurol.* 11:355–369; Bressman, S. B., et al., 1990, *Neurol. Clin.* 8:51–75). Further, patients with the best response to anticholinergics tend to be those who are treated early in the course of the disease (Greene, P., et al., 1988, *Mov. Disord.* 2:237–254).

EXAMPLE 5

Diagnostic Testing

It is to be understood that the diagnostic methods described herein can be practiced by amplifying nucleic acid sequence from any region (e.g., exon) of a DYT1 or DYT1-related gene (e.g., TOR1A, TOR1B, TORP1 or TORP2) using test samples which are obtained from individuals who are either at an increased risk (e.g., who are genetically predisposed) of developing a neurologic disease or from an individual who is afflicted with a nuerologic disease. Thus, the following exemplification which demonstrates the use of the methods and primers disclosed herein to diagnose dystonia is not intended to limit the scope of the invention in any way.

This test is performed using polymerase chain reaction (PCR) to amplify part of exon 5 in the DYT1 gene from DNA isolated from whole blood. All individuals have two DYT1 alleles, one maternal in origin and one paternal. After electrophoresis of PCR products, individuals carrying one allele with the GAG deletion will demonstrate two bands while individuals with two normal alleles will demonstrate one band.

Detection of DYT1 alleles using PCR amplification is achieved by using two oligonucleotide primers which flank the region of exon 5 surrounding GAG nucleotides 946–948. The sequence of the primers are depicted in italics, the normal sequence of part the DYT1 gene and the GAG deletion (underlined) is shown in SEQ ID NO: 27 below:

5'-*CCTGGAATACAAACACCTA*AAAATGTGTATCCGAGTGGAAATGCAGT

CCCGAGGCTATGAAATTGATGAAGACATTGTAAGCAGAGTGGCTGAGGAG

ATGACATTTTTCCCCAAAGAGGAGAGAGTTTTCTCAGATAAAGGCTGCAA

AACGGTGTTCACCAAGTTAGATTATTACTACGATGATT*GACAGTCATGAT*

*TGGCAGCC*-3' (SEQ ID NO: 27)

The oligonucleotide primers 5'-CCTGGAATACAAACACCTA-3' (SEQ ID NO: 28) and 5'-GGCTGCCAATCATGACTGTC-3' (SEQ ID NO: 29) are purified by UHPLC. One of the primers is end labeled with a fluorescent molecule which results in a PCR amplified product that can be detected with high sensitivity by a fluorescent imager such as the Hitachi FMBIO® II. Following PCR, the labeled amplified products are separated on denaturing polyacrylamide sequencing gels and imaged. The presence or absence of a deleted allele is determined by comparing to normal (no dystonia disorder) and positive (dystonia disorder) controls.

The DYT1 assay controls are cell lines obtained from Coriell Cell Repositories. Genomic DNA is extracted from the cells and samples run in parallel with patient DNA samples. The cell line GM04282A is employed as a normal control and cell line GM02264A a positive control. These controls have been fully characterized and validated. A "no DNA" control is also prepared at the end of each PCR reaction. This control serves as an indicator of any systematic contamination of reagents that could cause signals that resemble the PCR products of DYT1 alleles.

Migration of marker bands through the gel are used to determine if the gel has run properly and to aid in PCR product size determination. The fluorescent ladder consists of 16 fragments which emit at 597 nm. These bands are more visible using a 605 filter of the Hitachi FMBIO® II; however, sufficient signal will be detected using the 585 filter. The eighth and ninth bands from the top of the gel are 225 and 200 bp respectively and are used to size DYT1 PCR products.

DNA is extracted from blood samples using art-recognized protocols. (Ausubel, etal., In: *Current Protocols in Molecular Biology*, John Wiley & Sons, (1998)). Following quantification, by standard methods such as UV absorbance, DNA is diluted to a concentration of 50 ng/µL and subjected to PCR amplification in the presence of oligonucleotide primers SEQ ID NOS: 28 and 29 using standard methods (Ausubel, et al., In: *Current Protocols in Molecular Biology*, John Wiley & Sons, (1998)). The fluorescently labeled primers should only be exposed to light when in use.

Fluorescent PCR products are run on gels and fluorescent imaging performed using, for example, a Hitachi FMBIO® imager. Analysis of DYT1 images relies on pattern match of patient samples to normal and positive controls. Detailed instructions on software operation can be found in "FMBIO® User's Manual" by Hitachi Software.

The DYT1 PCR products appear as one or two major bands (205 and 202 base pairs in size) on the image from a gel. Background bands are differentiated from these major bands using the following criteria:

1. A lighter band appearing directly below a major DYT1 PCR product band, generating the image of a doublet, does not interfere with diagnosis and should not be scored.
2. DYT1 PCR products exhibiting a single major band (205 base pairs) may also show a light background band slightly below the position where the second major band migrates (202 base pairs). This background band will usually be apparent in the a normal Control sample and/or overloaded normal patient samples.

Signals in the patient (e.g., individual afflicted with a neuronal disease) test sample lanes are compared to the normal and positive control signals and a pattern match is made. For example, dystonia patient samples are scored by indicating either the presence of only the 205 or the 205 and the 202 base pair band. Patients in the first category have two normal alleles, while patients in the second category have one allele with the GAG 946–948 deletion mutation and one normal allele which indicates a negative and positive diagnosis, respectively.

If additional analysis of the image has been performed, and if two bands are present in the same lane, the difference of their sizes in bp should be approximately three. In addition, the value for every normal band should be approximately 205 bp and 202 bp for samples with a second, affected band.

EXAMPLE 6

Features of DYT1 (TOR1A) and Related Genes

Clinical criteria and patient samples from affected individuals were obtained through the Movement Disorders Groups at Columbia Presbyterian Medical Center, Mount Sinai School of Medicine and Beth Israel Hospital (New York) under IRB approved, informed consent protocols. The criteria for the diagnosis of primary torsion dystonia and the methods of evaluation were the same as described previously (Bressman, S. B., et al.,1994, *Ann. Neurol.* 36:771–777.).

DNA was processed according to standard methods (Sambrook, J., Fritsch, E. F., and Maniatis, T., 1989, In: *Molecular Cloning. A Laboratory Manual.*, Cold Spring Harbor Laboratory Press, Cold Spring Harbor). Cosmids spanning the TOR1A region (Ozelius, L. J., et al., 1997, *Nature Genetics* 17:40–48.) were sequenced directly using primers spaced throughout the cDNAs (DQ1 and DQ2, Ozelius, L. J., et al., 1997, *Genome Res.* 7:483–494). The resultant genomic sequence was aligned with the cDNA sequence revealing the exon/intron boundaries. The size of the introns was determined by amplifying across the introns using exonic primers with Elongase enzyme and 1.8 mM $Mg^{2+}$ when possible, according to manufacturers instructions (Life Technologies).

Dideoxy cycle sequencing was performed with the Perkin-Ehner AmpliSequence Sequencing kit (Perkin-Elmer) using specific primers labeled with [α-$^{33}$P]dATP (2000 Ci/mmol; NEN). Direct cycle sequencing (step 1, 95° C. 2 min; step 2, 95° C. 1 min; step 3, 60° C. 1 min; step 4, 72° C. 1 min; cycle steps 2–4×25; step 5, 4° C. 5 min) was performed after enzymatic clean-up with exonuclease I and shrimp alkaline phosphatase (USB) for 15 min at 37° C. and 15 min at 85° C.

Following DNA extraction from whole blood or lymphoblastoid lines following standard protocols, PCR amplification was performed using primers comprising nucleotides 1380–1398 of SEQ ID NO: 1 as the forward primer and nucleotides 1632–1614 of SEQ ID NO: 1 as the reverse primer which span the critical region of the TOR1A gene (Ozelius, L. J., et al., 1997, Genome Res. 7:483–494). PCR products were resolved on a denaturing 6% polyacrylamide gel and visualized by silver staining (Deimling, A., et al, 1993, Neuropathol. Appl. Neurobiol. 19:524–529; Klein, C., et al., 1999, Genet. Test. 3:323–328).

The amino acid sequences of torsinA and torsinB were used to search the database of expressed sequence tags (dbEST) to identify additional homologs and orthologs. ESTs were grouped by nucleotide sequence, and used to search dbEST iteratively. In seven cases, UniGene clusters were identified that represent homologs. ESTs were assembled into contigs with Sequencher (GeneCodes), or with the EST Assembly Machine and EST Extractor at TIGEM (http://gcg.tigem.it/cgi-bin/uniestass.pl; http://gcg.tigem.it/blastextract/estextract.html). Amino acid sequences of EST contigs were predicted from open reading frames with similarity to torsinA and torsinB. The *C. elegans* database (http://www.sanger.ac.uk/Projects/C_elegans/blast_server.shtml) was searched to identify predicted proteins from the *C. elegans* genome project. Gene designations were approved by the Human and Mouse Naming Committees.

Phylogenetic relationships were determined by alignment of the predicted amino acid sequences of torsins, torps and heat-shock proteins using ClustalX (Thompson, J. D., et al., 1994, Nucleic Acids Res. 22:4673–4680). The tree was calculated by ClustalX with 1000 bootstrap trials, excluding positions with gaps and correcting for multiple substitutions, and was displayed for plotting with TreeView 1.5 (http ://taxonomy.zoology.gla.ac.uk/rod/rod.html).

Secondary structure predictions were made using the Protein Sequence Analysis Server at Boston University (http://bmerc-www.bu.edu/psa/).

Figure 7:
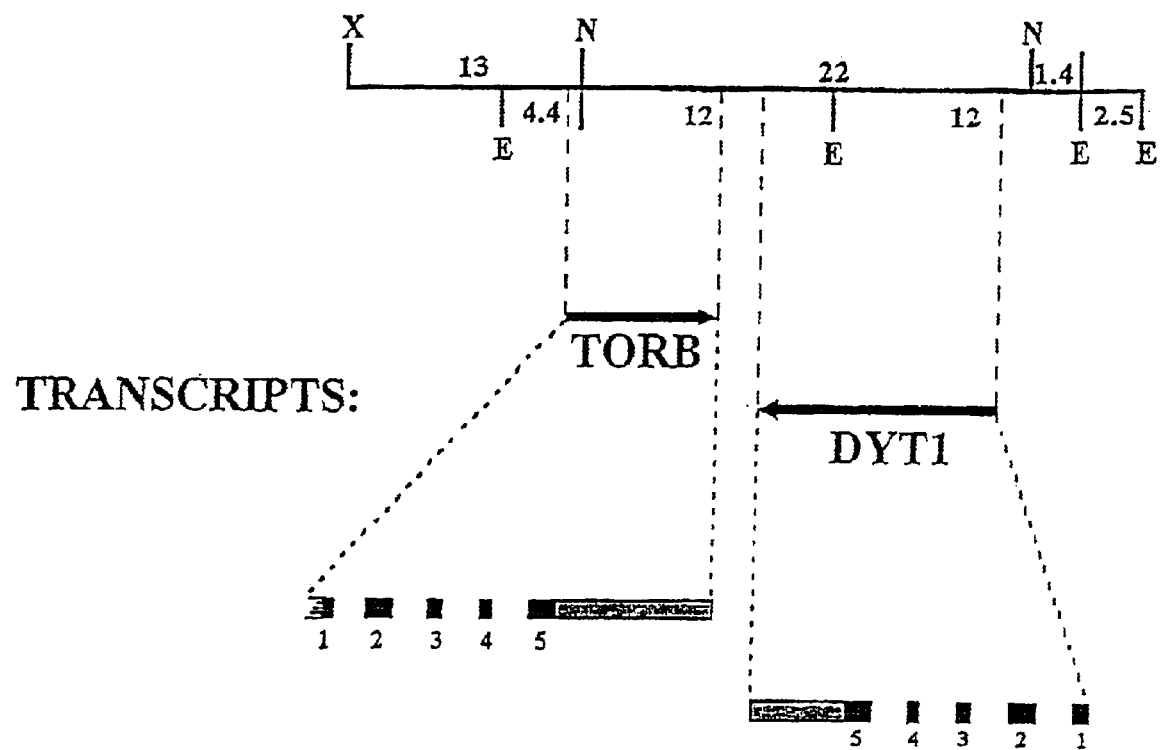
FIG. 7. Exon structure and orientation in chromosome. Top: The restriction map of this genomic region: restriction enzymes—X=XbaI, E=EcoRI, N=Not1, and fragment sites (Ozelius, L. J. et al., 1997, *Nature Genetics.* 17:40–48). Middle: the extent and orientation of TOR1B and TOR1A genes (arrows) are shown relative to the restriction map of this genomic region. Bottom: the exon structures are depicted as exons in boxes with coding in solid boxes and nontranslated regions in shaded boxes.

Human TOR1A (also referred to herein as DYT1) and TOR1B transcripts (DYT1 or DQ2, and DQ1, respectively) were found previously to be highly similar (71% identical at the amino-acid level) and encoded by adjacent genes on chromosome 9q34, which face in opposite orientations with their 3' ends as nearest neighbors (Ozelius, L. J., et al., 1997, Nature Genetics 17:40–48; Ozelius, L. J., et al., 1997, Genome Res. 7:483–494). Each gene has five exons spanning about 10 kb, with the same location of splice sites; these two genes are separated from each other in the genome by about 2 kb (FIG. 7). The size of the exons and introns of these genes, and the nucleotide sequences near the intron/exon junctions, are listed in FIGS. 9A and 9B.

Dystonic individuals were screened for mutations. It is possible that other mutations, in addition to the GAG deletion, occur in the TOR1A gene and that at least some of these may cause dystonia or other neurogenic diseases. Thus, a mutational screen of coding sequences was undertaken for TOR1A and TOR1B for three groups of dystonia patients (n=23). All affected individuals tested negative for the GAG-deletion. The first group consisted of 17 patients (5 of AJ descent and 12 non-Jewish) with typical features of early onset dystonia, including limb onset from 3 to 19 yrs of age with spread to involve at least one, and frequently multiple, body parts (FIG. 10). The second group comprised 5 patients (4 AJ and 1 AJ/NJ) with early to mid-life onset (4 to 35 yrs) whose haplotype in the TOR1A region appeared homozygous. This homozygosity could have resulted from consanguinity or deletion of genomic DNA in this region on one chromosome, for some or all of the polymorphic markers—D9S2160, D9S2161, D9S63, D9S2162, in a ≦320 kb region, including the TOR1A locus Ozelius, L. J., et al., 1997, Nature Genetics 17:40–48; FIG. 11). The third group was represented by one individual from a set of 11, out of 88 AJ patients tested with late onset, focal dystonia, who carried the same haplotype for nine polymorphic markers (D9S62a, D9S62b, D9S159, D9S2158, D9S2159, D9S2160, D9S63, D9S2162, ASS), which span the TOR1A region. Age of onset in these 11 patients ranged from 29–66 yrs (mean age 48 yrs) with focal symptoms involving neck (3), larynx (2), upperface (4) or arm (2). Phasing of these chromosomes was possible in one family with two affected individuals confirmed a common haplotype.

Genomic DNA from these 23 patients was used to amplify exons from TOR1A and TOR1B with the flanking intronic primers listed in FIGS. 12A and 12B. A screen of known coding sequence in the five exons of TOR1A (excluding the 40 bp of the coding region and the 5 prime splice junction of exon 1, as this region is very G-C rich and proved difficult to consistently amplify) and exons 2–5 of TOR1B (except for the region around the 5' end of intron 1 which was difficult to PCR) did not reveal any new changes which would alter the amino acid sequence of the protein or the splicing of the messages. A number of previously described polymorphisms were observed (Ozelius, L. J., et al., 1997, Nature Genetics 17:40–48) of the five apparently homozygous patients was heterozygous at any of three polymorphisms in the TOR1A gene (Ozelius, L. J., et al., 1997, Genome Res., 7:483–494), leaving open potential homozygosity or hemizygosity due to a chromosomal deletion.

Figure 8:
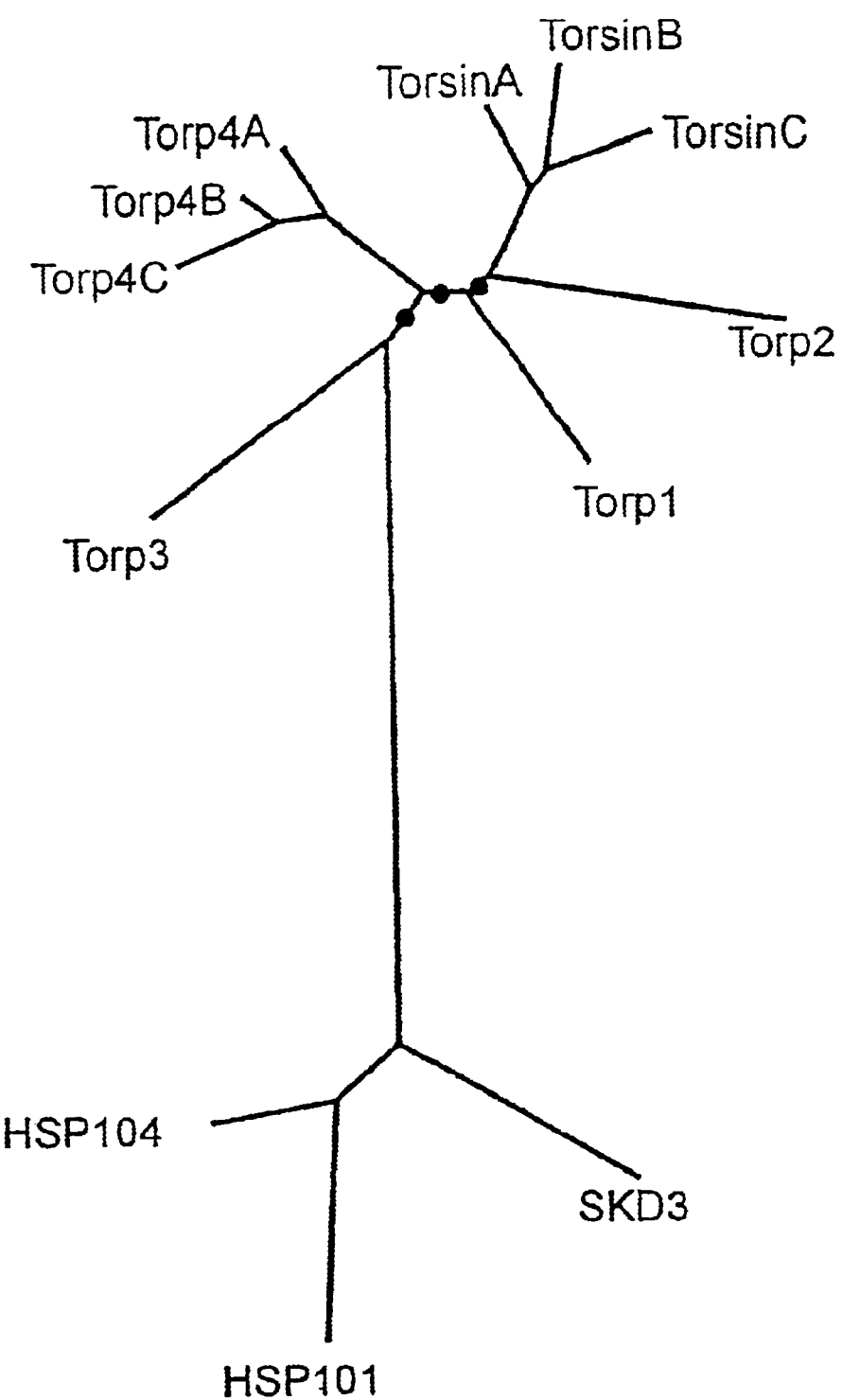
FIG. 8. Phylogenetic relationships among the Torsin family, and relationship to the HSP101 family. For each protein, the ortholog for which there was the longest sequence was used for the phylogeny analysis. Orthologs, when included, are represented by much shorter branches than those separating homologs (not shown). Branches marked by dots are not statistically significant.

There is a gene family of torsins and torsin-related proteins in different species. The sequences of torsinA and torsinB were used to search databases for orthologs and homologs in other species. Mouse orthologs of both genes are represented by ESTs, which are clustered in the UniGene database. Pig and rat orthologs for torsinA are also present in the EST database. Homologs were also identified in mammals, fish, flies and nematodes (see FIG. 13). A phylogenetic analysis of the predicted protein sequences (FIG. 8) indicated that one of these, an EST from zebrafish, is closely related to torsinA and torsinB, but not sufficiently similar to represent an orthodox, and so is termed torsinC.

Other homologs are more distant from the torsins, and so are termed torsin-related proteins, or torps. Torp2 and torp3 are expressed by both mouse and human. Human ESTs for both torp2 and torp3 and mouse ESTs for torp2 are clustered in the UniGene database, which facilitated assembly of cDNA sequence (FIG. 13). Torp4 is expressed by *Drosophila melanogaster*, but apparently not by other species. The three torps expressed by *Caenorhabdities elegans* are more related to each other than to other members of the family, and so together are denoted as torp5, with subtypes a, b and c. Since the *C. elegans* genome project is largely complete, there are probably not additional members in nematodes. An apparent pseudogene for TOR1B is located on human chromosome 2p 13 with several BAC clones from this region showing highly homologous sequences; however, there is no open reading frame of any length among these sequences.

Some members of the HSP101 superfamily of heat-shock proteins, representing both class 1 and class 2 subtypes were included in the phylogenetic analysis (Parsell, D. A. and Lindquist, S., 1993, Ann. Rev. Genet. 27:437–496). These clearly group together, but far from the torsins and torps. Thus, the Torsin family of proteins is not simply a branch of the HSP101 family, but is a separate group that shares some characteristic domains (Ozelius, L. J., et al., 1997, Genome Res. 7:483–494).

TorsinA shares functional domains with a family of chaperone proteins, termed Clp ATPase/heat shock proteins (HSP), of which hsp104 is a member ((Schirmer, E. C., et al., 1996, TIBS. 21:289–296). Family members are distinguished by binding of nucleotides (they typically have ATPase activity), association as oligomeric homomers, and interaction with other non-homologous oligomeric proteins (frequently proteases). These chaperone proteins help to fold newly synthesized proteins and escort them to their correct cellular locations, and can protect cells from a variety of stresses, such as high temperature, drugs and oxidative damage, by re-folding or degradation of denatured proteins. Of note, carriers of the DYT1 mutation frequently first manifest dystonic symptoms following an infectious illness or physical injury. In situ hybridization to the DYT1 message in control human brain reveals that it is expressed strongly in only a few brain regions, including dopaminergic neurons in the substantia nigra, and that expression appears to correlate with prolonged stress prior to death (Augood, S. J., et al., 1998, Ann. Neurol. 43:669–673). We hypothesize that the GAG-deleted torsinA partially blocks stress repair mechanisms in these neurons, thereby compromising their function and resulting in insufficient release of dopamine into the striatum. It is not hard to imagine that more disruptive mutations in the DYT1 gene could lead to stress-related death of these dopaminergic neurons which will ultimately be manifest as neuronal disease.

Several lines of evidence point to the importance of chaperone proteins and proteases in correct folding or degradation of denatured proteins involved in neurodegenerative diseases (Welch, W. J. and Gambetti, P., 1998, Nature 392:23–24). Many of these diseases show frank accumulation of aggregated proteins closely associated with neuronal degeneration, including: (α-synuclein and ubiquinated proteins in the Lewy bodies in classic Parkinson's disease (Spillantini, M. G., et al., 1997, Nature 388:839–840); triplet repeat expanded forms of huntington as nuclear inclusion bodies in Huntington's disease (DiFiglia, M., et al., 1997, Science 277:1990–1993) extracellular β-amyloid plaques with ubiquinated proteins in Alzheimer's disease, including patients with mutant forms of the β-amyloid precursor protein (Wisniewski, T., et al., 1997, Neurobiol. Dis. 4:313–328); and prion protein (PrP)-ubiquitin inclusions in prion diseases, including Kreutzfeldt-Jacob disease and Gerstmann-Straussler Scheinker syndrome (Suenaga, T., et al., 1990, Ann. Neurol. 28:174–177; Migheli, A., et al., 1991, Neurosci. Lett. 121:55–58). Notably, in a model system, Lindquist and colleagues have shown that the physical state, i.e., soluble versus aggregated/insoluble, of two prion proteins—yeast Sup35 and mammalian PrPC, can be determined by the availability of the chaperone proteins, yeast hsp 104 and bacterial GroEL, with other chaperone/heat shock proteins being ineffectual in this context. Thus a member of the same chaperone family as torsinA, namely hsp 104, has been demonstrated to be effective in the interconversion of a human prion protein between aggregated and soluble states. Mutations in three novel proteins apparently involved in chaperone/proteolytic pathways have now been identified as responsible for human neurologic diseases, including: early onset torsion dystonia (Ozelius, L. J., et al., 1997, Nature Genetics 17:40–48), early onset Parkinson's disease, and Angelman syndrome. All of these diseases occur in the context of neuronal development (prenatal and/or postnatal), supporting a role for these proteins in neuronal plasticity, as well as in protection from stress.

The TOR1A (DYT1) gene for early onset torsion dystonia is remarkable in two ways: the large majority of patients with this syndrome bear the same mutation (GAG deletion) in the heterozygous state and identification of this gene reveals a novel family of proteins with features of the heat shock/chaperone and AAA+ superfamily (Ozelius, L. J., et al., 1997, Genome Res. 7:483–494; Neuwald, A. F., et al.,1999, Gen. Res. 9:27–43). These data defines the exon structure of this gene and an adjacent homolog, TOR1B.

The structural change in the torsinA protein caused by the GAG deletion (loss of glutamic acid residue in carboxy terminal) may be functionally unique. While a phylogenetic analysis of the TOR1A gene family showed it to represent a distinct branch related to the AAA+ (HSP/Clp-ATPase—AAA) superfamily, a detailed sequence comparison between the torsin family members and this superfamily has revealed shared functional and configurational domains (Ozelius, L. J., et al., 1997, Genome Res. 7:483–494; Neuwald, A. F., et al., 1999, Gen. Res. 9:27–43). This superfamily is typified by hexameric architecture, protein-protein interactions, and conformational changes mediated by ATP hydrolysis, and its members mediate a wide range of cellular functions. The function of torsinA remains to be determined, but the high conservation of this family among species suggests an important role in cell biology.

Dominantly inherited conditions, such as early onset dystonia, can result from mutant forms of a protein that either act in a "gain of function" manner unrelated to the functions of the normal protein counterpart, e.g., in triplet repeat diseases where extended glutamine residues cause intracellular precipitation of proteins (Paulson, H. L. and Fishbeck, K. H., 1996, Ann. Rev. Neurosci. 19:79–107; Ross, C. A., 1997, Neuron. 19:1147–1150; DiFiglia, M., et al., 1997, Science 277:1990–1993), or in a "dominant negative" manner, blocking normal functions of oligomeric protein complexes, such that even a minority of mutant subunits in the complex can disrupt its function, e.g., a missense mutation in one subunit of a $K^+$ channel that causes deafness (Kubisch, C., et al., 1999, Cell. 96:437–446). This latter mechanism seems intriguing for dystonia, as members of the AAA+ family typically form six-member, homo-oligomeric ring structures, which interact with one or more other proteins, frequently with substrate proteins or nucleic acids "threaded" through the hole in the ring.

The recently described crystal structure of NSF (Lenzen, C. U., et al., 1998, Cell. 94:525–536; Neuwald, A. F., et al., 1999, Gen. Res. 9:27–43.; Yu, R. C., et al., 1998, Nat. Struct. Biol. 5:803–811)—a member of the AAA+ family involved in vesicle fusion (Whiteheart, S. W., et al., 1994, J. Cell Biol. 125:945–954)—and alignment of torsinA with its structural domains, suggests that the region of the GAG deletion in torsinA may be involved either in formation of the ring structure or interaction with partner proteins. Mutations in the carboxy terminal portion of some of the HSP proteins, e.g., Hs1U and FtSH (filamentation temperature sensitive protein), can block association with the partner proteins in a dominant manner, thereby inhibiting proteolytic function of the complex (Missiakas, D., et al., 1996, *EMBO J.* 15:6899–6909; Akiyama, Y., et al., 1994, *J. Biol. Chem.* 269: 5225–5229). By analogy, the GAG deletion in the carboxy region of torsinA could prevent function of an oligomeric complex, even if only a few subunits of a heteromeric torsinA ring bear the mutation. Thus, in the heterozygous condition, with expression of normal and mutant (GAG-deleted) forms of torsinA, the function of the complex might be compromised. Other mutations in torsinA present in the heterozygous state might not disrupt function to the same extent and thus might lead to a milder or no phenotype. However, disruptive mutations present in both alleles of torsinA might cause dystonia or another type of neurogenic disease.

Three possible outcomes of other mutations in TOR1A are possible. First, any mutation that disrupts the function of the oligomeric complex might lead to a syndrome of dominantly inherited, early onset dystonia. Presumably only a limited number of changes in the structure of torsinA could produce a "dominant-negative" effect, and some of these might be present in those early onset, generalized dystonia patients who do not bear the GAG-deletion. To test this possibility a set of AJ and NJ patients without the GAG deletion who had early onset dystonia (<19 yrs) which began in a limb and progressed to involve at least one other body part (not excluding cranial involvement) was evaluated.

Second, if disruption of torsinA function causes dystonia, then null mutations in both alleles of the TOR1 A gene might also produce a dystonic syndrome. In the course of haplo-type analysis in dystonia cases, a number of individuals were identified who were apparently homozygous for alleles in and around the TOR1A locus and thus might bear a disruptive mutation in one TOR1A allele and deletion of the other allele.

Third, some cases of late onset/focal dystonia might be caused by dominantly acting, but less disruptive mutations in the TOR1A gene. This latter thesis was supported by the finding that 11/88 AJ patients with late onset dystonia appeared to share a common haplotype in the TOR1A region (Ozelius, L. J.,1994, *Ph.D. Thesis* Harvard Medical School), suggesting a possible founder mutation with a milder phenotype. Sequence analysis of coding regions of TOR1A and TOR1B genes in genomic DNA from these three types of affected individuals, however, revealed no further mutations in TOR1A, nor any in TOR1B. It remains possible that mutations in non-coding sequences in the 5' flanking region or introns of these genes can disrupt transcription, processing or stability of these messages, or that the GAG-deletion confers a novel, deleterious property to torsinA. These patients may also have mutations in one of the 12 or more other human gene loci implicated in primary dystonia (Mueller, U., et al., 1998, *Neurogenetics.* 1:165–177), including other members of the TOR1A gene family or loci encoding non-homologous proteins that interact functionally with torsinA. To date, however, all multiplex families with early onset dystonia with linkage to 9q34 have the GAG deletion. Further, some patients manifesting apparent homozygosity in this chromosomal region may be hemizygous for TOR1A and/or TOR1B genes with a consequent haploinsufficiency state.

The present study provides the foundation for further analysis of the torsinA gene family and its role in human disease. The elucidation of gene structure of TOR1A and TOR1B and description of intronic primers for PCR allow the search for mutations to continue at the genomic level. The elucidation of a cross-species and multi-member gene family should aid in defining other genetic predispositions and neuronal diseases mediated by this protein family. The features of torsinA shared with the HSP/Clp-ATPase and AAA superfamily and the implication of compromised dopaminergic function in dystonia provide clues as to the function of this new class of proteins.

EXAMPLE 7

Screening Test Samples from Parkinson Patients for Mutations in DYT1 and Related Genes The role of the DYT1 gene and related genes in neurogenic diseases, such as Parkinson disease, can be assessed as follows: 1)identify mutations that affect the integrity of expression of the torsin/torp gene family; and 2) assess polymorphic variations in these and other genes which may influence the manifestation (penetrance) of the disease.

The screening method of the subject invention will be described herein as an embodiment useful for determining the role of the DYT1 gene in Parkinson's disease patients. However, it should be understood that the invention is not limited to detecting the presence or absence of a mutation or polymorphism in a DYT1 gene.

Genomic DNA isolated from typical Parkinson's disease patients can be assessed for the presence or absence of mutations in the DYT1 gene (5 exons) or a related neuronal gene by, for example, PCR amplification of exons, single strand conformational analysis of PCR fragments to detect sequence variations, and sequencing of variant fragments. If patient lymphoblastic cell lines exist it is also possible to assess the relative expression of both alleles of the gene, as marked by polymorphic variations or mutations. Other members of this gene family can be screened for mutations in patients in this same way, if they are found to be expressed in human neuronal (e.g., peripheral nervous system or central nervous system) tissues. For example, central nervous system expression can de determined by in situ hybridization analysis of tissue samples obtained from the cerebellum, locus ceruleus, substantia nigra or hippocampus regions of the brain.

In addition, polymorphic variations (present in at least 1% of human chromosomes) in the torsin/torp gene family and in ox-synuclein and parkin, which may affect penetrance of the disease state can also be evaluated.

Sample Set

Genomic DNA was isolated from 91 unrelated males with onset of Parkinson's disease over 50 yrs (Hotamisligil, G. S., et al., 1994, *Movement Disorders* 9:305–310) who met the standard clinical criteria including: two of three cardinal signs (tremor at rest, bradykinesia, rigidity), improvement with L-dopa, and no evidence of secondary parkinsonism; as well as a set of 45 age-matched, neurologically unimpaired males. In addition, Applicants will have access to a projected 100 samples per year from Parkinson's disease patients and control spouses collected as part of the NIH-finded Parkinson's disease sib-pair consortium study. These samples, will comprise affected sib pairs, unaffected siblings and parents, when available. Applicants also have access to DNA samples and disease status information for the chromosome 2p 13-linked Parkinson families as the initial collection of families of European descent, in which Dr. Gasser found linkage (Gasser, T., et al., 1998, *Nat. Genet.* 18:262–265.).

Mutational Analysis

Test samples obtained from patients afflicted with a neuronal disease (e.g., Parkinson disease) can be screened for mutations in genomic DNA, as well as RNA by RT-PCR analysis in lymphoblast lines. To assess the relative contribution of the two alleles to the mRNA expression in cells from patients, we will carry out parallel analysis in genomic DNA and lymphoblast RNA (RT-PCR) using polymorphic variations and/or mutations in the coding region to mark alleles. For example, the DYT1 gene has 6 common single base pair changes (two in the coding region and four in the untranslated 3' end) of the torsinA message, one of which results in a change of aspartic acid to histidine in the protein (Ozelius, L. J., et al., 1997, *Nature Genetics* 17:40–48).

The DYT 1 gene, or any other neuronal gene, can be evaluated for the presence or absence of mutations by numerous techniques well-known to one of skill in the art. For example, this determination can be made by exon amplification, using PCR and single strand conformational analysis (SSCP) to screen for sequence variations followed by sequencing of shifted bands, as in previous studies (Tivol, E. A., et al., 1996, *Amer. J. Med. Gene.* (*Neuropsychiatric Genetics*) 67:92–97.; Ozelius, L. J., et al., 1997, *Nature Genetics* 17:40–48.). The human DYT1 gene has 5 exons spanning 10 kb and containing 998 bp of coding sequence. We have generated intronic and untranslated sequence primers (SEQ ID NOS: 30–39) which flank the coding sequence and can scan the entire coding sequence in seven PCR reactions, generating fragments of <200 bp which are optimal for SSCP analysis. Using the nucleotide sequences provided herein, in particular the 5' and 3' nucleotide sequences of the cDNA clones presented in FIGS. 14–21 one of skill in the art could easily identify alternative intronic and untranslated sequence primers suitable for use in amplifying individuals exons of TOR1A or TOR1B. Further, Applicants provide herein, intronic and untranslated sequence primers (SEQ ID NOS: 40–47) sufficient to enable analysis of the coding region of TOR1B.

Further, individual exons can be screened by PCR amplification of genomic DNA using appropriately spaced intronic and exonic primers (Saiki, R. K., et al., 1988, *Science* 239:487–491; Tivol, E. A., et al., 1996, *Amer. J. Med. Gene.* (*Neuropsychiatric Genetics*) 67:92–97). First strand cDNA synthesized from appropriate patient and control lymphoblast RNA can be amplified, using radiolabeled precursors in the reaction, to produce 100–200 bp fragments that will be analyzed for differences in SSCP profiles (as above). For example, a typical PCR reactions will contain 0.2 mM each dATP, dCTP, dTTP; 2.5 μM dGTP, 4 ng/μL of each oligonucleotide; 0.08 μL $\alpha$-$^{32}$P-dGTP(>3000 Ci/mM); 1×Taq polymerase buffer; and 0.05 μL Taq polymerase with 5 ng total genomic DNA in 10 μL. The thermocycler program used is 94° C. for 1.5 min; then 25 cycles of 94° C. for 1 min, 55° C. for 1 min, and 72° C. for 1 min; with a terminal extension step at 72° C. for 9 min. Amplified fragments will be denatured in 50% formamide at 95° C. loaded immediately onto non-denaturing 5% acrylamide gels, containing 2% crosslinker and 5 or 10% glycerol, resolved by electrophoresis at room temperature or 4° C. (Orita, M., et al., 1989, *Genomics* 5:874–879; Hayashi, K. and Yandell, D. W., 1993, *Hum. Mutation* 2:338–346.), and visualized by autoradiography. A variety of gel conditions can be employed to maximize the probability of identifying altered mobility, including variations in acrylamide concentration, matrix crosslinking percentages, and running temperatures (Hayashi, K., and Yandell, D. W., 1993, *Hum Mutation* 2:338–346.). All fragments with altered migration will be sequenced directly using an enzymatic cleanup process with exonuclease I and shrimp alkaline phosphatase (USB) for 15 min at 37° C. and 15 min at 85° C., followed by standard dideoxy chain termination sequencing (Sanger, F., et al., 1977, *Proc. Natl. Acad. Sci.* USA 74:5463–5467). Sequence variations will be evaluated in >60 controls (120 alleles) to determine whether they represent normal polymorphisms, and in affected families to check inheritance.

Cycle sequencing can be carried out using the Sequitherm Long Read Cycle Sequencing Kit (Epicenter Technologies) developed specifically for the LiCor machine. The premix includes 0.5–1 μg of template DNA, depending on the size of the template (more template is used for longer fragments); 2.5 μL of 10×PCR buffer; 1.0 μL Sequitherm DNA polymerase; 1.0 μL of infrared labeled T3 or T7 vector primers (1 pmole), or when using $^{33}$P-dATP, 1 μL of $^{33}$P-dATP (2000 Ci/mmol, NEN), 1 μL of specific primer (100 ng) to a final volume of 16.5 μL with water. Five ml of this premix is added to 4 tubes each containing 2 μL of a single dideoxy dNTP (ddG,A,T or C). The reactions are amplified in a Perkin Elmer 9600 PCR machine using the following program: 92° C. for 2 min followed by 30 cycles of 92° C. for 30 sec; 47–70° C., 30 sec, (annealing temperature is maximized for each primer); and 70° C. for 30 sec. The cycling is followed by a final 5 min extension at 70° C. When PCR is complete, 3 μL of stop solution is added and the samples are denatured and resolved on a 6% denaturing acrylamide gel. The LiCor sequence is read using the BaselmagIR software package which includes data collection and image analysis software. The $^{33}$PdATP gels are transferred to 3 MM Whatman, dried and exposed to autoradiographic film overnight. This sequence is read and entered into the GCG Sequencher programs manually.

One of skill in the art can readily genotype appropriate Parkinson's disease patients for the genes encoding: torsinA, ($\alpha$-synuclein and parkin, and probably for TORB, TRP1 and TRP2, as well as haplotype status at the 2p Parkinson's disease locus.

The mutational analysis described above focuses on detecting sequence variations in the coding region of the DYT1 gene. One of skill in the art will acknowledge that other mutations occurring in, for example but not limited to, the promoter, introns or untranslated portions of the message can also affect expression of alleles of DYT1 or related genes. It is to be understood that these other mutations are withing the scope of the instant invention. It is also to be understood that the invention further encompasses employing the probes, primers and methods described herein to determine the role of torsin and torsin-related genes in other neruonal diseases in which patients have a phenotype consistent with a role for these genes.

Sequence Analysis of other Genes

Sequence variations in other genes present in DNA samples obtained from Parkinson's disease patients, for example, a related DYT1 genes (e.g., TORB, TRP1 or TRP2), an $\alpha$-synuclein and a parkin gene can also be readily determined by the methods described above.

The TORB gene encoding torsinB (70% homology in coding sequences to torsinA), which lies adjacent to DYT1 on chromosome 9q34, appears to share identical exon structure to DYT1.

The DYT1-related genes, TRP1 and TRP2, were identified through BLAST searches of the expressed sequence tag (EST) database of sequences at the National Center for Biotechnology Information (NCBI). The I.M.A.G.E. cDNA clones (Research Genetics) corresponding to these ESTs can be sequenced, for example, on a LiCor (model 4000 LX) automated DNA sequencer using standard cycle sequencing methods. Suitable software for reading the sequence includes but is not limited to the BaselmagIR software package (LiCor). The isolated cDNA clones can subsequently be hybridized to Northern blots containing polyA+ RNA from various normal adult and fetal human tissues (Clontech). This will establish the tissue distribution of expression and the approximate length of the mRNA derived from each gene. With this information, various pieces of the I.M.A.G.E. clones (i.e., most 5' or 3' ends) can be used to screen human fetal and adult cDNA libraries (from appropriate tissues) by colony hybridization (Sambrook, J., Fritsch, E. F., and Maniatis, T., 1989, In: *Molecular Cloning. A Laboratory Manual.*, Cold Spring Harbor Laboratory Press, Cold Spring Harbor). The identified cDNAs will be sequenced as described above, assembled using the Sequencher program (Gene Codes Corp.) and analyzed with BLAST and FASTA programs verses the NCBI databases and the DYT1 and TORB cDNA sequences. If necessary, 5' ends of the cDNAs can be obtained using a RACE (rapid amplification of cDNA) technique (Frohman, M. A., et al., 1988, *Proc. Natl. Acad. Sci.* USA 85:8998–9002), as modified by Clontech (Apte, A. N. and Siebert, P. D., 1993, *Biotechniques.* 15:890–893). cDNA sequences and primers which distinguish these genes (usually for 3' untranslated sequences) can be screened for in situ hybridization studies in human brain. Sequences that are found to be expressed in dopaminergic neurons in the substantia nigra can be assessed for mutations in Parkinson's disease patients, whether or not they are expressed in other cell types.

One of skill in the art can design PCR assays utilizing the 3' untranslated (nonhomologous) end of each gene useful for assigning these genes to particular human chromosomal regions. PCR of DNA from a control somatic cell hybrid panel facilitates the assignment of a gene to a specific human chromosome and regional localization can be achieved using the Stanford Human Genome Center radiation hybrid panel (Research Genetics). Two possibilities exist: either TRP1 and/or TRP2 map to a region already known to or found to harbor an as yet unidentified gene involved in parkinsonism, i.e., chromosomes 2p (Gasser, T., et al., 1998, *Nat. Genet.* 18:262–265) or they map elsewhere.

Evaluation of Genetic Contributions to Penetrance and Susceptibility

With respect to Parkinson's patients genotyping data can be utilized to evaluate the penetrance of the 2p gene in linked family and to Parkinson's disease in affected sib pairs utilizing DNA samples from the families showing linkage to 2p13 with autosomal dominant inheritance (Gasser, T., et al., 1996, *Mov. Disord.* 11:163–166; Gasser, T., et al., 1998, *Nat. Genet.* 18:262–265). For example, samples from two particular families who are of German origin share a common haplotype on 2p13 suggesting the possibility of a founder mutation causing a subset of Parkinson's disease in this geographic/ethnic population, which may also appear in sporadic patients derived from this region. Penetrance of the 2p gene can be evaluated by typing individuals in these families can for microsatellite markers on 2p 13 in the region of the shared haplotype: D2S292-0.1 cM-D2S2115-0.0 cM-D2S327-0.0 cM-D2S2113-1.4 cM-D2S291-0.5 cM-DS2111-0.1 cM—D2S2109-0.6 cM-D2S2110-0.1 cM-D2S145-1.2 cM-D2S1394. This will allow for the identification of unaffected carriers. The fact that there are several instances of unaffected parents who produce affected children indicates that an autosomal dominant modifying gene affecting penetrance could be transmitted by the married-in parent. This implies that the "alteration" in the modifying gene which affects expression of this Parkinson gene may be relatively common in the general population, with an allele frequency on the order of perhaps 10–20%, consistent with a common polymorphism. Some individuals may carry a modifying gene, but may not have been old enough to show signs of the disease. Unaffected status will be weighted based on the age of the individual when last examined. Thus, we will incorporate an age-dependent penetrance function, in which penetrance is low (~25%) prior to age 50, and then increases to a maximum, moderately high value (~75%) by the age of 75. The modifier trait could also be multigenic, or a complex system of polygenic loci, each with a small, but additive or interactive effect.

The hypothesis of autosomal dominant transmission of a single modifier gene is attractive for several reasons: 1) it is the simplest explanation; 2) it is consistent with the pattern of disease expression in our pedigrees; 3) we should be able to detect an association of such a modifier gene in our study sample; and 4) it is relatively inexpensive and labor-efficient to test this hypothesis, given current genetic technology. In addition we will evaluate genotype status, including 2p13 and 6q25–27 in sib pairs in which are both affected with Parkinson's disease to see if they share common haplotypes. (Allelic markers will be phased into haplotypes using siblings and parents.) Haplotype status for 6q25–27 will be evaluated using markers D6S305 and D6S253 which are tightly linked to the parkin locus. We have selected to carry out complementary haplotype analysis for the 6q25.2–27 region, which carries the parkin gene, and not for the 4p region which carries the (α-synuclein gene, as mutations associated with the former are deletions and do not exclude the possibility of another gene in the introns flanking exon 4 as being the real culprit. To evaluate the significance of associations between allelic (DYT1, parkin, (X-synuclein, etc.) or haplotype (2p13 and 6q25.2–27) status and affected status in genetically predisposed families, and in sib pairs we will carry out two point comparisons, using the Pearson $c^2$ and Fishers exact test (STATA, computer Resource Center, Santa Monica, Calif., 1992) as described (Hotamisligil, G. S., et al., 1994, *Movement Disorders* 9:305–310).

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims. The teachings of all references cited herein are hereby incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule selected from the group consisting of SEQ ID NOS: 48–51, 53–56 and 89, or the complement thereof.

2. An isolated nucleic acid molecule consisting of about 15 to 50 consecutive nucleotides from a nucleotide sequence selected from the group consisting of SEQ ID NOS: 48–51, 53–56 and 89, or the complement thereof.

3. An isolated nucleic acid molecule selected from the group consisting of SEQ ID NOS: 52, 88 and 90, or the complement thereof.

4. An isolated nucleic acid molecule consisting of about 15 to 50 consecutive nucleotides from a nucleotide sequence selected from the group consisting of SEQ ID NO: 52, 88 and 90, or the complement thereof.

* * * * *